(12) United States Patent
Lesh

(10) Patent No.: US 7,641,688 B2
(45) Date of Patent: Jan. 5, 2010

(54) TISSUE AUGMENTATION DEVICE

(75) Inventor: Michael Lesh, Mill Valley, CA (US)

(73) Assignee: Evera Medical, Inc., Foster City, CA (US)

( * ) Notice: Subject to any disclaimer, the term of this patent is extended or adjusted under 35 U.S.C. 154(b) by 586 days.

(21) Appl. No.: 11/316,215

(22) Filed: Dec. 22, 2005

(65) Prior Publication Data

US 2006/0161253 A1 Jul. 20, 2006

Related U.S. Application Data

(63) Continuation-in-part of application No. PCT/US2005/033252, filed on Sep. 15, 2005, and a continuation-in-part of application No. 10/942,728, filed on Sep. 16, 2004, now Pat. No. 7,244,270.

(51) Int. Cl.
*A61F 2/02* (2006.01)

(52) U.S. Cl. .................. 623/11.11; 623/23.72; 606/192

(58) Field of Classification Search ................. 623/1.11, 623/2.11, 17.11–17.12, 23.72, 11.11; 604/892; 606/61, 192
See application file for complete search history.

(56) References Cited

U.S. PATENT DOCUMENTS

| | | | |
|---|---|---|---|
| 2,512,568 A | 6/1950 | Saffir | |
| 3,293,663 A | 12/1966 | Cronin | |
| 3,366,975 A | 2/1968 | Pangman | |
| 3,919,724 A | 11/1975 | Sanders et al. | |
| 3,934,274 A | 1/1976 | Hartley, Jr. et al. | |
| 3,949,073 A | 4/1976 | Daniels et al. | |
| 3,953,566 A | 4/1976 | Gore | |
| 4,051,840 A | 10/1977 | Kantrowitz et al. | |
| 4,187,390 A | 2/1980 | Gore | |
| 4,327,734 A | 5/1982 | White, Jr. | |
| 4,383,929 A | 5/1983 | Bertocchio | |
| 4,395,806 A | 8/1983 | Wonder et al. | |
| 4,433,440 A | 2/1984 | Cohen | |
| 4,517,979 A | 5/1985 | Pecenka | |
| 4,531,244 A | 7/1985 | Hamas | |
| 4,543,088 A | 9/1985 | Bootman | |
| 4,545,367 A | 10/1985 | Tucci | |
| 4,592,755 A | 6/1986 | Penton et al. | |

(Continued)

FOREIGN PATENT DOCUMENTS

EP 0322194 6/1989

(Continued)

OTHER PUBLICATIONS

U.S. Appl. No. 11/575,493, filed Mar. 16, 2007, Lesh.

(Continued)

*Primary Examiner*—Suzette J Gherbi
(74) *Attorney, Agent, or Firm*—Knobbe, Martens, Olson & Bear LLP

(57) ABSTRACT

Disclosed are implantable tissue augmentation devices, methods, and associated tools. The devices include an inflatable body, having an inner layer and an outer layer. A valve is provided for permitting the introduction of and retaining inflation media. At least one pull tab is provided on an end of the implant, to assist in positioning the implant. Kits and systems are also disclosed.

133 Claims, 44 Drawing Sheets

U.S. PATENT DOCUMENTS

| | | | |
|---|---|---|---|
| 4,631,188 | A | 12/1986 | Stoy et al. |
| 4,643,733 | A | 2/1987 | Becker |
| 4,648,880 | A | 3/1987 | Brauman |
| 4,664,655 | A | 5/1987 | Orentreich et al. |
| 4,738,657 | A | 4/1988 | Hancock |
| 4,820,303 | A | 4/1989 | Brauman |
| 4,828,561 | A | 5/1989 | Woodroof |
| 4,828,827 | A | 5/1989 | Henderson et al. |
| 4,840,615 | A | 6/1989 | Hancock |
| 4,863,470 | A | 9/1989 | Carter |
| 4,908,029 | A | 3/1990 | Bark |
| 4,917,646 | A | 4/1990 | Kieves |
| 4,944,749 | A | 7/1990 | Becker |
| 4,955,907 | A | 9/1990 | Ledergerber |
| 4,963,150 | A | 10/1990 | Brauman |
| 4,966,478 | A | 10/1990 | Kuo |
| 4,969,901 | A | 11/1990 | Binder |
| 4,994,028 | A | 2/1991 | Leonard et al. |
| 5,007,929 | A * | 4/1991 | Quaid ............................ 623/8 |
| 5,019,101 | A | 5/1991 | Purkait et al. |
| 5,074,878 | A | 12/1991 | Bark et al. |
| 5,098,779 | A | 3/1992 | Kranzler et al. |
| 5,102,389 | A | 4/1992 | Hauser |
| 5,116,387 | A | 5/1992 | Berg |
| 5,123,905 | A | 6/1992 | Kelman |
| 5,141,508 | A | 8/1992 | Bark et al. |
| 5,181,921 | A | 1/1993 | Makita et al. |
| 5,188,558 | A | 2/1993 | Barton et al. |
| 5,213,574 | A | 5/1993 | Tucker |
| 5,273,532 | A | 12/1993 | Niezink et al. |
| 5,282,856 | A | 2/1994 | Ledergerber |
| 5,324,259 | A | 6/1994 | Taylor et al. |
| 5,356,429 | A | 10/1994 | Seare |
| 5,376,117 | A | 12/1994 | Pinchuk et al. |
| 5,387,192 | A | 2/1995 | Glantz |
| 5,425,747 | A | 6/1995 | Brotz |
| 5,425,760 | A | 6/1995 | Rosenberg |
| 5,437,900 | A | 8/1995 | Kuzowski |
| 5,454,788 | A | 10/1995 | Walker et al. |
| 5,456,716 | A | 10/1995 | Iversen et al. |
| 5,461,781 | A | 10/1995 | Pirc |
| 5,480,430 | A | 1/1996 | Carlisle |
| 5,496,367 | A | 3/1996 | Fisher |
| 5,496,370 | A | 3/1996 | Hamas |
| 5,545,217 | A | 8/1996 | Offray et al. |
| 5,545,220 | A | 8/1996 | Andrews et al. |
| 5,549,672 | A | 8/1996 | Maddock et al. |
| 5,558,641 | A | 9/1996 | Glantz |
| 5,558,829 | A | 9/1996 | Petrick |
| 5,571,189 | A | 11/1996 | Kuslich |
| RE35,391 | E | 12/1996 | Brauman |
| 5,582,585 | A | 12/1996 | Nash-Morgan |
| 5,584,859 | A | 12/1996 | Brotz |
| 5,599,852 | A | 2/1997 | Scopelianos et al. |
| 5,607,477 | A | 3/1997 | Schindler et al. |
| 5,630,843 | A | 5/1997 | Rosenberg |
| 5,630,844 | A | 5/1997 | Dogan et al. |
| 5,632,777 | A | 5/1997 | Petrick |
| 5,633,001 | A | 5/1997 | Agerup |
| 5,643,783 | A | 7/1997 | Olsen et al. |
| 5,645,081 | A | 7/1997 | Argenta et al. |
| 5,645,558 | A | 7/1997 | Horton |
| 5,653,755 | A | 8/1997 | Ledergerber |
| 5,653,757 | A | 8/1997 | Petrick |
| 5,660,849 | A | 8/1997 | Polson et al. |
| 5,674,285 | A | 10/1997 | Quaid |
| 5,702,677 | A | 12/1997 | Shimp et al. |
| 5,725,507 | A | 3/1998 | Petrick |
| 5,728,752 | A | 3/1998 | Scopelianos et al. |
| 5,779,672 | A | 7/1998 | Dormandy, Jr. |
| 5,779,734 | A | 7/1998 | Ledergerber |
| 5,782,913 | A | 7/1998 | Schindler et al. |
| 5,795,325 | A | 8/1998 | Valley et al. |
| 5,798,096 | A | 8/1998 | Pavlyk |
| 5,824,081 | A | 10/1998 | Knapp et al. |
| 5,861,032 | A | 1/1999 | Subramaniam |
| 5,863,297 | A | 1/1999 | Walter et al. |
| 5,871,537 | A | 2/1999 | Holman et al. |
| 5,922,025 | A | 7/1999 | Hubbard |
| 5,931,855 | A | 8/1999 | Bancke |
| 5,935,164 | A | 8/1999 | Iversen |
| 5,935,362 | A | 8/1999 | Petrick |
| 5,941,910 | A | 8/1999 | Schindler et al. |
| 5,944,738 | A | 8/1999 | Amplatz et al. |
| D413,672 | S | 9/1999 | Fogarty |
| 5,957,939 | A | 9/1999 | Heaven et al. |
| 5,961,552 | A | 10/1999 | Iversen et al. |
| 5,964,803 | A | 10/1999 | Iversen |
| 5,984,943 | A * | 11/1999 | Young ........................ 606/190 |
| 5,989,214 | A | 11/1999 | Van de Wijdeven |
| 5,989,216 | A | 11/1999 | Johnson |
| 5,997,574 | A | 12/1999 | Hayes et al. |
| 6,039,712 | A | 3/2000 | Fogarty |
| 6,053,899 | A | 4/2000 | Slanda et al. |
| 6,060,639 | A | 5/2000 | Petrick |
| 6,090,063 | A | 7/2000 | Makower et al. |
| 6,098,629 | A | 8/2000 | Johnson et al. |
| 6,146,418 | A | 11/2000 | Berman |
| 6,162,251 | A | 12/2000 | Kredovski |
| 6,171,298 | B1 | 1/2001 | Matsuura et al. |
| 6,187,043 | B1 | 2/2001 | Ledergerber |
| 6,214,045 | B1 | 4/2001 | Corbitt, Jr. et al. |
| 6,228,116 | B1 | 5/2001 | Ledergerber |
| 6,231,586 | B1 | 5/2001 | Mariant |
| 6,231,613 | B1 | 5/2001 | Greff et al. |
| 6,241,747 | B1 | 6/2001 | Ruff |
| 6,258,055 | B1 | 7/2001 | McCrory et al. |
| 6,261,323 | B1 | 7/2001 | Neto |
| 6,264,700 | B1 * | 7/2001 | Kilcoyne et al. ......... 623/23.68 |
| 6,267,772 | B1 | 7/2001 | Mulhauser et al. |
| 6,270,517 | B1 | 8/2001 | Brotz |
| 6,277,150 | B1 | 8/2001 | Crawley et al. |
| 6,299,590 | B1 | 10/2001 | Lüscher et al. |
| 6,312,405 | B1 | 11/2001 | Meyer et al. |
| 6,315,796 | B1 | 11/2001 | Eaton |
| 6,322,576 | B1 | 11/2001 | Wallace et al. |
| 6,379,329 | B1 | 4/2002 | Naglreiter et al. |
| 6,402,784 | B1 * | 6/2002 | Wardlaw .................. 623/17.11 |
| 6,440,098 | B1 | 8/2002 | Lüscher |
| 6,451,052 | B1 | 9/2002 | Burmeister et al. |
| 6,458,119 | B1 | 10/2002 | Berenstein |
| 6,470,216 | B1 | 10/2002 | Knowlton |
| 6,471,689 | B1 * | 10/2002 | Joseph et al. ............. 604/892.1 |
| 6,478,656 | B1 | 11/2002 | Khouri |
| 6,478,809 | B1 | 11/2002 | Brotz |
| RE37,950 | E | 12/2002 | Dunn et al. |
| 6,520,989 | B1 | 2/2003 | Eaton |
| 6,530,896 | B1 | 3/2003 | Elliott |
| 6,537,242 | B1 | 3/2003 | Palmer |
| 6,544,287 | B1 | 4/2003 | Johnson et al. |
| 6,551,342 | B1 | 4/2003 | Shen et al. |
| 6,578,580 | B2 | 6/2003 | Conrad et al. |
| 6,585,748 | B1 | 7/2003 | Jeffree |
| 6,599,310 | B2 | 7/2003 | Leung et al. |
| 6,629,947 | B1 | 10/2003 | Sahatjian et al. |
| 6,648,853 | B1 | 11/2003 | McEntee |
| 6,652,544 | B2 * | 11/2003 | Houser et al. ................ 606/153 |
| 6,660,301 | B1 | 12/2003 | Vogel et al. |
| 6,663,596 | B2 | 12/2003 | Griego et al. |
| 6,673,105 | B1 | 1/2004 | Chen |
| 6,684,107 | B1 | 1/2004 | Binder |
| 6,699,176 | B1 | 3/2004 | Khouri |
| 6,702,731 | B2 | 3/2004 | Milbocker |
| 6,716,251 | B1 | 4/2004 | Asius et al. |

| | | |
|---|---|---|
| 6,725,866 B2 | 4/2004 | Johnson et al. |
| 6,740,082 B2 | 5/2004 | Shadduck |
| 6,743,208 B1 | 6/2004 | Coyle |
| 6,755,861 B2 | 6/2004 | Nakao |
| 6,802,861 B1 | 10/2004 | Hamas |
| 6,878,137 B2 | 4/2005 | Benchetrit |
| 6,899,713 B2 * | 5/2005 | Shaolian et al. ............. 606/262 |
| 6,921,418 B2 | 7/2005 | Ledergerber |
| 7,077,865 B2 * | 7/2006 | Bao et al. ................ 623/17.12 |
| 7,094,230 B2 | 8/2006 | Flaherty et al. |
| 7,244,270 B2 | 7/2007 | Lesh |
| 2002/0019670 A1 | 2/2002 | Crawley et al. |
| 2002/0022861 A1 | 2/2002 | Jacobs et al. |
| 2002/0025340 A1 | 2/2002 | Dyer |
| 2003/0028147 A1 | 2/2003 | Aves et al. |
| 2003/0074021 A1 | 4/2003 | Morriss et al. |
| 2003/0074084 A1 | 4/2003 | Nakao |
| 2003/0225453 A1 | 12/2003 | Murch |
| 2004/0037887 A1 | 2/2004 | Bourne et al. |
| 2004/0243157 A1 | 12/2004 | Connor et al. |
| 2004/0249457 A1 | 12/2004 | Smith et al. |
| 2005/0131325 A1 | 6/2005 | Chen et al. |
| 2005/0177234 A1 | 8/2005 | Raphael |
| 2005/0187624 A1 | 8/2005 | Corbitt, Jr. |
| 2006/0058735 A1 | 3/2006 | Lesh |
| 2006/0058890 A1 | 3/2006 | Lesh |
| 2006/0058891 A1 | 3/2006 | Lesh |
| 2006/0058892 A1 | 3/2006 | Lesh et al. |
| 2006/0136070 A1 | 6/2006 | Pinchuk |
| 2006/0282164 A1 | 12/2006 | Seastrom |
| 2009/0125107 A1 | 5/2009 | Maxwell |
| 2009/0149953 A1 | 6/2009 | Schuessler et al. |

FOREIGN PATENT DOCUMENTS

| | | |
|---|---|---|
| EP | 0357927 | 3/1990 |
| EP | 0411767 | 3/1991 |
| WO | WO 95/22359 | 8/1995 |
| WO | WO 96/11647 | 4/1996 |
| WO | WO 99/17816 | 4/1999 |

OTHER PUBLICATIONS

*Review of Injectable Materials for Soft Tissue Augmentation*, Mark R. Homicz, M.D. et al., *Facial Plastic Surgery*, vol. 20, No. 1, 2004.

*Collagen, Human Collagen, and Fat: The Search for a Three-Dimensional Soft Tissue Filler*, Anthony P. Sciafani et al, *Facial Plastic Surgery*, vol. 17, No. 1, 2001.

*Patient Satisfaction with Expanded Polytetrafluoroethylene (Softform) Implants to the Perioral Region*, Stephen J. Wall, M.D., Ph.D., et al., *Arch Facial Plast* Surg, vol. 5, Jul./Aug. 2003.

U.S. Appl. No. 11/778,573, filed Jul. 16, 2007, Lesh.
U.S. Appl. No. 12/242,280, filed Sep. 30, 2008, Lesh.
U.S. Appl. No. 12/242,368, filed Sep. 30, 2008, Lesh.
U.S. Appl. No. 12/240,906, filed Sep. 30, 2008, Lesh
U.S. Appl. No. 12/241,970, filed Sep. 30, 2008, Lesh.
U.S. Appl. No. 12/241,818, filed Sep. 30, 2008, Lesh.
International Preliminary Report on Patentability for PCT/US2005/033252 mailed Mar. 29, 2007.
International Search Report for PCT/US2006/47870 mailed Nov. 6, 2008.
U.S. Appl. No. 12/024,826, filed Feb. 1, 2008, Kesten.
U.S. Appl. No. 12/024,835, filed Feb. 1, 2008, Kesten.
U.S. Appl. No. 12/024,843, filed Feb. 1, 2008, Kesten.
U.S. Appl. No. 12/024,846, filed Feb. 1, 2008, Kesten.
U.S. Appl. No. 12/412,830, filed Mar. 27, 2009, Lesh et al.
U.S. Appl. No. 12/413,240, filed Mar. 27, 2009, Lesh et al.

* cited by examiner

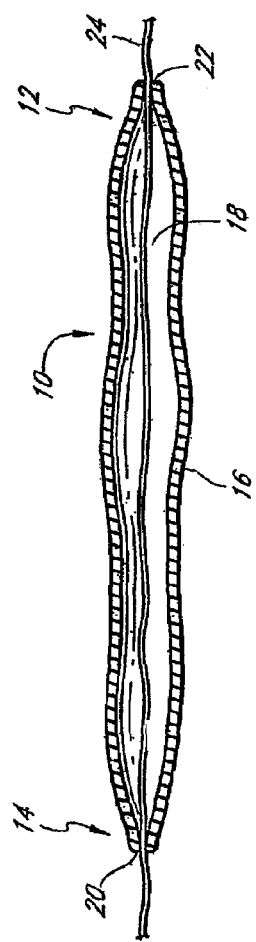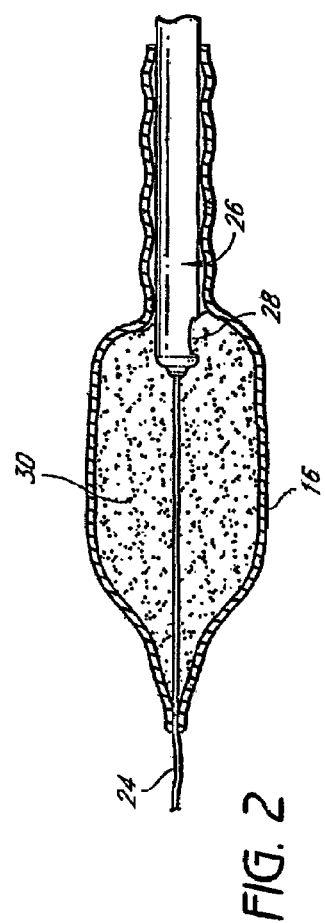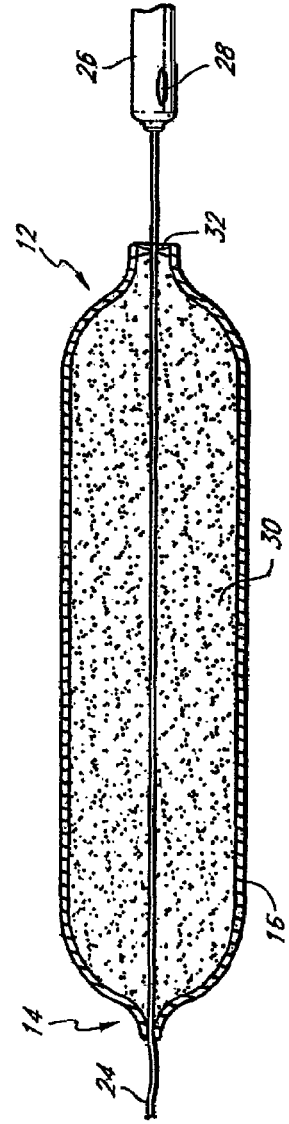

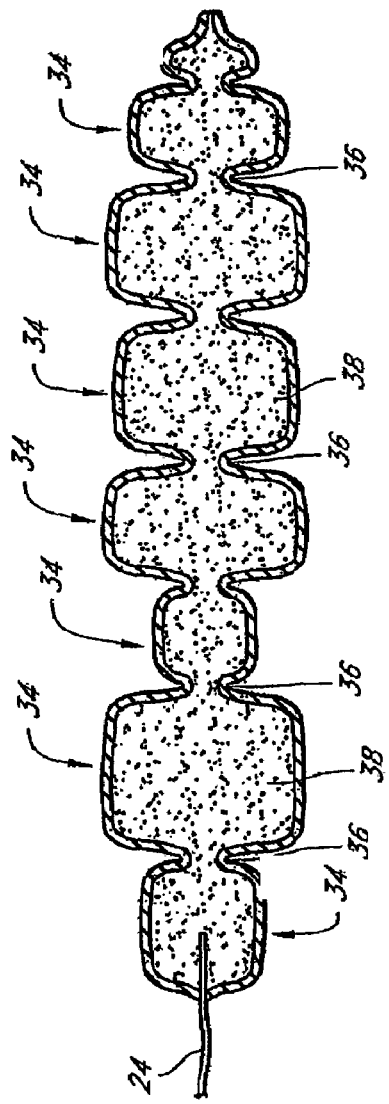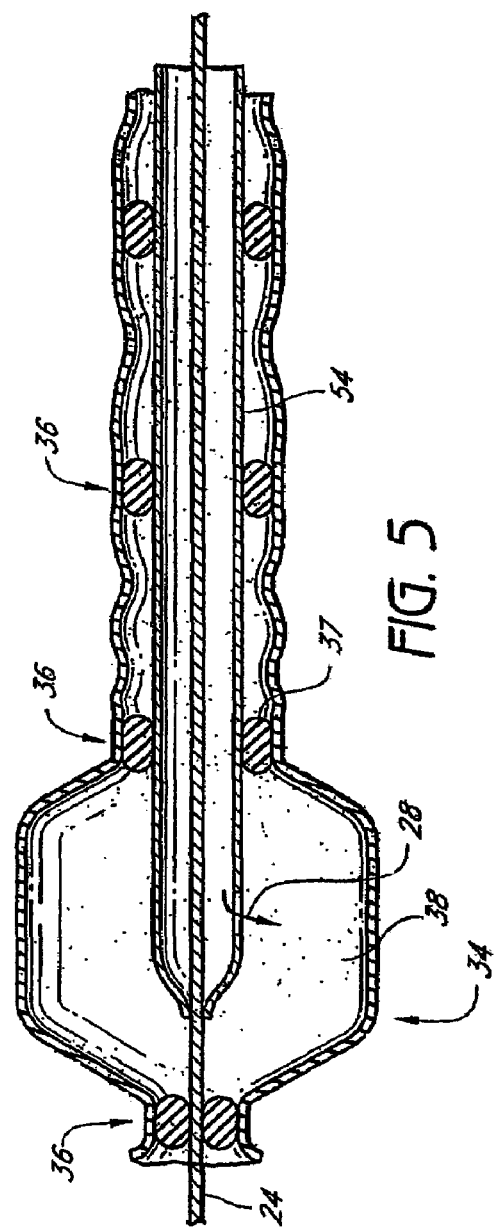

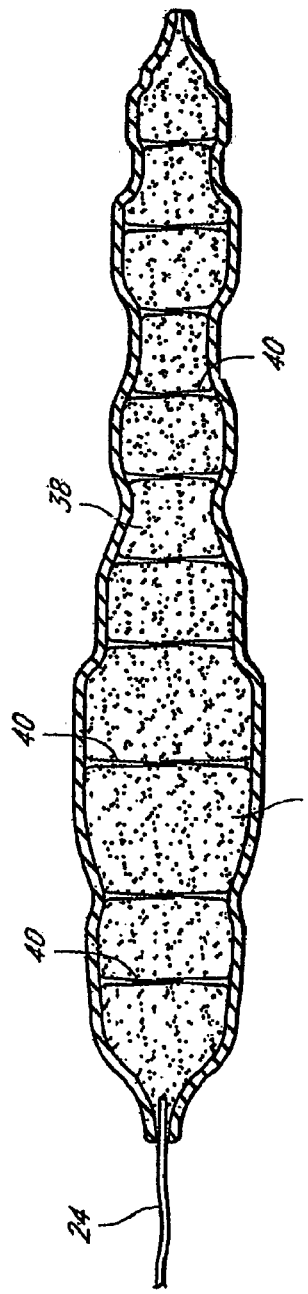
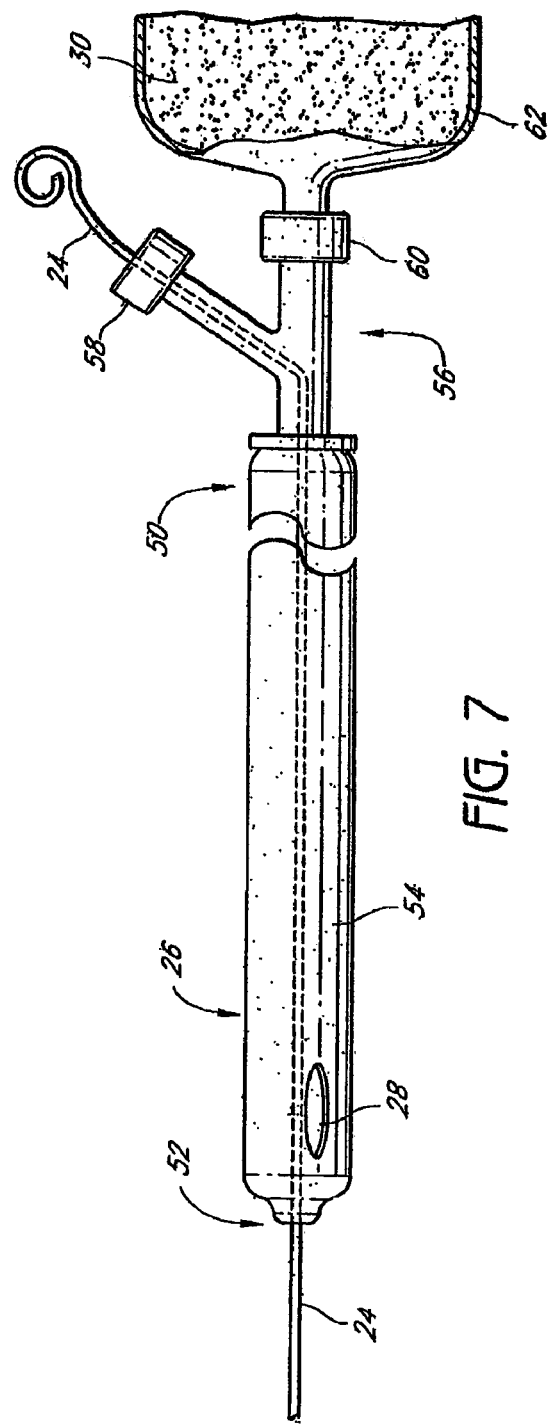
FIG. 6
FIG. 7

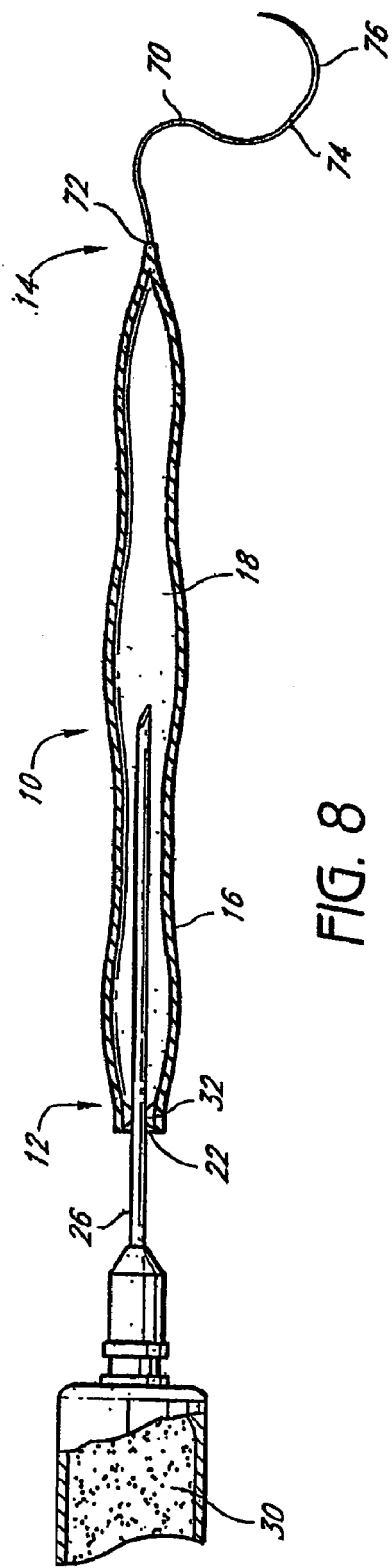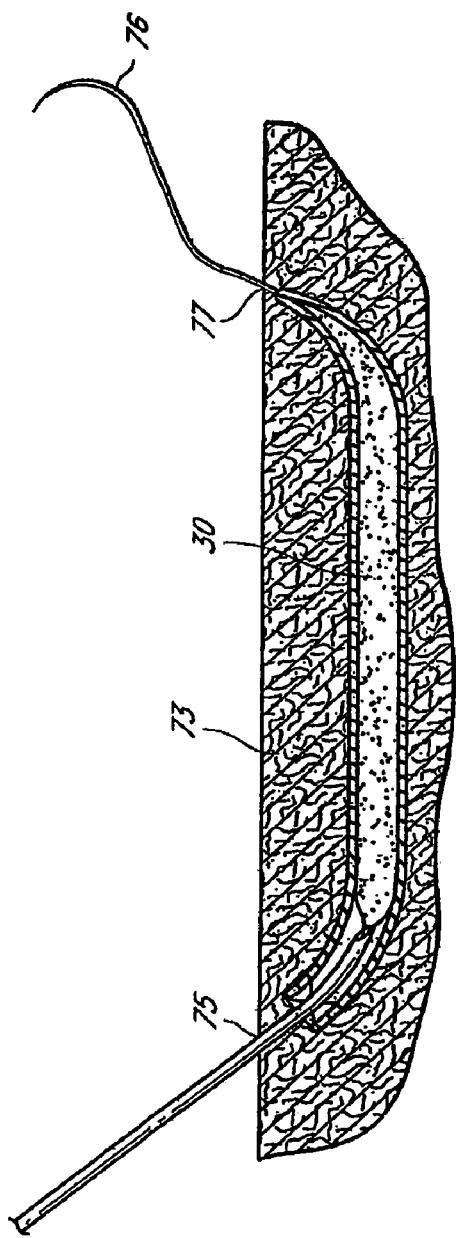
FIG. 8
FIG. 9

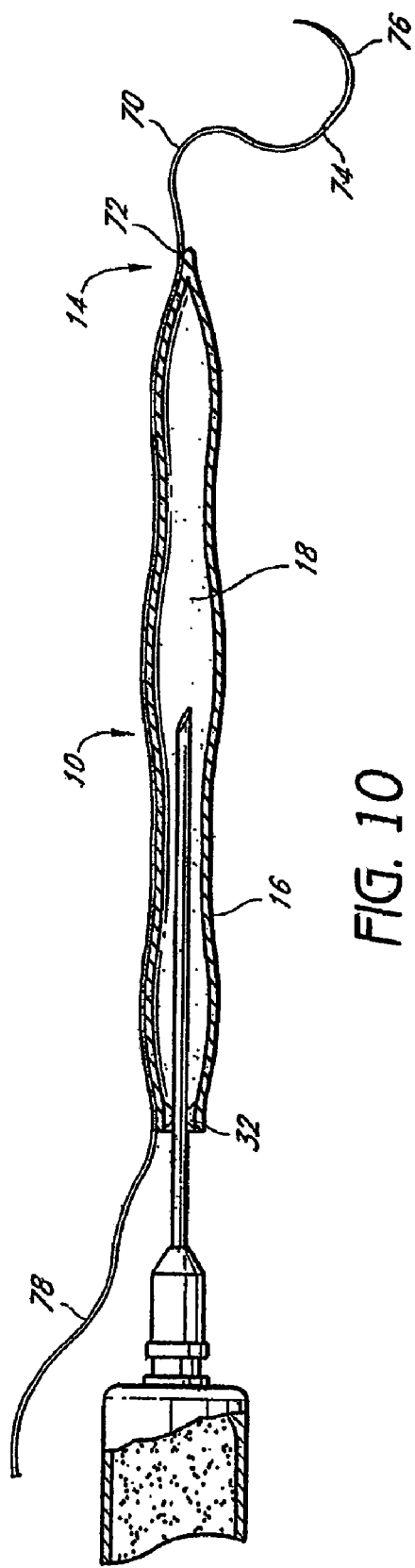
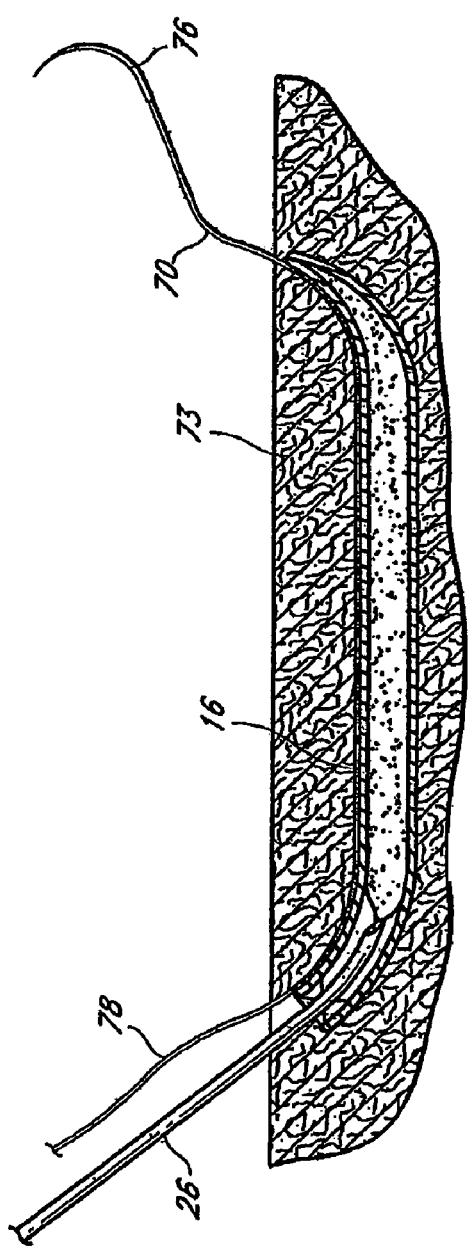
FIG. 10
FIG. 11

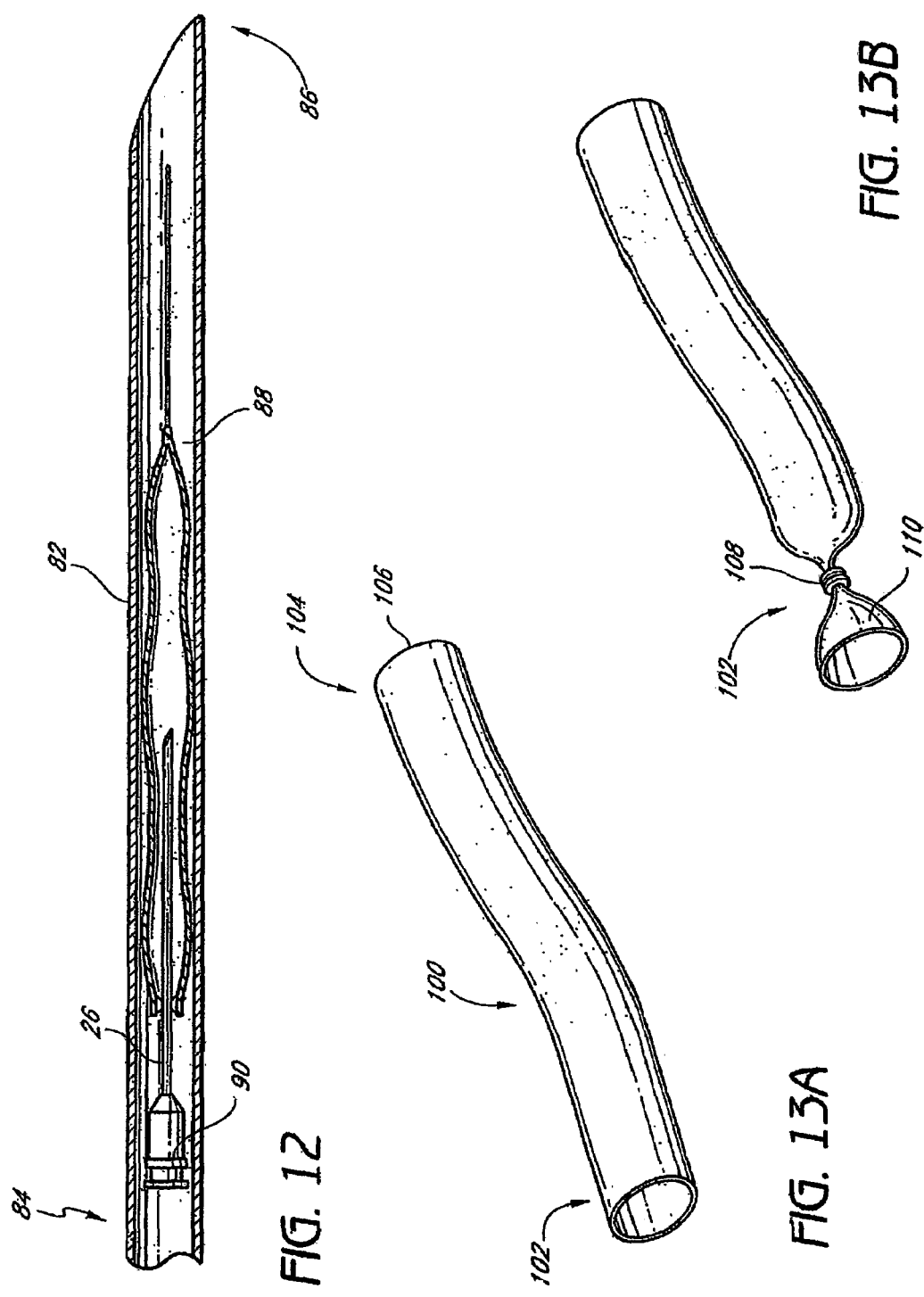

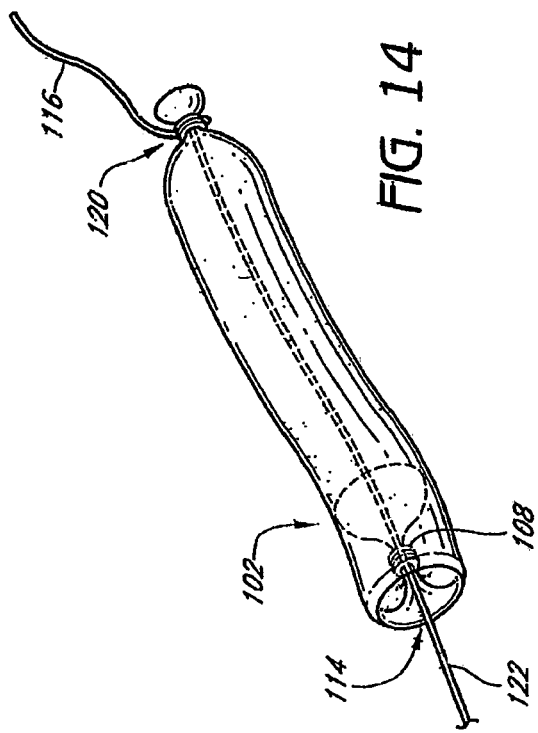
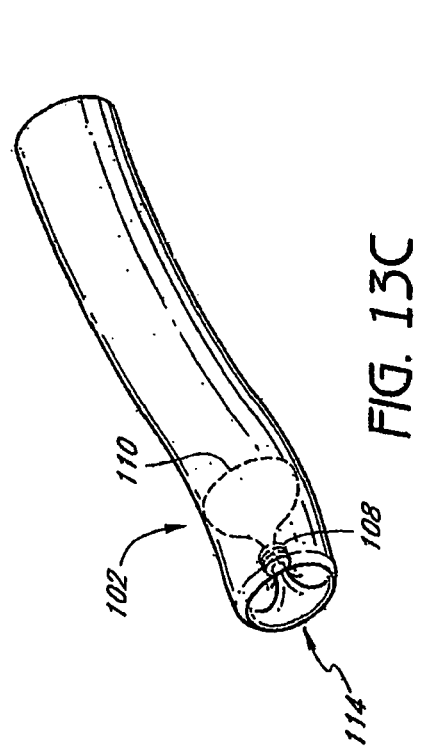
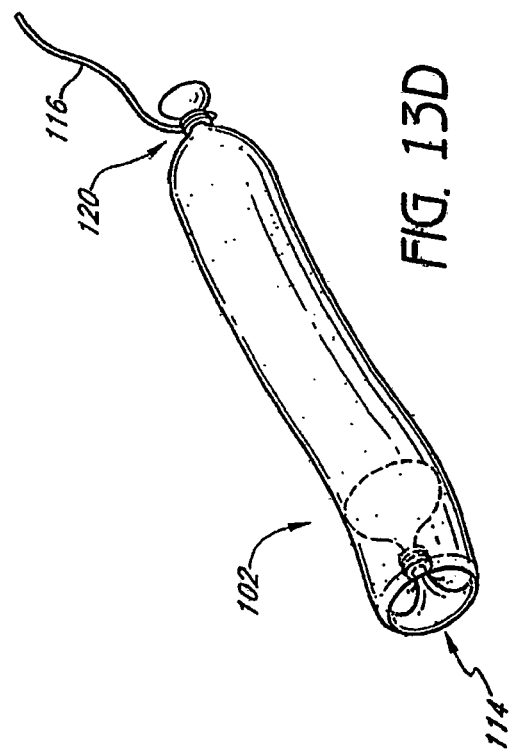

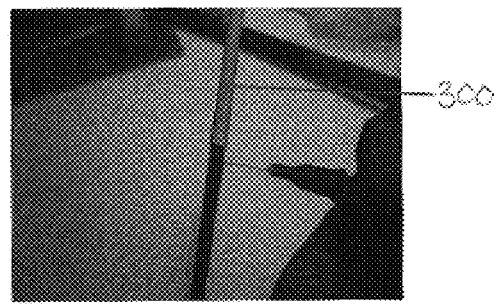
FIG. 26G
FIG. 26H  FIG. 26I  FIG. 26J
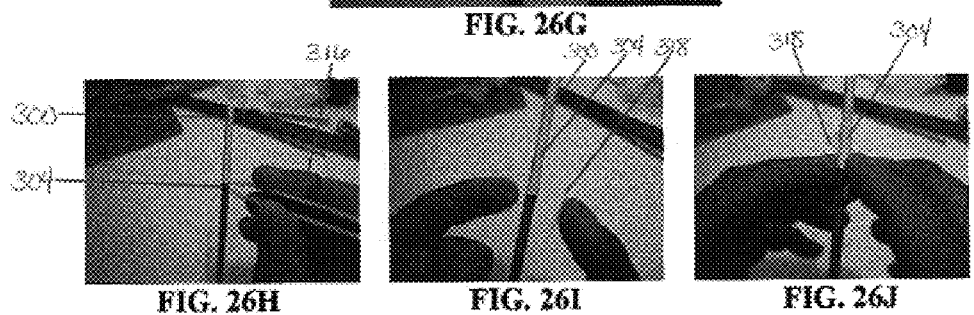
FIG. 27A

US 7,641,688 B2

TISSUE AUGMENTATION DEVICE

CROSS-REFERENCE TO RELATED APPLICATIONS

This is a continuation-in-part application that claims dual priority from U.S. patent application Ser. No. 10/942,728, filed Sep. 16, 2004, now U.S. Pat. No. 7,244,270 issued on Jul. 17, 2007, and PCT/US2005/033252, filed Sep. 15, 2005, the disclosures of which are incorporated in their entirety herein by reference.

BACKGROUND OF THE INVENTION

There is a growing demand for cosmetic procedures which augment soft tissue to enhance facial appearance. The American Society for Aesthetic Plastic Surgery reports nearly 8.3 million aesthetic procedures were performed in 2003, an increase of 20% from the year before. The most common of these procedures are intended to remove facial wrinkles and lines or augment the lips to restore a more youthful appearance.

Botulinum toxin is used to paralyze the small facial muscles around dynamic wrinkles in the forehead and around the eyes. Materials that have been used to smooth non-dynamic wrinkles or augment facial tissues (nasolabial lines, lips, etc.) include injectable soft tissue fillers such as silicone, collagen in a variety of forms and formulations such as Inamed Corporation's CosmoDerm and CosmoPlast, hyaluronic acid derivatives such as Restylene and Hyaloform, and calcium hydroxyapatite microspheres such as Radiance. Autologous fat can also be taken from a donor site by liposuction and then injected in the targeted facial tissue. While these injectable fillers are convenient, and some can even be done as a simple office procedure, the results are temporary and once injected, the filler cannot be removed.

Implanted artificial tissue fillers are well known and are generally placed through surgical incisions. These include ePTFE-based tubes, fibers or sheets, including Gore Subcutaneous Augmentation Material (S.A.M.), Advanta, marketed by Atrium Medical, and Ultrasoft and Softform marketed by Tissue Technologies, now Integra Life Sciences. Surgically implanted tissue fillers can also be derived from biologic sources such as Alloderm from LifeCell Corp. and DuraDerm from Collagensis, Inc.

Surgically implanted fillers have a number of limitations such as prolonged recovery time due to bruising and swelling which is unacceptable to many patients, risk of infection or granuloma formation, erosion, shrinking and migration. Many patients cannot accept the fact the implant is palpable under the skin because it is firmer than the surrounding skin. The implanted fillers may also be difficult to remove, should the patient wish to, or a complication arises that demands its removal.

The ideal facial tissue filler would be completely biocompatible; easy to place through a relatively small needle, as opposed to through a large surgical incision; permanent but could be removed either at the time of the procedure to allow for re-positioning, or at some time in the future; have a very low risk of infection or immunologic response; would not expand, contact or migrate over time; would not erode; and would not be noticeable to the patient.

Biocompatible medical devices that have a small enough profile to fit into a catheter, yet self-expand or are made to expand when such a device is released from the distal end of the catheter, are ubiquitous in vascular, cardiovascular and neurovascular intervention. Such devices include various types and configurations of self-expanding or balloon expandable stents, and embolization coils. These devices are often constructed of a metal and can be covered with a polymer such as a sleeve of ePTFE.

However, there remains a need for a device of a similar nature that can be placed within a non-vascular space such as dermal tissue, which can be enlarged in situ to provide a desired cosmetic or therapeutic result.

SUMMARY OF THE INVENTION

In one embodiment of the present invention, the invention comprises an implantable tissue augmentation device. In one embodiment, the device comprises an elongate, flexible tubular body, having a proximal end, a distal end and a cavity, a valved opening on the proximal end, and a closed distal end. In a preferred embodiment, the device additionally has a first configuration and a second configuration, wherein the tissue augmentation device is transformable from the first configuration to the second configuration by introduction of a filler into the cavity via the valved opening.

In another embodiment of the present invention, the invention comprises a tissue augmentation device having a first configuration and a second configuration, wherein the first configuration is adapted to fit through a tubular access channel and the second configuration is adapted to fill tissue with a tissue augmenting size and shape and wherein the tissue augmentation device is transformable from the first configuration to the second configuration by introduction of a filler into the device following delivery of the device into the tissue through the tubular channel.

In a further embodiment of the present invention, the invention comprises a kit system, or compilation of items for augmenting tissue, comprising at least one tissue augmentation device having an elongate, flexible body, which is transformable from a first configuration for implantation to a second configuration for augmentation; a filler tube for permitting access to the interior of the body; and a filler, for transforming the body from the first configuration to the second configuration.

In yet another embodiment of the present invention, the invention comprises a method of augmenting soft tissue. In one embodiment, the method comprises identifying a treatment site on a patient; introducing a dissecting tool into the tissue beneath the treatment site; creating a tissue plane using the dissection tool; introducing a transformable tissue augmentation device into the tissue plane; and transforming the tissue augmentation device from a first, reduced configuration having a first volume to a second, enlarged configuration having a second volume while at the site. In one embodiment, the second configuration is at least about 5 times greater than the first configuration.

In one or more of the embodiments described herein, the tissue augmentation device further comprises at least one port on the proximal end, for accessing the interior of the body.

In one or more of the embodiments described herein, the tissue augmentation device is transformable from the first configuration to the second configuration upon introduction of a filler through the port and into the device after the device has been delivered into the tissue.

In one or more of the embodiments described herein, the tissue augmentation device comprises material to encourage fibrous tissue ingrowth.

In one or more of the embodiments described herein, the tissue augmentation device comprises at least one grasping means to allow positioning of the device at a desired site. In one embodiment, the grasping means comprises one or more tabs.

In one or more of the embodiments described herein, the tissue augmentation device comprises an inner layer and an outer layer, wherein the outer layer comprises a porous material to encourage fibrous tissue ingrowth and wherein the inner layer comprises an elastomeric material that adds flexibility to the body and is for contact with the filler material.

In one or more of the embodiments described herein, the tissue augmentation comprises at least two layers, wherein an outer layer comprises ePTFE and an inner layer comprises silicone, polyurethane, or a thermoplastic elastomer. In one embodiment, the device comprises only an inner and outer layer. In one embodiment, the device comprises one or more additional layers. In another embodiment, the device comprises only a single layer.

In one or more of the embodiments described herein, the tissue augmentation comprises one or more fluids. The fluid may comprise one or more liquids. The liquid may comprise saline.

In one or more of the embodiments described herein, the filler comprises a material that can be manually shaped to a desired configuration before the filler transforms to retain a molded configuration.

In one or more of the embodiments described herein, the tissue augmentation device permits passage of a fill tube, but reseals either completely or substantially following removal of the fill tube. In one or more of the embodiments described herein, the resealing occurs without any external intervention (e.g., the device spontaneously self-seals).

In one or more of the embodiments described herein, the tissue augmentation device comprises one or more pierceable septums, which permit passage of a fill tube, but which reseal either completely or substantially following removal of the fill tube.

In one or more of the embodiments described herein, the tissue augmentation device comprises a plurality of internal baffles which divide an interior cavity of the device into a plurality of chambers or compartments. The baffles may comprise pierceable septums, which permit passage of a fill tube, but which reseal either completely or substantially following removal of the fill tube.

In one or more of the embodiments described herein, the device comprises two or more compartments that are adapted to be filled separately in order to vary the contour of the filled region.

In one or more of the embodiments described herein, the device is selectively inflated or deflated to achieve a desired contour.

In one or more of the embodiments described herein, the device has a diameter within the range of from about 1 mm to about 8 mm.

In one or more of the embodiments described herein, the device has a length within the range of from about 1 cm to about 6 cm.

In one or more of the embodiments described herein, the device has a wall thickness within the range of from about 0.003 inches to about 0.020 inches.

In one or more of the embodiments described herein, the tissue augmentation device has a second configuration that has a diameter of about 1 mm to about 10 mm.

In one or more of the embodiments described herein, the first configuration of the device is dimensioned to fit through a tubular access channel having a gauge in the range of about 14 gauge to about 20 gauge.

In one or more of the embodiments described herein, the first configuration of the device has a diameter of less than about 1.6 mm.

In one or more of the embodiments described herein, the tissue augmentation device comprises one or more sutures.

In one or more of the embodiments described herein, the tissue augmentation device is adapted to be substantially uninflated prior to insertion into the tissue. In other embodiments, the tissue augmentation device is adapted to be partially inflated prior to insertion into the tissue.

In one or more of the embodiments described herein, filler is added into the tissue augmentation device during the implantation procedure and at least once subsequent to implantation, thereby providing a chronically adjustable tissue augmentation device.

In one or more of the embodiments described herein, the tissue augmentation device is internally segmented to permit the segments to be filled with various volumes of filler material in order to create a specific profile.

In one embodiment of the present invention, a augmentation system is provided. In one embodiment, this system comprises the tissue augmentation device of one or more of the embodiments described herein, and a dissection tool to separate tissue beneath the treatment site and create a tissue plane.

In one embodiment of the present invention, a tissue augmentation system comprising the tissue augmentation device of one or more of the embodiments described herein, and a tubular access channel is provided. In one embodiment, the tubular access channel comprises a needle, cannula or catheter.

In one embodiment of the present invention, a tissue augmentation system comprising the tissue augmentation device of one or more of the embodiments described herein, and a fill tube for providing filler is provided.

In one or more of the embodiments described herein, the tissue augmentation device is for use in the treatment of facial scars, lines, or wrinkles.

In one or more of the embodiments described herein, the tissue augmentation device is adapted to and used for augmenting facial tissue.

In one or more of the embodiments described herein, the tissue augmentation device is adapted to and used for augmenting facial wrinkles.

In one or more of the embodiments described herein, the tissue augmentation device is adapted to and used for filling lines, scars, or wrinkles on the body or face.

In one embodiment of the present invention, a plurality of the tissue augmentation devices is provided. In one embodiment, tissue augmentation devices are provided in a plurality of various sizes so as to permit the user to select a desired size. In one embodiment, at least one of the tissue augmentation devices has an inflated diameter of: 0.5 to 2 mm, 1.5 to 5 mm, 2 to 6 mm, or 2 to 8 mm.

In one embodiment of the present invention, the invention comprises an implantable tissue augmentation device, comprising at least two flexible sheets connected to form a plurality of chambers between them, said chambers being adapted to receive a filler to expand one or more of said chambers to a desired configuration. In one embodiment, the sheets comprise a material capable of being pierced by a tube for supplying filler to the chambers and self-sealing upon withdrawal of such a tube. In one embodiment, the sheets are bonded together adjacent their periphery and between their periphery to form the chambers. In one embodiment, the sheets are bonded together between the peripheries in a grid-like pattern. In another embodiment, two sheets are provided, each sheet being formed of multiple layers. In one embodiment, the periphery is shaped to generally fit the human cheek. In one embodiment, the device, in its pre-filled condition, has a thickness of less than about 15 mm.

In one or more of the embodiments described herein, the device is located in a larger sheet arrangement, from which one or more of the devices may be cut.

In one embodiment of the present invention, the invention comprises a method of augmenting tissue, comprising implanting a device comprising at least two flexible sheets connected to form a plurality of chambers between them, and selectively filling, partially or fully, one or more of the chambers therein to achieve a desired contour in the tissue.

There is provided in accordance with one aspect of the present invention, a tissue augmentation system. The system comprises a tubular channel adapted to be placed within human tissue, and a tissue dilator adapted to pass through the tubular channel. A tissue filling device is provided, having a first configuration and a second configuration. The first configuration is adapted to fit through the tubular channel and the second configuration is formed to fill the tissue. The device is transformable from the first configuration to the second configuration upon introduction of a filler into the device after the device has been delivered into the tissue through the tubular channel.

The tubular channel may be a needle, catheter, cannula, or other access device. The tissue to be augmented may be the skin.

In accordance with another aspect of the present invention, there is provided a tissue augmentation device. The device comprises an elongate flexible body, having a proximal end and a distal end. At least a first port is provided on the proximal end, for accessing the interior of the body. A suture extends from the distal end.

A needle may be provided on the suture, for percutaneous access to a treatment site. The body may comprise a tubular sleeve, which may have a circular or flattened cross section. The body may comprise two sheets of material bound together along a periphery. The body may also comprise two concentric tubular layers. At least a second port may be provided, for accessing the interior of the body. One or more valves may be provided, for closing the port. In certain embodiments, at least two compartments may be provided within the flexible body.

In accordance with a further aspect of the present invention, there is provided a kit for augmenting tissue. The kit comprises at least one elongate flexible body, which is transformable from a first configuration for implantation to a second configuration for augmentation. At least one suture is attached to the body. A filler tube is provided, for permitting access to the interior of the body. The term "filler tube" is used interchangeably with the term "fill tube." A filler is additionally provided, for transforming the body from the first configuration to the second configuration.

The body may comprise a tubular sleeve, which may have one or a plurality of internal compartments. The body may additionally comprise a valve. At least a second suture may additionally be attached to the body. The filler may comprise a liquid, and may be polymerizable in situ. The kit may additionally comprise a syringe, for injecting the filler into the filler tube.

In accordance with a further aspect of the present invention, there is provided a kit for augmenting tissue. The kit comprises a plurality of elongate flexible bodies, each of which is transformable from a first configuration for implantation to a second configuration for augmentation, provided in a plurality of sizes and shapes. At least one suture is attached to each body. A deployment tube is provided, for delivering the body to a treatment site. A filler tube is provided for permitting access to the interior of the body, and a filler is provided, for transforming the body from the first configuration to the second configuration.

In accordance with another aspect of the present invention, there is provided a kit for augmenting tissue. The kit comprises a plurality of elongate flexible bodies, each of which is transformable from a first configuration for implantation to a second configuration for augmentation. The flexible bodies are provided in a plurality of sizes and shapes. At least one suture is attached to each body. A filler tube is provided for permitting access to the interior of the body, and at least two different fillers for transforming the body from the first configuration to the second configuration are also provided. The fillers may have different viscosities, and/or different durometers.

There is provided in accordance with one aspect of the present invention, a method of filling tissue. The method comprises the steps of inserting a tubular channel within the tissue, and inserting a tissue filling device into the channel. The tubular channel is withdrawn over the tissue filling device, to leave the tissue filling device within the tissue. The device is transformed to reconfigure the tissue.

The tubular channel may comprise a needle, a cannula, or other access device. The tissue may be the skin.

The transforming the device step may flatten the nasolabial fold. The transforming the device step may alternatively enhance the lips.

In accordance with a further aspect of the present invention, there is provided a method of filling tissue. The method comprises the steps of inserting a needle into the tissue, and passing a guidewire (e.g., suture, metal filament, etc.) through the needle. The needle is removed, and a catheter is passed over the wire. A tissue filling device is inserted through the catheter, and the catheter is withdrawn over the tissue filling device thereby leaving the tissue filling device within the tissue.

In accordance with a further aspect of the present invention, there is provided a method of filling tissue. The method comprises the steps of inserting a needle containing a tissue filling device into the tissue. The tissue filling device is maintained in substantially constant position relative to the tissue via forward pressure on a system component in contact with the device such as a filler tube, while the needle is withdrawn over the tissue filling device, thereby leaving the tissue filling device within the tissue. The tissue filling device is filled by injecting filler material through the filler tube into the tissue filling device, and the filler tube is removed. The tissue may be the skin.

In accordance with a further aspect of the present invention, there is provided a method of augmenting soft tissue. The method comprises the steps of identifying a treatment site on a patient, and introducing a transformable tissue bulking device beneath the site. The bulking device is transformed from a first, reduced volume to a second, enlarged volume while at the site.

The introducing step may comprise introducing the device over a wire. The introducing step may comprise introducing the device through a tube. The introducing step may comprise pulling a distal end of the device with a distal suture.

The transforming step may comprise introducing a filler into the device. The identifying step may comprise identifying a wrinkle. The site may comprise a nasolabial fold, an upper lip, a lower lip, a facial fold, or other site where tissue bulking is desired.

In accordance with a further aspect of the present invention, there is provided a method of augmenting soft tissue. The method comprises the steps of identifying a treatment site on a patient, and measuring the dimensions of the site. A tissue bulking device having a size and shape appropriate to the dimensions of the site is chosen from a kit of transformable tissue bulking devices. The chosen transformable tissue bulking device is introduced beneath the site, and the device is transformed from a first, reduced volume to a second, enlarged volume while at the site. The measuring step may comprise passing a suture or other measurement device containing a plurality of markings along the path to be augmented and counting the number of or reading the markings.

In accordance with a further aspect of the present invention, there is provided a method of augmenting soft tissue. The method comprises the steps of identifying a treatment site on a patient, and introducing a transformable tissue bulking device beneath the site. A polymer is injected into the tissue bulking device, and the tissue bulking device is shaped in situ (e.g., by manual manipulation of the surface of the skin, application of a mold, etc.) into a desired configuration. The polymer is then caused (e.g., permitted, or actively catalyzed or initiated by application of an external initiator) to retain the desired configuration.

In accordance with a further aspect of the present invention, there is provided a method of augmenting soft tissue. The method comprises the step of identifying a treatment site on a patient, and introducing a dissection tool into the tissue beneath the treatment site. A tissue plane is created using the dissection tool, and a transformable tissue bulking device is introduced into the tissue plane. The bulking device is transformed from a first, reduced volume to a second, enlarged volume while at the site.

In accordance with a further aspect of the present invention, there is provided a method of augmenting soft tissue. The method comprises the steps of identifying a treatment site on a patient, and introducing a tissue filling device into the tissue beneath the treatment site. A filler material is injected into the tissue filling device, while the contour of the treatment site is monitored. Once the treatment site has achieved a desired contour, injection of filler material is discontinued.

In accordance with a further aspect of the present invention, there is provided a method of augmenting soft tissue. The method comprises the steps of identifying a treatment site on a patient, and measuring the dimension of the site. A transformable tissue bulking device having a size and shape appropriate to the dimensions of the site is selected from a kit having a plurality of tissue bulking devices. The elasticity of the tissue at the treatment site is assessed, and a filler of a consistency appropriate to the elasticity of the treatment site is selected from a kit including a plurality of fillers. The selected transformable tissue bulking device is introduced beneath the site, and transformed from a first, reduced volume to a second, enlarged volume while at the site.

There is provided in accordance with one aspect of the present invention, a method of making an implantable tissue bulking device. The method comprises the steps of providing a flexible tubular body, having a proximal end, a distal end and a central lumen. A closing element is positioned on the proximal end of the tubular body, and the tubular body is everted to position the closing element within the central lumen.

The closing element may comprise one or more elastomeric bands, a suture, a clip, or other biasing element.

The method may additionally comprise the step of tying a suture or positioning another closing element around the distal end of the tubular body, to form a closed distal end. The method may additionally comprise the step of positioning a guidewire through the proximal end and into the central lumen.

There is provided in accordance with another aspect of the present invention, an implantable tissue augmentation device. The device comprises an elongate flexible tubular body, having a proximal end, a distal end and a central lumen. A valved opening is provided on the proximal end, and the distal end is closed.

The device may additionally comprise a guidewire extending through the valved opening. The valve may comprise a closing element surrounding a portion of the tubular body. The tubular body may be everted to position the closing element within the central lumen. The closing element may comprise a suture loop. Alternatively, the closing element may comprise an elastic loop, or a metal loop. The device may additionally comprise a distal suture attached to the distal end of the tubular body.

There is provided in accordance with one aspect of the present invention a tissue filling device. The device has a first configuration and a second configuration, wherein the first configuration is adapted to fit through a tubular access channel and the second configuration is adapted to fill tissue with a tissue augmenting size and shape. The device is transformable from a first configuration to the second configuration by introduction of a filler into the device following delivery of the device into the tissue through the tubular channel.

The device may comprise a flexible polymeric tube. The filler may comprise shape memory wire, a plurality of coils, a liquid, a gel, or beads suspended in a liquid. The filler may be polymerizable in situ, cross linked in situ, or otherwise change viscosity in situ. The device may have proximal and distal ends that are softer than a mid-portion, and may comprise a balloon. The device may be at least partially covered with a polymer, such as ePTFE, or a laminate of ePTFE and a thermoplastic. The thermoplastic may be polyethylene.

The device may comprise a metallic frame, such as Nitinol frame, having a polymer coating.

The tubular channel may be a needle, a catheter, a cannula or other access device.

The tissue may be the skin, the gastroesophageal junction, the myocardium or the stomach wall. The tissue may also be in the vicinity of the nasolabial fold, the right or left or both sides of the upper or lower lip, the cheeks, other facial folds, or other site on the body where augmentation is desired.

BRIEF DESCRIPTION OF THE DRAWINGS

FIG. 1 is a schematic side elevational cross section through an empty sleeve in accordance with one embodiment of the present invention.

FIG. 2 is a side elevational cross sectional view through a partially inflated sleeve.

FIG. 3 is a side elevational cross sectional view through a filled sleeve having a uniform exterior profile.

FIG. 4 is a cross sectional side elevational view through a segmented sleeve, having customized fill volumes in each segment.

FIG. 5 is a cross sectional view through the distal end of an implant, illustrating a filler tube in position to fill a single segment.

FIG. 6 is a side elevational cross sectional view through a segmented sleeve having a plurality of internal baffles.

FIG. 7 is a side elevational schematic view of a filler tube in accordance with one embodiment of the present invention.

FIG. 8 is a side elevational view of an implant removably attached to a filler tube.

FIG. 9 is a side elevational schematic view of the implant of FIG. 8, positioned beneath the skin.

FIG. 10 is a side elevational view of an implant removably attached to a filler tube.

FIG. 11 is a side elevational schematic view of the implant of FIG. 10, positioned beneath the skin.

FIG. 12 is a side elevational schematic view of an implant and filler tube assembly, positioned within a delivery cannula.

FIG. 13A through 13D illustrate an assembly sequence for a soft tissue bulking device in accordance with one embodiment of the present invention.

FIG. 14 illustrates a bulking device as in FIG. 13D, additionally showing a guidewire.

FIG. 18A illustrates the configuration of a tube-based, taut-filled implant. FIG. 18B shows a tube-based, slightly flaccid implant. FIG. 18C shows a tube-based markedly flaccid-filled implant. FIG. 18D shows a sheet-based, taut-filled implant. FIG. 18E discloses a sheet-based, flaccid filled implant. FIG. 18F shows an example of a sheet-based implant with two sheets of differing compliances, that may be desirable in order to make an asymmetric cross-section upon inflation.

FIG. 23B illustrates an embodiment of an implant with variations in lamination, in which the porous outer material is affixed to the underlying elastomeric material in wound or interrupted configurations, for example, helical, bands, stripes, and the like.

FIG. 26G illustrates a step in creating an implant lamination subassembly by application of adhesive to the silicone tube, according to one embodiment of the invention.

FIG. 26H illustrates a step in creating an implant lamination subassembly where ePTFE is everted over the silicone tube using tweezers, according to one embodiment of the invention.

FIG. 26I illustrates a step in creating an implant lamination subassembly immediately prior to the application of tape to evert the ePTFE over the silicone tube, according to one embodiment of the invention.

FIG. 26J illustrates a step in creating an implant lamination subassembly where tape is applied to evert the ePTFE over the silicone tube, according to one embodiment of the invention.

FIG. 27A illustrates various components required to create an implant valve subassembly, according to one embodiment of the invention.

DETAILED DESCRIPTION OF THE PREFERRED EMBODIMENT

Figure 15:
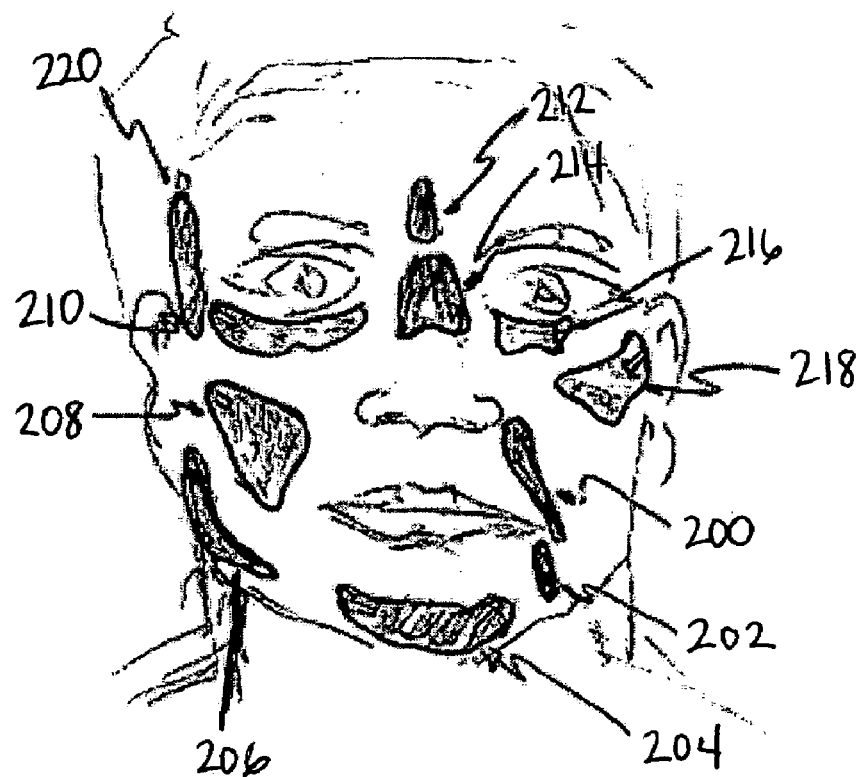
FIG. 15 depicts non-limiting examples of potential locations for implants on the face.

The invention is, generally, a system and method for volume augmentation of tissue in a living being, preferably, a human. The system generally comprises a tissue-filling device and a method for delivering the tissue-filling device into tissue. The tissue-filling device comprises tissue filler material and an enclosing sheath. Preferably, the enclosing sheath forms a container that is filled.

The volume augmentation methods and devices described in embodiments of the present patent are intended to be used for tissue bulking in a variety of circumstances, depending on the need. For example: in gastroenterology, wherein increasing the volume of tissue at the gastro-esophageal junction can be used to treat gastro-esophageal reflux disease, and increasing the thickness of the gastric mucosa to decrease the volume of the stomach to treat morbid obesity; in urology, where placing filler radially around the urethra at the neck of the urinary bladder can ameliorate incontinence; and in cardiology, whereby tissue filler may be placed in the ventricular wall to decrease the volume of the left ventricular chamber to treat heart failure, or in the pericardial space to place pressure on the outside of the heart, also intended to decrease the volume of the heart chambers and thereby treat heart failure; and in other applications well known to those skilled in the art. In any of these clinical applications, the tissue-filling device may be combined with any number of other bioactive substances which may be released from the filler itself over time, or be injected concurrently.

One preferred use of the present invention is in the field of cosmetic plastic surgery wherein the system is used for augmentation in the dermis or subdermis to treat skin contour deficiencies caused by various conditions, including aging, environmental exposure, weight loss, child bearing, surgery, disease such as acne and cancer, or combinations thereof, or for beauty enhancement. The tissue augmentation method of preferred embodiments of the present invention is particularly suitable for treating frown lines, worry lines, wrinkles, crow's feet, facial scars, or marionette lines, or to augment facial features such as the lips, cheeks, chin, nose or under the eyes. Treatment of a patient may consist solely of using a tissue-filing device, or the tissue-filling device may be used as part of additional cosmetic surgery such as a face or brow lift. The characteristic of change from first configuration to second configuration makes the tissue-filling device desirable for use in endoscopic surgery. The tissue augmentation device may also be used for breast augmentation, and regions of the body that need volume enlargement during reconstructive plastic surgery, such as after trauma or tumor resection.

The sleeve can be embodied as a variety of structures, and constructed of a variety of materials. The term "sleeve" as used herein is meant to include any structure adapted to substantially separate a filler material from the tissue in which the tissue-filling device is implanted. The term "skin" and "membrane" is used interchangeably and has the same scope of meaning as sleeve.

In one embodiment, a sleeve is placed in the tissue to be filled, and as a second step, the sleeve is filled with material such that the sleeve, when filled, creates a volume adequate to alter the tissue contour as required to produce the clinical result. Filling can either be accomplished through the device used to implant the sleeve, or through a separate device, or both, as will be discussed. In an alternative embodiment, the tissue-filling device is constructed prior to its implantation in the tissue by filling a sleeve with a tissue filler and the assembled tissue-filling device is placed in the tissue. In still another alternative embodiment, the tissue filler may be of more than one component such that one (or more) component of the tissue filler is in place inside the sleeve before the sleeve is placed in the tissue to be augmented, and a second component (or components) are placed within the sleeve after the sleeve has been placed in the tissue, the combination of the components than constituting the final filler material.

The sleeve can be compliant or non-compliant, or a combination of compliant and non-compliant components. The sleeve may be made of a biocompatible but non-biodegradable material. Suitable materials include ePTFE, PTFE, polypropylene, polyacrylamide, polyurethane, silicone, polymethylmethacrolate, Dacron, metals, tubes or meshes of nickel titanium alloys such as Nitinol, silver, gold, platinum, or stainless steel. The sleeve can comprise a plurality of layers of materials. Other biocompatible materials are well known in the art, as, for example, disclosed in U.S. Pat. No. 5,630,844 to Dogan.

If fibrous tissue ingrowth is desired, then the sleeve can be made of or covered with ePTFE with a pore size of in the range of from about 40 to about 100μ. If the filler material is, or becomes, non-flowable, the sleeve may be made of a biocompatible and biodegradable material chosen from any of various polylactides, polyglycolides, polycaprolactones, polyanhydrides, polyamides, polyurethanes, polyesteramides, polyorthoesters, polydioxanones, polyacetals, polyketals, polycarbonates, polyortho-carbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or higher poly-monomer polymers thereof or combinations or mixtures thereof, such that the initial implantation of the filler device comprises a sleeve and filler material, but over time, the sleeve is resorbed and only the filler material is left behind to augment the tissue.

In one embodiment, the sleeve comprises an outer layer of ePTFE of about 40 to 100μ pore size and about 0.001 to 0.010 inches in thickness to encourage fibrous tissue ingrowth, and an inner sleeve of polyethylene or similar material of about 0.001 to 0.010 inches in thickness to add flexibility to the sleeve and to more completely contain the filler material. Such double layer structure is particularly suited where the ePTFE is permeable or semipermeable to the filler material, such as when the filler material is, or contains a component of, water.

The sleeve may contain, or be contained by, a skeletal structure such as struts of a metal including alloys such as nitinol, stainless steel, gold, or platinum, a polymer such as PLA or PLG, or any material of sufficient durometer or structural integrity to provide support of the sleeve or to provide for a three-dimensional shape. Struts can extend in an axial direction, a circumferential direction or both depending upon the desired clinical performance. Additionally, the struts may have anchor elements or hooks which extend through the sleeve, adapted to stabilize the tissue-filling device within the tissue.

In one embodiment, the sleeve itself is highly flexible. Therefore, the material should be thin, such as within the range of from about 0.001 inches to about 0.010 inches. The sleeve may be manufactured to be of fixed length and shape, with a plurality of lengths and shapes provided in a kit, depending on the need to fill a specific region of tissue in a particular patient, or the sleeve may be cut to size at the clinical site as a part of the implantation procedure. For a given region to be filled, more than one tissue filling device may be placed to achieve a given desired contour. In one embodiment, a plurality of sleeves are provided that are bound together to create a bundle.

The tissue-filling device may be provided in a kit which includes one or more sleeves, and one or more filler materials. Or the sleeve may be supplied separately in a kit, and another kit includes one or more filler materials. Or the kit may consist solely of one or more sleeves, and the surgeon provides the filler material from an alternate source.

The sleeve may have a constant inflated diameter, generally 1-10 mm, or it may have an inflated diameter that varies along its length depending on the desired contour of the augmented tissue. For glabellar folds, the inflated diameter is, preferably, 0.5 to 2 mm. For lips, the inflated diameter is, preferably, 1.5 to 5 mm. For the upper lip, the inflated diameter preferably varies along its length adapted to form the "m" shape of the upper lip. For the lower lip, the sleeve generally tapers at the proximal and distal end, with a larger diameter of 2 to 8 mm at the central portion. In addition, for the lower lip, the profile of the sleeve will be generally a flattened "u" shape adapted to follow the profile of the lower lip. For nasolabial folds, the inflated diameter is, preferably, 2 to 6 mm, with tapering at the proximal and distal ends. In one embodiment, the sleeve comprises a series of segments such that the internal diameter of each segment is greater than the internal diameter of that portion of the lumen between segments. Further, the sleeve may have internal segmentation embodied by a series of valves or baffles. In the case of a segmented sleeve, each segment may be filled with a different volume of filler material in order to create a profile customized along the axial length of the implant to suit the specific clinical need. The sleeve may have supporting struts, such as a skeleton made from filaments, where said filaments may be composed of any biocompatible material adapted to provide structure.

A valve, or a plurality of valves, can be affixed to one or both ends of the sleeve, or along any portion of the wall of the sleeve, in order to prevent filler material from escaping into the surrounding tissue. The required integrity of the valve is dependent on the type and viscosity of the filler material. For example, if the filler material gels in place, or the filler is composed of beads of sufficient size, then the valve may not need to close tightly. In one embodiment, the valve is one or more elastomeric bands that encircles the proximal end of the sheath. In another, the valve is one or more elastomeric bands placed, during construction of the tissue filling device, 1 to 4 mm, distal from the proximal end of the sheath, and then when the sheath is turned inside out during its construction, the valve is placed on the interior portion of the sleeve, enhancing the ability of the valve to remain closed as the sleeve is filled with filler material. In another, the valve is a band of nitinol adapted to form a spring closure at the proximal end of the sheath. Other valves known in the art include, for example, U.S. Pat. No. 5,779,672 to Dormandy or U.S. Pat. No. 6,102,891 to van Erp. In addition to valve placement at the proximal end of the sheath, valves may be deployed at a plurality of locations within the sheath to form segments, which then allows individual segments to be filled with different amounts of filler material.

The filler material can be any of a number of biocompatible substances and may be of various physical states or combinations thereof, such as a non-viscous liquid, a viscous liquid, a gel, a powder, beads, flakes, continuous or discontinuous fibers, coils, fiber balls or mixtures thereof. The filler material may be transformable from a first state to permit introduction into the sheath, to a second state once inside the sheath. Combinations, such as a fiber carried within a liquid or gel are well within the contemplated scope. For example, the filler can comprise a substantially linear filament which itself can be made of a variety of materials such as nitinol, various biocompatible polymers well known to those skilled in the art, ePTFE, Proline or any biocompatible material with adequate strength to alter the contour of the tissue in which it is injected. The filler material may comprises any of a number of materials commercially available and sold as tissue fillers, such as Zyplast™, available from Inamed Aesthetics; Restylane™, available from Q-Med and Genzyme, Inc.; Hylaform™, available from Inamed Aesthetics; Artecoll™ available from Artes, Inc.; Radiance™ available from Bioform, Inc.; or Sculptura™ PLA filler available from Aventis, Inc.

Other embodiments of the filler material include a flexible random or regular coil; knit fibers; woven fabric; a series of filaments wound around each other, a compressible or non-compressible sponge material, a closed or open cell foam, or any others depending on the specific need as is well known to those skilled in the art. The filler material could be a set of objects connected with a outer membrane or an axial filament, or could be a series of discrete objects. If it is desired that the tissue-filling device be visible by x-ray or fluoroscopic imaging, then radio-opaque coatings such as triazoate, barium salts or tantalum can be included in the filler material. If ultrasonic visualization is required, small trapped air bubbles or other echocontrast material can be included in the filler material. The filler material may contain a colored dye in order to render the tissue filling device less visible from outside the tissue.

One class of fillers comprises a mix of solid particles and a carrier. One solid particle comprises micronized particles of ePTFE. Other materials that are suitable for use in the present invention include, but are not limited to, PDS II (polydioxanone, a monofilament), Nurolon (a long chain aliphatic polymer Nylon 6 or Nylon 6, 6) Ethilon (a long chain aliphatic polymer Nylon 6 and Nylon 6, 6), Prolene (Polypropylene, isotactic crystalline stereoisomer of polypropylene, a synthetic linear polyolefin), Vicryl (copolymer made from 90% glycolide and 10% L-lactide), silk, Monocryl (poly-E-caprolactone), polylactide, polyglycolide, poly lactide-co-glycolide, Medpor (biocompatible (micronized) polyethylene), BIOGLASS (bioactive glass particulate), or polyhydroxyvalerate.

Carriers that may be suitable for use in the present invention either alone, as a filler, or in combination with particles include, but are not limited to, polyvinylpyrrolidone (PVP), silicone oil, vegetable oil, saline, gelatin, collagen, autologous fat, hyaluronic acid, autologous plasma, $CO_2$ or other gas, and other physiological carriers.

Another class of fillers includes liquids, gas or gels without discrete solid particles. For example, PVP may be used alone or in combination with other agents. PVP is a water-soluble polyamide that possesses unusual complexing and colloidal properties and is physiologically inert. PVP is commercially available as a biocompatible gel that is freely transported through the body and is excreted unchanged by the kidneys. This gel has trade names such as Au24k and Plasdone C-15 and Plasdone C-30, and comprises macromolecules from the plasdone family, having the empirical formula $(CHCH_2)_2N(CH_2)_3$—CO. Polymers of this family have been used as binders, extenders, and vehicles for a variety of medications for nearly fifty years, and would be expected to be well tolerated and quickly removed from the body in the event of a valve failure, if the sleeve were to rupture or leak, or if material were mistakenly injected into the tissue, rather than into the sleeve, during the implantation procedure.

PVP is available commercially in many molecular weight ranges and is polymerized to have an average molecular weight in a particular solution. For example, PVP is available in solutions of an average molecular weight of 10,000 daltons, 40,000 daltons and 360,000 daltons. Preferably, the PVP is less than about 60,000 daltons to allow for easier renal excretion. PVP is also defined by its viscosity measurement, or K value. K values range from approximately less than 12 to 100. PVP compositions which may be desirable with the present invention are within a range of K values of from about 12 to 50. PVP is commercially available from International Specialty Products, Inc., GAF Chemical Corp., Wayne, N.J., USA, and from BASF Aktiengesellschaft, Germany. In use, the gel polymer may be diluted with deionized water or saline to produce the desired viscosity, is sterilized, and placed in cartridges for injection. Alternatively, the dehydrated polymer particles may be placed within the sleeve prior to its being placed in the tissue to be augmented, and sterile saline added after the sleeve has been placed, resulting in gel formation within the sleeve, and thence expansion of the tissue. Alternatively, the dehydrated polymer particles may be supplied in a sterile container and reconstituted with saline or water just prior to filling the sleeve.

Once the filler material is inside the sleeve, its material state or chemical structure may be altered via a number of mechanisms, such as the addition of a second material acting as a catalyst, heat or cold, change in pH, ultrasound or light, or the state change may happen spontaneously over a period of time. If the material changes its state over time, that time would ideally be in the range of 10 to 30 minutes from injection so that the clinician can mold the shape by manual palpation to a desired configuration before the filler transforms to retain its molded configuration. Alternatively, the state change would take place over 24 to 48 hours so the patient can sculpt his or her own filler configuration. In one embodiment, the filler material is a biocompatible polymer which fills the sleeve in a relatively flowable state, is molded from the skin surface by the operator to the desired shape, then light of the appropriate wavelength (e.g., UV) is directed at the skin in order to convert the liquid to a non-flowable gel, which gel retains the desired suppleness. In one embodiment, the gel comprises a backbone of PEG and/or PVA, with PLA and/or PLG side groups attached to allow for biodegradability of any gel which fails to fill the sleeve or leaks out, and methylacrylates subunits attached to the backbone to induce photopolymerization with light of wavelength about 400-500 nm.

The filler material may be capable of reversing its state change, via any of the mechanisms describe above, to allow for subsequent removal of the filler material by aspiration via a channel placed in the sleeve from outside the tissue. In one embodiment, the channel is a needle which contains or is surrounded by an ultrasound crystal such that when the needle is inserted into the sleeve and energy is supplied to the ultrasound crystal, causing it to vibrate in the range of 100 khz to 1 megahertz, the gelled filler material is broken down into a flowable material allowing for aspiration through the needle.

In another embodiment, the filler material comprises a purified protein such as available from Gel-Del Technologies and described in U.S. Pat. No. 6,342,250 and U.S. Patent Application Nos. 20030007991, 20020106410, and 20020028243, which turns into a gel at body temperature and can be changed back into a flowable liquid by application of cold.

In another implementation of the invention, the tissue filling device comprises a sheath and a volume of internal foam. In this embodiment, a valve may not be required, since the foam structure itself acts to prevent filler from escaping from the sleeve. The foam may be a structure having an open or closed cell configuration. In one embodiment, the foam is a closed cell elastomer that is highly compliant, and the sheath is one of the materials noted above. The foam may be biocompatible polyurethane. The sheath may be ePTFE which is bonded to the outside of the foam. In use, the tissue filling device is placed in the tissue either directly or via the pull through sewing method previously described. Once in place, the tissue filling device is injected from a site or sites externally to the tissue to be filled, such as from the surface of the skin, with a fluid, such as water, saline, silicone, a hydrogel, or any of the filler materials described above including combinations of solid or gel particles or filaments within the fluid carrier. Preferably, a small hollow structure is used to inject the filler material, such as a 25-32 gauge hypo-tube or needle.

This results in local enlargement of the tissue filling device as the closed cell foam is filled in the region in which the filler is injected. Additional sites along the tissue filling device are injected in order to customize the shape of the augmentation. If too much filler has been injected in a region, filler can be removed by re-entering the region that needs to be shrunk, and then withdrawing filler. The entry of the hypo-tube or needle into the region that needs to be shrunk can be via the same route through which the region was filled, or another pathway may be taken, such as through the skin generally perpendicularly to the axis of filling. Thus, in one embodiment, a device according to any of the embodiments described herein is selectively inflated or deflated to achieve a desired shape or contour. Alternatively, additional filler material can be added during the procedure, or at any later time as desired.

Thus, in one embodiment, filler material is added into a device (according to any of the embodiments described herein) during the implantation procedure and, optionally at least once subsequent to implantation. In another embodiment, the device is adapted to be at least partially inflated two or more times after insertion into the tissue, thereby providing a chronically adjustable device. In one embodiment, the device is implanted and inflated (e.g., filled) in one procedure or on the same day, and adapted to be further inflated (e.g., filled) on another day. These embodiments are particularly advantageous because they offer the recipient the ability to fine tune the contour and appearance of the augmentation.

The foam body is thus constructed of a cellular foam matrix having a multiplicity of cells which divide the interior volume of the implant into compartments numbering from 100 to 1,000,000 depending on the filler material chosen and the desired feel of the filled tissue. The cellular foam material may be a thermoset or thermoplastic polymer. Preferably, the cellular foam material has elastomeric qualities but may be of a non-elastomeric polymer foam. The shape of the foam body influences the basic range of shapes of the implant and for many wrinkle applications will be an elongate body having in an uninflated configuration a length of at least about 5 times and often at least about 20 times its average un-inflated cross section. The particular material or materials chosen for constructing the foam body will depend, at least in part, on the density or hardness of the tissue to be simulated.

In certain implementations, the foam body may have an "open-cell" structure, the cells being interconnected with one another by passages that permit intercellular communication of the fluid filler. The passages interconnecting the cells 20 allow the flow of fluid filler from cell to cell, which may create a hydraulic cushioning effect upon localized deformation of the implant by external pressure. The hydraulic cushioning effect created by intercellular fluid communication may help to impart realistic shape and tissue-like consistency to the implant. The viscosity of the filler at body temperature is preferably related to the passage size to inhibit excessive free flow between cells in the absence of external pressure.

The foam body may have a uniform cellular density throughout, or may have a cellular density that varies throughout one or more regions, i.e., a cellular density gradient. In the case of an embodiment that includes one or more regions 30, 32 having a cellular density gradient, the regions 30, 32 will have different average cellular densities. The average cellular density of a region can be selected to cooperate with the viscosity of the filler to influence the response of the implant to external pressure.

In another embodiment, the open cell structure may be placed within a courser closed cell structure, such that the open cell foam is compartmentalized into regions such that filler remains in a given region, and each region may be filled separately in order to vary the contour of the filled region. In one embodiment, the device according to any of the embodiments described herein, is compartmentalized and adapted to be filled separately in order to vary the contour of the filled region. In some embodiments, certain compartments are left unfilled or partially filled, and may be filled at a later date to achieve or alter a particular shape or contour.

The sleeve for the foam filled embodiment may comprise any of the materials identified previously, as well as linear aliphatic polyether urethane; linear aliphatic polyester urethane; cyclic aliphatic polyether urethane; cyclic aliphatic polyester urethane; aromatic polyether urethane; aromatic polyester urethane; polybutylene; polypropylene; crosslinked olefinic elastomers; styrene-ethylene/butylene-styrene block copolymer; or any other biocompatible material which is substantially radiolucent under standard mammographic or other imaging protocols and intensities. The fluid filler may comprise a biocompatible triglyceride, serum, saline solution, or another biocompatible material which is substantially radiolucent under standard mammographic protocols and intensities.

The foam body may also be made of a material which is substantially radiolucent under standard mammographic or other imaging protocols and intensities. The foam body may be constructed of styrene-ethylene-butylene-styrene copolymer; polyethylene; polyurethane; and polytetrafluoro-ethylene; or another biocompatible material which is substantially radiolucent under standard mammographic or other imaging protocols and intensities.

Coatings can be applied to all or a portion of any of the sleeves disclosed herein, either on the outside or the inside thereof. Methods of applying coatings to biocompatible substances are well known in the art. See, for example, U.S. Pat. No. 6,660,301 to Vogel, U.S. Pat. Nos. 6,368,658, and 6,042,875. The formation of and coating with hydrogels is disclosed in U.S. Pat. No. 6,652,883 to Goupil. Coatings that make the sheath sticky such as fibronectin or vitronectin or laminin can be used if desired to inhibit movement of the sheath relative to the tissue. If it is desired that the sheath be visible by x-ray or fluoroscopic imaging, then radio-opaque coatings such as triazoate, barium salts or tantalum can be used on the sheath.

Coatings can also be applied with a biologically active or therapeutic effect, as needed in the clinical application. For example, growth factors such as fibroblast growth factor, anti-inflammatory agents such as corticosteroids to reduce the amount of fibrosis, antibiotics to reduce the risk of infection on the implant, and anesthetics such as lidocaine, procaine or marcaine to decrease pain. In order to modulate fibroblast proliferation, TNP-470, a potent angiogenic inhibitor, can serve as a coating or a co-injectate. Alternatively, it may be desirable for the sheath to be coated with a tissue adhesive, such as Dermabond™, available from Ethicon/Johnson and Johnson, Inc.; or Focalseal™, available from Focal, Inc. to decrease the motion of the tissue implant device relative to the tissue. This is important since relative motion can prevent proper healing and anchoring of the device to the tissue which could eventuate in erosion. In one embodiment, the sheath is constructed of expanded polytetrafluoroethylene coated with fibrin glue containing fibroblast growth factor 1 (FGF1) and heparin.

Generally, the means for filling the sheath is provided by one or more substantially tubular structures adapted to be placed within the sheath during filling, and removable after the sheath has been filled to the desired volume. In one embodiment, the filler tube can be replaced in the sheath after its removal. The filler tube can comprise a variety of tubular structures, depending on the need, including a needle, a compliant or non-compliant plastic tube, or a metal hypotube comprised of stainless steel, nitinol, or any of a variety of materials as appropriate in view of the structure of the implant and desired filling protocol. The tube may have a variety of cross sectional profiles including round, oval, and flattened, depending on the clinical need and the shape of the sleeve to be filled.

In one embodiment, the tissue filling device is constructed and used as follows. The sheath has a proximal end and a distal end. A guide rail, which has a distal end and a proximal end, is adapted so that its distal end extends beyond the distal end of the sheath, then extends through and within the sheath from distal end to proximal end, and then emerges from the proximal end of the sheath such that the proximal end of the guide rail is proximal to the proximal end of the sheath. The guide rail is of small diameter, preferably 0.1-1.0 mm, and can comprise any appropriate filamentous material such as absorbable or non-absorbable suture, a metal such as stainless steel or nitinol, or any material or combination of materials adapted to allow a filler tube to slide over the guide rail and into the interior of the sheath. The guide rail may be coated with a material such as a hydrogel, silicone, ePTFE or PTFE to increase its lubricity.

A sew-through method of implanting the tissue filling device is as follows. A sewing needle is attached to the distal end of the guide rail using any of a number of methods as are well known in the art. The sewing needle can be straight or curved, and of small diameter, preferably 0.1-1.0 mm. Where the guide rail engages the distal end of the sleeve, the sleeve is substantially bonded to the guide rail such that filler material cannot escape from the distal end of the sleeve. The guide rail then remains unattached to the sleeve. The filler tube and attached syringe is adapted to ride over the guide rail in order for the filler tube to be placed in the sleeve, and removed therefrom after the sleeve has been filled.

In use, the surgeon measures the length of the path he wishes to fill and picks the sleeve assembly of the appropriate length from a kit of such sleeves. The sewing needle is placed by the surgeon into the skin along the path that he wishes to augment, stopping before the distal end of the sleeve emerges from the skin, and taking care that the proximal end of the sleeve is within the tissue. If it is not, the sleeve may be pulled all the way through the tissue from the distal end, thus removing it completely from the tissue. In this case, the surgeon may chose a sleeve of a different length, or may chose to enter the tissue with the sewing needle at a more proximal location, so that the entire sleeve ultimately lies within the tissue. The surgeon may put manual traction on the tissue in order to guide the needle along the desired path. The filler tube is advanced along the guide rail into the interior of the sleeve until the distal end of the filler tube is located at or near the distal end of the sleeve. A syringe with filler material is slid over the guide rail and attached to the proximal end of the filler tube. The surgeon then ejects filler material into the filler tube and thence into the sleeve. He can withdraw the filler tube along the length of the sleeve until an adequate tissue augmentation profile is achieved. The filler tube is then removed from the sleeve along the guide rail, allowing the valve at the proximal end of the sleeve to close. If more augmentation is desired, the filler tube may be again passed over the guide rail, through the valve and into the sleeve, where more filler material may be deposited. When the desired amount of filler material is within the sleeve, the filler tube is removed and the guide rail is cut flush with the skin at the proximal and distal ends of the sleeve. That portion of the guide rail within the sleeve remains there after the distal and proximal ends are cut.

In an alternative embodiment, one or more stay sutures may also be attached to the proximal end of the sleeve. In use, the stay suture extends from the proximal end of the sleeve and out to the external aspect of the tissue. The surgeon may then grasp these stay sutures to provide counterforce as the filler tube is advanced. In addition, the surgeon may grasp the stay sutures and the distal suture, or distal stay sutures if such are provided, in order to move the tissue filling device back and forth within the tissue to achieve optimal positioning. When the desired amount of filler material is within the sleeve, the guide rail is cut flush with the skin at the proximal and distal ends of the sleeve, and the stay sutures are similarly cut close to the skin at the proximal end. The stay and guide sutures are ideally of bioresorbable material as are well known in the art.

In one embodiment, the grasping means for positioning the tissue augmentation device comprises a suture, as described above. Other types of grasping means can also be used in accordance with several embodiments of the invention. In another embodiment, the grasping means comprises one or more tabs or flatted areas. In one embodiment, a portion of at least one membrane is flattened to provide the practitioner with an uninflatable area for grasping. One advantage of such an embodiment is that it may reduce the risk of damage (such as a puncture) to the inflatable portion of the augmentation device by minimizing direct contact with the inflatable portion. In one embodiment, the flattened portion or tab comprises one or more layers that are sealed using glue or another adhesive. In one embodiment, the flattened portion, or tab, is made of the same material as at least one of the membranes of the augmentation device. In another embodiment, the flattened portion, or tab, is made of a different material than a membrane of the augmentation device. The flattened portion, or tab, can be made of any shape suitable for grasping by a practitioner. In some embodiments, the tissue augmentation devices comprises a single tab. In other embodiments, the tissue augmentation devices comprises two tabs. In yet other embodiments, more than two tabs are provides. A tab may be located in any location that facilitates grasping by a practitioner. In a preferred embodiment, the tab is located at the proximal and/or distal end of the augmentation device.

In an alternative embodiment and method of use, the tissue filling device is implanted in the tissue to be augmented by means of an outer needle or cannula. The needle has a proximal end and a distal end, and a lumen extending from one end to the other. In one embodiment, the needle is 14-20 gauge. Thus, in one embodiment, the device to be implanted according to any of the embodiments described herein (e.g., the device in its first configuration or uninflated state) is sized to fit through a 14-20 gauge needle or other tubular access channel. A 14-20 gauge tubular access channel translates into a tubular access channel having an outer diameter of about 0.083 inches and an inner diameter of about 0.063 inches (14 gauge) to a tubular access channel having an outer diameter of about 0.0355 inches and an inner diameter of about 0.024 inches (20 gauge). Thus, the device to be implanted, in some embodiments, has a pre-implantation diameter in the range of about 0.024 inches (about 0.61 mm) to about 0.063 inches (about 1.6 mm). In one embodiment, the device pre-implantation or pre-inflation has diameter less than about 1.6 mm. In alternative embodiments, the device pre-implantation or pre-inflation has diameter greater than about 1.6 mm. These latter embodiments need not be delivered through a 14-20 gauge access channel.

In one embodiment, a sleeve assembly comprises the collapsed sleeve, valve and filler tube as described above. Optionally, a central guide rail may be supplied. The sleeve assembly is contained within the needle lumen such that the distal end of the sleeve assembly ends proximally of the distal end of the needle lumen. The filler tube runs through the sleeve and emerges at the proximal end of the needle, and then connected to a syringe containing the filler material. If a central guide rail is provided, the filler tube is adapted to ride over said rail. The filler material can be any of those previously described. In one embodiment, stay sutures are provided attached to the proximal end of the sleeve and emerge through the proximal end of the needle. In use, the surgeon advances the needle along the path in the tissue to be augmented from a proximally located entry site. The surgeon may put manual traction on the tissue in order to guide the needle along the desired path. The filler tube is advanced within the interior of the sleeve, and along the guide rail of such is provide, until the distal end of the filler tube is located at or near the distal end of the sleeve. The needle may be advanced through the tissue and then emerge from the skin at a distally located exit site, or the needle advancement may stop within the tissue without an exit site. In either case, once the needle is in the desired position, forward tension is placed on the filler tube to keep the collapsed sleeve in position, while the needle is retracted proximally out of the tissue. The surgeon then ejects filler material into the filler tube and thence into the sleeve. He can withdraw the filler tube along the length of the sleeve until an adequate tissue augmentation profile is achieved and may re-advance the filler tube distally if required. The filler tube is then removed from the sleeve, allowing the valve at the proximal end of the sleeve to close. If more augmentation is desired, the filler tube may be again passed through the valve and into the sleeve, and over the guide rail if one is provide, where more filler material may be deposited. When the desired amount of filler material is within the sleeve, the filler tube is removed and any guide rail and any stay sutures are cut flush with the skin at the proximal and distal ends of the sleeve.

In one embodiment, the sleeve may take the shape of the upper lip in a "cupid's bow" configuration, with the valve and filler tube assembly as provide above. The sleeve of this upper lip shape is also configurable from a first, collapsed state, to an expanded state. The sleeve of this upper lip shape may be placed within the tissue either using the sew-through method or the outer needle method described above. In this embodiment, the sleeve is generally 3 to 6 cm in length, 1 to 6 mm in width and 1 to 3 mm in depth. The upper edge has a flat "M" configuration to match the upper vermillion border of the lip. The sleeve may be constructed of two sheets of any of the biocompatible materials describe above, preferably ePTFE, attached to each other, such as by an adhesive of thermal cintering, along their edges.

In another embodiment, the sleeve is adapted to be placed in the cheek to enhance the malar fossa. In this embodiment, the shape and dimensions are well known in the art, such as described for silicone implants available from McGhan Medical Corporation, a division of Inamed. In one preferred embodiment, the sleeve is approximately ovoid and constructed of two sheets of ePTFE sintered together at their outer edges, such that the sleeve, when in its inflated state, has dimensions of 4 to 6 cm in length, 3 to 4 cm in width, and 0.3 to 1.5 cm in thickness in the center of the sleeve, with the thickness tapering towards the edges.

In one embodiment, the device is compartmentalized and the compartments are adapted to be filled separately in order to vary the contour of the filled region. In some embodiments, certain compartments are left unfilled or partially filled, and may be filled at a later date to achieve or alter a particular contour. In one embodiment, the device has two or more compartments (e.g., 3, 4, 5, 5-10, 10-20, or more than 20 compartments). As described in more detail below, these compartments can be divided by one or more interior septums. These interior septums can be pierced to inject filler and are re-sealable after a fill tube has been removed. Alternatively, each compartment (which may or may not be separated from other compartments by an interior septum) can be accessed from the exterior. Thus, the exterior can be pierced to provide filler to one or more of the compartments, which then re-seals (with or without external intervention) after a fill tube has been removed. In this manner, a practitioner can selectively fill some or all of the different compartments. The compartments can be of any size or shape (e.g., square, rectangular, circular, ovoid, elongate, triangular, amorphous, etc.). In one embodiment, the compartments are substantially flat. Thus, in one embodiment, the device for implantation into the cheek (or other suitable location) has a width of less than 3 mm. In other embodiments, the thickness is in the range of about 3 to 15 mm, as described above. In yet other embodiments, the thickness is greater than 15 mm.

In another embodiment of the invention, there is provided a tissue augmentation device comprising a generally sheet like structure formed by opposing sheets or walls joined together internally to form multiple chambers in the device. The chambers are selectively fillable, completely or partially, so as to enable the device to be shaped to a desired overall contour. The walls comprise a material that is self-sealing, so that upon withdrawal of a filling means from any chamber that chamber is self-sealed to retain the filler therein. If desired, the contour of the device may even be changed after filling one or more of the chambers by extracting filler therefrom.

Preferably, in this embodiment, the device comprises a pair of sheets of such self-sealing material closed together around their periphery. Such closure can be achieved by any suitable means, such as by heat or chemical bonding. More preferably, the sheets are similarly bonded together in any desired pattern to form multiple chambers or compartments.

In a preferred embodiment, either each or both of the opposing walls of the sheet device may be formed from a laminate of a plurality of layers.

The sheet, which may have self-sealing properties in a preferred embodiment, are preferably made of ePTFE and/or polyurethane.

In a related embodiment there is provided a tissue augmentation device comprising a generally sheet like or substantially planar structure comprising opposing, substantially planar walls joined together by bonding or inner walls to form a plurality of chambers therein. Preferably this embodiment has the characteristics described above. More preferably, the sheet comprises a plurality of inner chambers in an amount generally more than is needed by a surgeon for a particular application. In this embodiment, the surgeon can cut between the chambers so as to produce the desired shape and number of chambers for a particular application.

The sheet or planar chambered embodiments are particularly suitable for facial reconstructive surgery and the like.

In another embodiment, the sleeve adapted to be placed in the cheek has the dimensions described above, but additionally contains a length of Nitinol wire or ribbon in its superelastic state, of approximately 0.003 to 0.030 inches in diameter, which is affixed within the edges along the circumference of the sleeve between the sheets of ePTFE, which make, up the sleeve, using a thermoplastic adhesive such as FEP or polyethylene. In such an embodiment, the sleeve is assisted in expanding from its first configuration to its second configuration, and maintaining its shape in the second configuration, by the shape memory properties of the Nitinol.

In similar fashion, other embodiments of a sleeve in the size and shape adapted to be used as tissue augmentation implants in the dorsum of the nose, the chin, the region under the eyes, the breast, or any anatomic location clinically indicated may be constructed in the fashion described above either without or with the support of a Nitinol frame structure.

Certain specific implementations of the invention will be described with reference to FIGS. 1-12. Referring to FIG. 1, there is illustrated a schematic representation of a tissue augmentation implant in accordance with one aspect of the present invention. The implant comprises a sleeve 10, having a proximal end 12 and a distal end 14. Sleeve 10 may be either an empty sleeve with a single or plurality of macro compartments, or the outer surface of an open cell or closed cell foam as has been disclosed elsewhere herein.

The sleeve 10 comprises a body 16, which, in the present embodiment, defines a central cavity 18. The body 16 is additionally provided with a distal port 20, which is in communication with a proximal port 22 by way of a lumen extending therebetween. In the illustrated embodiment, the distal port 20 is on a distal end of the body 16 and the proximal port 22 is on the proximal end of the body 16. However, either port may be positioned along the length of the body 16 spaced apart from the respected end, depending upon desired performance and other design considerations. A plurality of ports may also be desirable.

In the illustrated embodiment, the distal port 20 and proximal port 22 serve as guidewire access ports to allow the body 16 to be slideably advanced along a guidewire 24.

The illustrated ports 20 and 22 are in communication with each other by way of the central cavity 18. However, a separate lumen may be provided through the sleeve wall or on the outside of the sleeve if it is desired to isolate the guidewire lumen from the filler media.

As has been discussed herein, the body 16 is transformable from a reduced cross sectional configuration such as for positioning at a desired treatment site, to an enlarged cross sectional configuration for providing a desired cosmetic result. In one embodiment, illustrated schematically in FIG. 2, the body 16 is transformed to the enlarged cross sectional configuration by filling the central cavity 18 with any of a variety of desired filler materials 30. A filler tube 26 is advanced along the guidewire 24 to position a fill port 28 within a desired portion of the central cavity 18. The proximal end of the filler tube 26 (not illustrated) is connected to a source of filler media, such as a hypodermic needle syringe or other container depending upon the nature of the filler media. Suitable filler materials are disclosed elsewhere herein, and the nature of the filler tube may be modified to take into account the nature of the filler as will be apparent to those of skill in the art in view of the disclosure herein.

The filler tube 26 may be advanced throughout the length of the sleeve 10 into the vicinity of the distal end 14. Filler 30 may be deployed through the fill port 28 by activation of a fill control (not illustrated) on the proximal control. The filler tube 26 may be axially proximally retracted through the sleeve 10 to introduce filler 30 at different positions along the length of the sleeve. After a sufficient amount and desired distribution of filler 30 has been introduced into the sleeve 10 to achieve the desired result, the filler tube 26 may be proximally retracted from the proximal end 12, and removed from the patient. See FIG. 3. Proximal end 12 may be provided with a valve 32 as has been described herein, to permit removal of the filler tube 26 and retention of the filler media 30 within the sleeve 10. The guidewire 24 may also thereafter be proximally withdrawn from the sleeve 10, thereby leaving the filled implant in position at the desired treatment site.

For certain applications, the sleeve 10 is preferably fillable to a non-uniform profile. This may be accomplished utilizing the embodiment of FIGS. 1-3, together with a filler which has sufficient viscosity, or structural characteristics (e.g. wire coils) that the filler will remain at a localized position within the sleeve 10. Alternatively, referring to FIG. 4, there is illustrated a segmented embodiment of the invention. The sleeve 10 is divided into a plurality of segments 34, which are separated by a plurality of neck portions 36. The fill port 28 on the fill tube 26 may be sequentially positioned within each of the segments 34, to allow each segment 34 to be inflated to a unique cross sectional dimension. In this manner, the cross sectional dimensions of the implant are customizable along the length of the implant as may be desired to achieve a desired cosmetic result.

The neck portion 36 may be formed in any of a variety of ways, such as by heat forming the sleeve 10, or by placing any of a variety of structures such as a band around the neck portion 36. Referring to FIG. 5, the segmented implant is illustrated with a filler tube 26 in place within a segment 34. Adjacent segments 34 are separated by a restriction 37 such as an annular elastic band or gasket. The restriction 37 has sufficient elasticity to permit passage of the filler tube 26, but recoils back to close of substantially close the passageway between adjacent segments 34 following removal of the filler tube 26. Thus, the restriction 37 may be configured to either restrict and control flow between adjacent segments 34, or completely block flow of filler 30 between adjacent segments 34.

The nature of the restriction 37 in neck portion 36 is configured to cooperate with the nature of the filler 30 as will be appreciated by those of skill in the art in view of the disclosure herein. For example, the restriction 37 need not provide a rigorous seal if the filler 30 comprises a plurality of coils, fibers, or particular material. However, if a less viscous or more flowable filler 30 such as saline solution is utilized, restriction 37 should be configured to provide a seal between segments 34 if it is desired to prevent flow of filler 30 between adjacent segments 34. Optimization of these parameters may be achieved through routine experimentation by those of skill in the art, taking into account the desired clinical performance of the implanted device.

Referring to FIG. 6, a sleeve having a plurality of internal baffles 40 is disclosed. Baffles 40 function to divide the interior cavity 18 of the sleeve 10 into a plurality of chambers or compartments 38, without necessarily influencing the external profile of the implant. Similar to the restriction 37, baffles 40 permit the filler tube to be advanced and retracted to reach each compartment 38, and then to prevent or to substantially prevent the flow of filler 30 between adjacent compartments depending upon the desired clinical performance. As a further alternative, the baffles 40 or valves may be in the form of a pierceable septum, which permits passage of the fill tube 26 but which reseals either completely or substantially following removal of the filler tube 26. Alternatively, each chamber or compartment (which may or may not be separated from other compartments by an interior septum) can be accessed from the exterior. Thus, the exterior can be pierced to provide filler to one of the compartments, which then reseals (with or without external intervention) after a fill tube has been removed. In this manner, a practitioner can selectively fill some or all of the different compartments to achieve a desired profile or contour.

Referring to FIG. 7, there is illustrated one embodiment of a filler tube 26 in additional detail. Filler tube 26 comprises a proximal end 50, a distal end 52 and an elongate tubular body 54 extending therebetween. Tubular body 54 may be flexible or rigid, depending upon the desired performance. Tubular body 54 may be formed in any of a variety of ways, such as by machining from metal components (e.g. stainless steel hypotube) or by extruding any of a variety of polymeric materials well know in the catheter arts, such as PEEK, PEBAX, various densities of polyethylene, among others.

The tubular body 54 includes at least one central lumen for receiving the guidewire or guide rail 24 therethrough. The guidewire lumen is in communication with a guidewire access port 58 on the proximal manifold 56. Proximal manifold 56 is additionally provided with a filler port 60, which may be a lure connector or other quick release hub, for removable connection to a source 62 of filler 30. In one convenient embodiment, source 62 is in the form of a manually activatable syringe.

The tubular body 54 may be provided as a dual lumen structure, having either concentric or side-by-side lumens as is well known in the catheter arts. Alternatively, depending upon the nature of the filler 30, the guide rail 24 may extend through the same lumen as the filler media as well be appreciated by those of skill in the art in view of the disclosure herein.

Although the filler tube 26 is illustrated as having a single effluent port 28 for introducing filler 30 into the sleeve 10, a plurality of filler ports 28 may be provided. In addition, the filler port 28 may be the same as the distal opening through which the guide rail 24 extends. In an embodiment having multiple effluent ports 28, the multiple ports may be arrange circumferentially in a single transverse plane about the tubular body 54, or may be spaced axially apart along the length of the tubular body 54 such as for use in a procedure where it is desired to fill multiple compartments 38 simultaneously.

A further implementation of the invention is illustrated in FIG. 8. A schematically illustrated sleeve 10 extends from a proximal end 12 to a distal end 14. The sleeve comprises a flexible body 16 which may comprise an outer fabric sleeve or the outer surface of a segment of foam, as has been discussed elsewhere herein. In the illustrated embodiment, the body 16 defines at least one central cavity 18, having a proximal port 22. Proximal port 22 is provided with a valve 32, for sealing the central cavity 18 following introduction of filler material 30 and removal of the filler tube 26.

In the implementation of the invention illustrated in FIG. 8, the distal end 14 of the sleeve 10 is provided with a closed end. A distal suture 70, extending from a proximal end 72 to a distal end 74 is attached to the closed distal end 14 of the sleeve 10. In alternative embodiments, distal end 14 may be provided with an open access port, with or without a valve, depending upon the desired filling configuration. The suture 70 may also extend throughout the length of the sleeve 10, and proximally from the proximal end 12 of sleeve 10, depending upon the desired performance.

In the illustrated embodiment, the distal suture 70 extends from the distal end 14 of the sleeve 10, to a needle 76 attached to the distal end 74 of the suture 70. Needle 76 may comprise any of a variety of sewing needles, as will be apparent to those of skill in the art in view of the disclosure herein.

FIG. 9 schematically illustrates the use of the embodiment of FIG. 8. The needle 76 is introduced into the skin 73 at a first access point 75. The needle is advanced subcutaneously beneath an area to be treated. Needle 76 is thereafter advanced through the surface of the skin at an exit point 77. Further traction on the needle 76 and suture 70 pull the tubular sleeve 10 through the entrance point 75 and into position beneath the region of skin to be treated. Once the sleeve 10 is in the desired position, the filler material 30 is advanced from a source into the central cavity 18. Following introduction of a desired volume of filler material 30, the filler tube 26 is proximally withdrawn from the sleeve 10, and the distal suture 70 is severed at or below the skin surface.

Referring to FIGS. 10 and 11, there is illustrated an embodiment like that in FIGS. 8 and 9, with the added feature of a proximal stay suture 78. Proximal stay suture 78 may be attached to the sleeve 10 in the vicinity of the valve 32, or may be a continuous suture with the distal suture 70, extending along the outside or the inside of the body 16.

In use, the proximal stay suture 78 and the distal suture 70 may be used to manipulate the sleeve 10 along its axis to optimize positioning either before, during or following introduction of filler material 30 into the central cavity 18.

A schematic representation of the use of an external introduction needle is illustrated in FIG. 12. In the present context, the use of the term "needle" is not intended to imply any specific structural dimensions, other than as necessary to provide access for subcutaneous insertion of the implant. The actual dimensions of the introduction needle will be optimized for or governed by the configuration of the implant and filler tube as will be apparent to those of skill in the art.

Placement needle 82 comprises an elongate tubular body 83 extending between a proximal end 84 and a distal end 86. Tubular body 83 comprises an elongate central lumen 88 extending therethrough. The tubular body 83 may comprise any of a variety of forms, depending upon the intended clinical use. For example, tubular body 83 may comprise a straight, a curved, or a flexible configuration. Typically, the distal end 86 will be provided with a bevel or other sharpened tip, to facilitate advance through soft tissue. Depending upon the diameter of the tubular body 83, a separate obturator tip may be positioned within the tubular body 83 to facilitate positioning of the tubular body 83 in the desired treatment site. The obturator may thereafter be removed, and the sleeve 10 advanced into position within the tube.

In the embodiment schematically illustrated in FIG. 12, the tube 83 has a sufficient inside diameter to accommodate a proximal hub 90 on the filler tube 26. This allows the placement needle 82 to be proximally retracted over the assembly of the sleeve 10 and filler tube 26 following placement at the treatment site. Alternatively, the placement needle 82 can be configured to be withdrawn in a distal direction out of the exit point 77 (see FIG. 9). Thus, depending upon the desired clinical performance, the placement needle 82 may be proximally retracted or distally advanced off of the sleeve 10. In an alternate configuration, placement needle 82 may be in the form of a peel-away sheath, which can be removed proximally without the need for an inside diameter sufficient to accommodate the proximal hub 90. Any of a variety of configurations may be utilized for the placement needle 82, as will be apparent to those of skill in the art in view of the disclosure herein.

Referring to FIGS. 13A through 13D, there is illustrated a manufacturing sequence for a tissue augmentation device in accordance with the present invention. 13A illustrates a tubular sleeve 100 which extends between a proximal end 102 and a distal end 104. A central lumen 106 extends therethrough. Tubular sleeve 100 may comprise any of a variety of materials such as ePTFE and others described elsewhere herein. In general, tubular sleeve will have a sufficient length and diameter to accommodate the desired treatment site. For treatment of wrinkles in the face, tubular sleeve 100 will generally have a length within the range of from about 1 cm to about 6 cm, and a diameter within the range of from about 1 mm to about 8 mm. The wall thickness of the tubular sleeve 100 may also be varied considerably, but will often be within the range of from about 0.003 to about 0.020 inches.

Referring to FIG. 13B, there is illustrated the first step in construction of the proximal valve 114. A biasing element 108 such as an elastic band, suture, spring biased metal clip, or other clamp or biasing member is positioned around the tubular sleeve 100 to create a neck, spaced slightly apart from the proximal end 102 leaving a trailing end 110 of the tube 100. The biasing element 108 is preferably sufficiently tightly positioned around the tube 100 to provide a suitable seal taking into account the desired filler material as has been discussed.

As seen in FIG. 13C, the tubular body 100 is then turned inside out (everted) so that the trailing end 110 is positioned within the central lumen 106. The biasing element 108 is also positioned within the central lumen 106, presenting a valve opening 114 on the proximal end 102 of the tubular body 100. Valve opening 114 permits the introduction and removal of a filler tube as has been discussed.

Referring to FIG. 13D, a distal closed end 120 is formed on the tube 100. Closed end 120 may be provided in any of a variety of ways, such as by one or more loops of a suture 118 which may be tied into a knot. Alternatively, any of a variety of adhesives, thermal welding, elastomeric bands, clips or other biasing structures such as those utilized to form valve 114 may be used. In the illustrated embodiment, closed end 120 is provided by tying a suture tightly around the distal end 104 of the tube 100. A trailing end 116 of the suture is left attached to the suture knot, to provide assistance during positioning as has been discussed. The distal suture 116 may thus be provided with a sewing needle (not illustrated) for percutaneous introduction into the treatment site.

Referring to FIG. 14, there is illustrated a tissue augmentation device as in FIG. 13D, with an optional guidewire 122. Guidewire 122 extends through the valve 114, and at least as far as the distal closed end 120. Guidewire 122 may be permanently attached, at the closed distal end 120, or may be removable such as by proximal traction depending upon the desired clinical performance. In one embodiment, the guidewire 122 is secured within the suture knot 118 and not intended for removal. In this embodiment, following placement and filling of the implant, the proximal portion of guidewire 122 is severed at about the valve 114. Guidewire 122 may comprise any of a variety of filaments, such as a suture, or a metal wire such as stainless steel or Nitinol. As has been discussed, guidewire 122 may provide assistance in axial repositioning or positioning of the filler tube, which may be advanced over the guidewire 122 and into the tubular sleeve 100.

Various embodiments of implants disclosed therein, both of a generally cylindrical form and of a generally sheet-like form, may be implanted in several locations throughout the body. Some specific possible implant locations on the face are illustrated in FIG. 15 below.

Referring to FIG. 15, implants of the disclosed design are also useful in the periorbital region, such as the suborbital rim 210, including the more medial portion of the suborbital zone known as the tear trough 216. Depending on physician preference and patient anatomy, an implant for this location can be similar to either the elongate, generally linear implants such as those used for the nasolabial region 200, or can be of a more sheet-like planar nature and extend inferiorly to the region in which the malar prominence meets the cheek or medially to the region in which the malar prominence meets the nose (the nasojugal region).

Wrinkles in the glabellar region 212 can be corrected with an implant of the disclosed design as well. As described in reference to the periorbital region, the particular anatomy of this region and physician preference will determine whether a linear or planar implant is best suited, as either can be effective for the types of defects or wrinkles found in this region.

In another embodiment, the bridge of the nose 214 can be augmented with a planar-type implant of the disclosed design. Use of such an implant can be particularly effective in patients who have a flattened nasal bridge but desire a more prominent nasal bridge.

Figure 16:
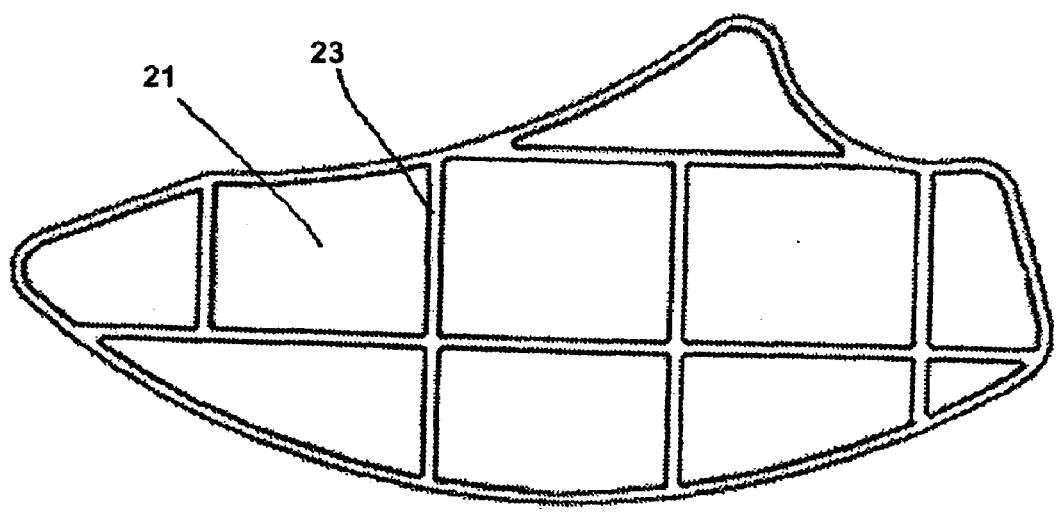
FIG. 16 is an overhead plan view of a segmented malar mid-face implant in its deflated state, according to one embodiment of the invention.
Figure 17:
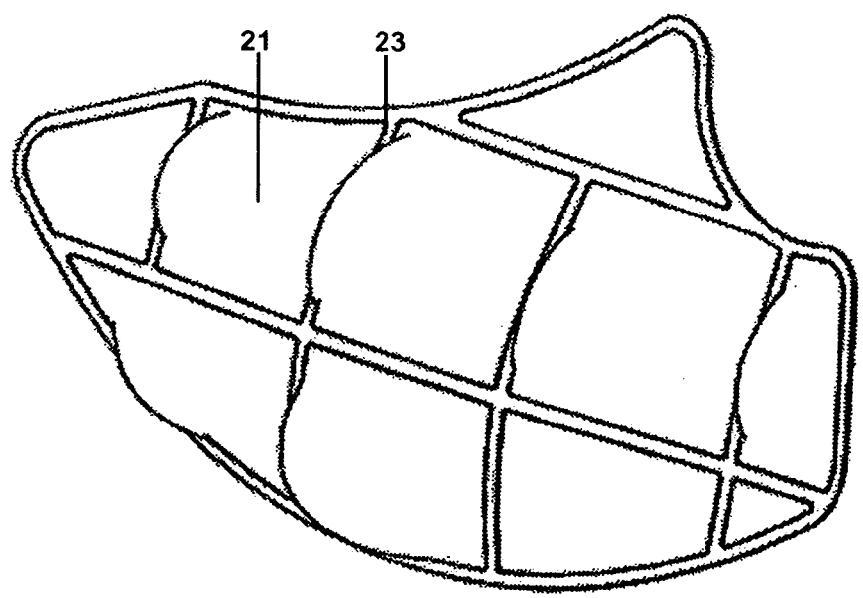
FIG. 17 is a representation of a segment malar mid-face implant in its inflated state according to one embodiment of the invention.

In one embodiment, augmentation of the malar and sub-malar regions 218 by use of an implant of the disclosed design can be very effective in reshaping a patient's face through the alteration of the underlying structure on which the overlying soft tissue is draped. Implants in this location would benefit from use of the disclosed self-sealing chronically adjustable membrane, as would all of the other implants described herein. FIG. 16 is a plan overhead view of a deflated mid-face malar implant, while FIG. 17 illustrates the same implant in inflated condition. Both figures illustrate an embodiment with a plurality of internal segments 21, which may be separated by a series of valves or baffles 23 (e.g., seams formed by thermal bonding, adhesives, etc.) described above. Furthermore, a planar implant may also be used in the temporal region 220.

Figure 18:
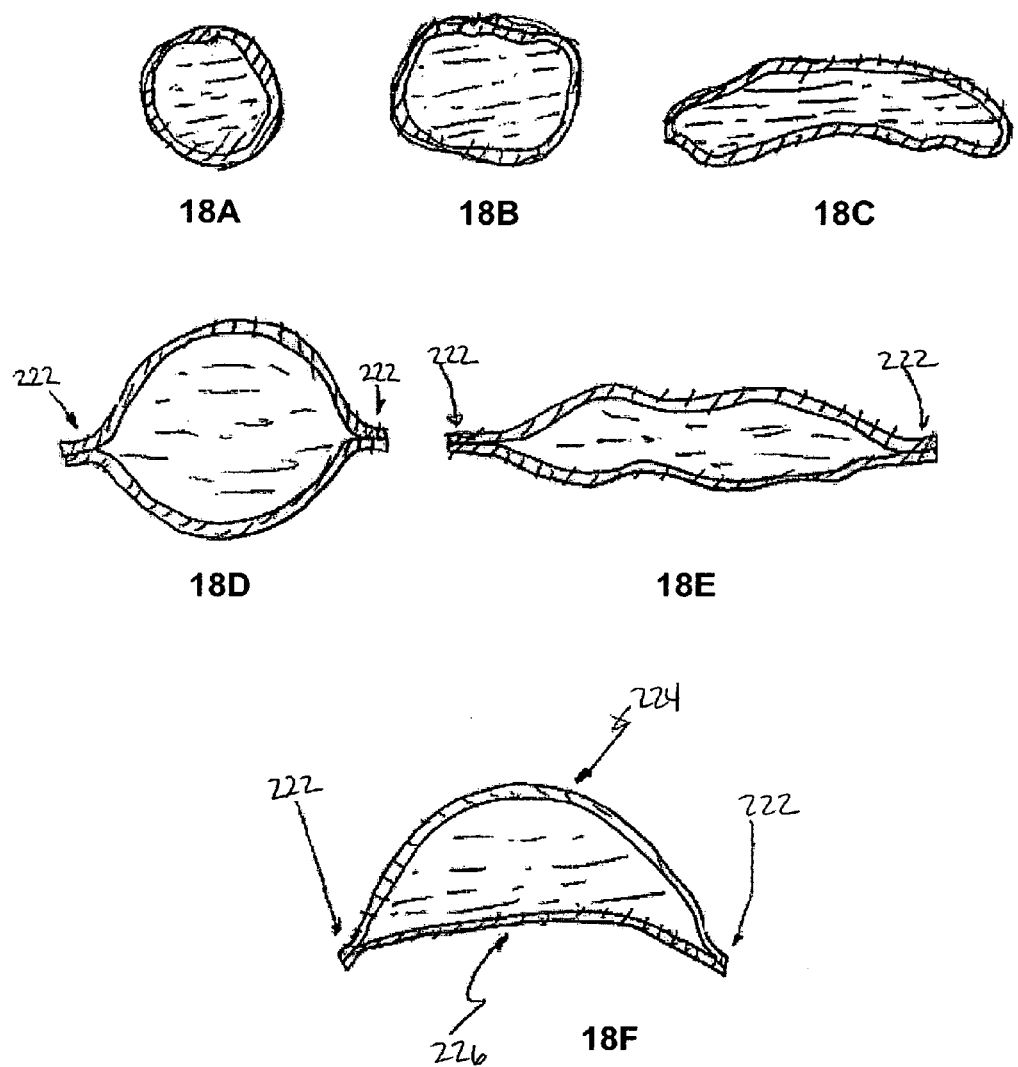
FIGS. 18A-F are cross-sections of various preferred tube-based and sheet-based implants in various configurations.

FIG. 18 shows cross-sections of various preferred tube-based and sheet-based implants in various configurations that can be utilized depending on the desired implant location, specific contours of the patient's face, and physician preference. FIG. 18A illustrates the configuration of a tube-based, taut-filled implant. FIG. 18B shows a tube-based, slightly flaccid implant. FIG. 18C shows a tube-based markedly flaccid-filled implant. FIG. 18D shows a sheet-based, taut-filled implant. FIG. 18E discloses a sheet-based, flaccid filled implant. FIG. 18F shows an example of a sheet-based implant with two sheets of differing compliances (or two sheets of similar compliance but dissimilar area) that may be desirable in order to make an asymmetric cross-section upon inflation. Sheet layer 224 shown is desirably constructed of, for example, a relatively low modulus elastomeric film that is highly compliant, producing a more curved shape. Sheet layer 226, in contrast, may be made of a relatively higher modulus, less compliant elastomer/polymer. The sheet-based implants may all use bonded seams 222 to connect the two sheet layers together.

Figure 19:
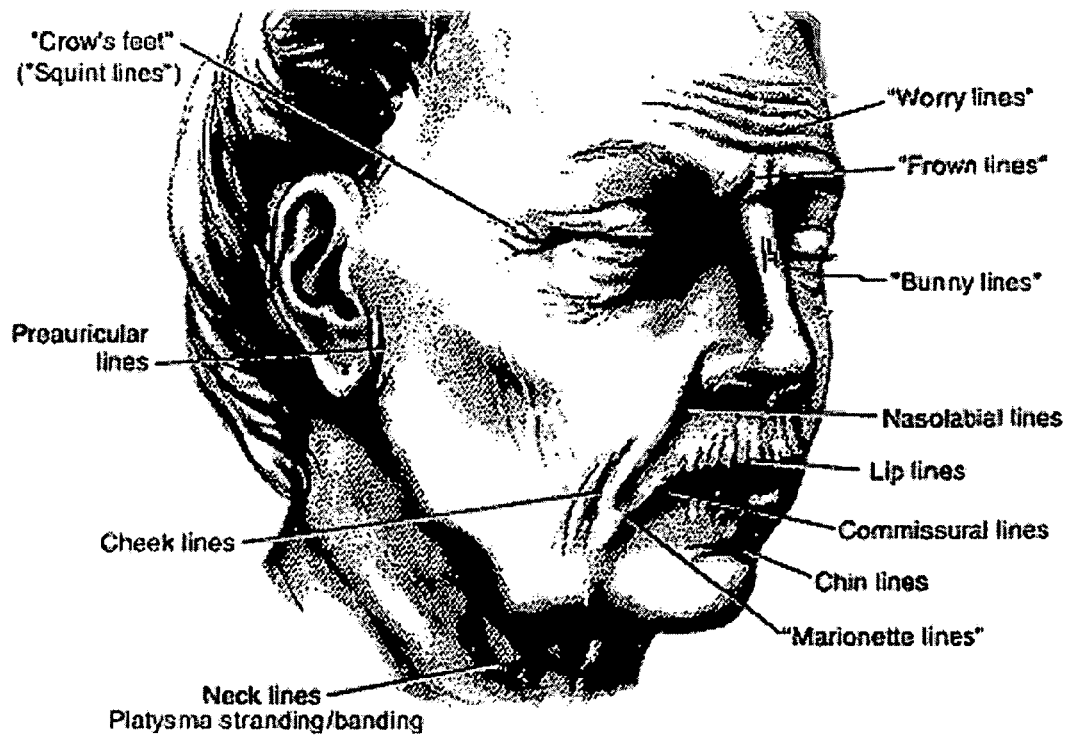
FIG. 19 illustrates various wrinkle lines of the face that may be treated with the disclosed implants, according to one embodiment of the invention.

In one embodiment, an implant 200 (FIG. 15) that is of an elongate nature may have a cross-section that is either substantially round or a flattened shape (when flaccidly filled) as previously disclosed, and illustrated in FIGS. 18A-C. Alternatively, the implant may be constructed using a sheet-based method to product cross-sections such as those shown in FIGS. 18D-F. Such an implant is well suited to effacement of the nasolabial groove. A similarly shaped but shorter implant 202 can be used for the marionette lines (or "pre-jowl sulcus"). In both of these cases, the implant is used to augment the soft tissue that lies beneath a line-like feature in the patient's skin, commonly referred to as a wrinkle or rhytid. Similarly, implants of this type will be effective at any of the locations shown in FIG. 19, illustrating the terminology and anatomical location of typical sites of facial wrinkles. Length, diameter, cross-sectional shape and overall shape, such as whether the elongate shape is linear or arcuate, bulbous, tear-drop shaped or otherwise curved, are ideally chosen to best suit each of these locations. Alternatively, many of the wrinkle locations on many patients may be effectively effaced through the use of an implant selected from a kit which includes a relatively small number (e.g. at least about three or four and often no more than about 5 or 10) of more generically shaped implants that are made available in incremental lengths and diameters.

In another embodiment, a deeper implant 204 can be used for the several locations in the chin (mental) region or other portions of the mandible. The implant will have a curved shape if used to augment the central mentum in order to match the natural curvature of the bone, but is less curved if used to augment the posterolateral mandible 206 also referred to as the angle of the mandible or the pogonion. Implants such as this will generally be formed using sheet-based methods and be implanted at a relatively deep tissue plane, such as just supraperiosteal or infraperiosteal (just on or below the outer surface layer of the bone). In some cases, however, physicians may, depending on aesthetics and the unique characteristics of the patient choose to place these implants in the same subdermal plane used for the wrinkle-correcting implants such as those described above.

Figure 20:
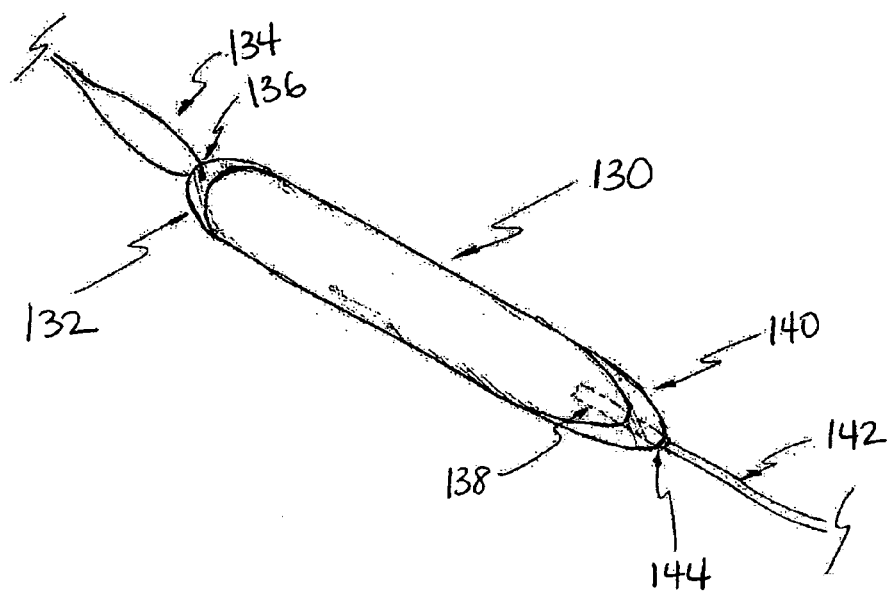
FIG. 20 is an inflatable nasolabial implant in a deflated state, according to one embodiment of the invention.

Also disclosed in the present invention is a tissue augmentation device specially tailored for nasolabial implantation. The method of implantation, as well as a specialized grasper to assist in implantation, will also be described. In this embodiment, there is a tissue augmentation device with size and shape that is preferred for placement below the nasolabial area of a patient's face in order to efface the crease-like appearance of that area. Other sizes and shapes may be preferred for other facial zones as described below. FIG. 20 shows one embodiment of an inflatable tubular implant in its deflated state as it would be seen prior to insertion into the soft-tissue (such as the nasolabial region) of a patient. The body 130 of the implant constitutes the central portion and is responsible for the majority of the volume augmentation that the inflated implant provides. A distal tab 132 is provided to allow for insertion and manipulation of the implant without directly grasping or otherwise attaching to the implant body. In this embodiment, "distal" refers to that end being farther away from the typical point of entry. In the case of the nasolabial area, the distal end of the implant will typically be positioned in the perialar zone (near the patient's nostril) and will thus also be referred to as the superior or cranial ends.

In one embodiment, also shown in FIG. 20, the distal tab 132 is provided with a through-passage such as a punched hole 136 which allows passage of a suture 134. The hole 136 may be provided with a reinforcement structure, such as a metal or polymeric ring to reduce the risk of the suture pulling through the distal end of the tab 132. Alternatively, a filament such as a wire can extend axially along a first side of the implant, loop around the distal side of the hole 136 and then extend axially along a second side of the implant. Alternative reinforcing structures may also be used.

The suture 134 may be formed into a loop as shown here or may pass through the tab and then be knotted in typical fashions. The suture 134 allows the physician, who may also be an assistant, or other operator, to apply traction to the distal end of the implant for purposes of either providing location and orientation control during and after the implantation procedure, drawing the implant into the tissue to implant it (in what is referred to as the "sew-through" method), or both. The suture 134 connects on its other (distal) end, not shown, to either a surgical needle or to a delivery system which may combine needle elements with other delivery system elements, such as dissection components for sharp dissection, blunt dissection or both.

The distal tab 132 meets the body of the implant 130 along a generally arcuate path, said path being formed during the fabrication process by controlled application of adhesive, heat-bonding or other suitable bonding means, under compression using a curved tool. The generally circular path of the edge of the bond causes the implant to inflate at its distal end into a bulbous shape. This design is advantageous in that it more closely matches the required tissue augmentation of this region of the nasolabial area: the subdermal tissue plane in which the implant is optimally placed is at its deepest in this location relative to the rest of the nasolabial region, from approximately 2 mm to 6 mm deep to the skin, and the depth and extent of the nasolabial crease (which can also be referred to as the nasolabial fold or the nasolabial sulcus) is at its greatest in this location. A distal tab 132 may have an axial length of at least about 1/16", 1/8", 1/4", 1/2", or more, and may further enable grasping by a grasping tool, described further below.

In another embodiment, a proximal tab 140, with or without a reinforcing element may be provided as well to allow further locational and orientational control of the implant during and after the implantation procedure. The proximal tab 140 also provides a fixation zone for the valve assembly 138, which may be fixated to the inside materials of the proximal tab 140 by adhesive, heat-bonding or other suitable bonding means. A proximal tab 140 may have an axial length of at least approximately 1/16", 1/8", 1/4", 1/2", or more to enable grasping by a grasping tool, described further below.

Figure 21A:
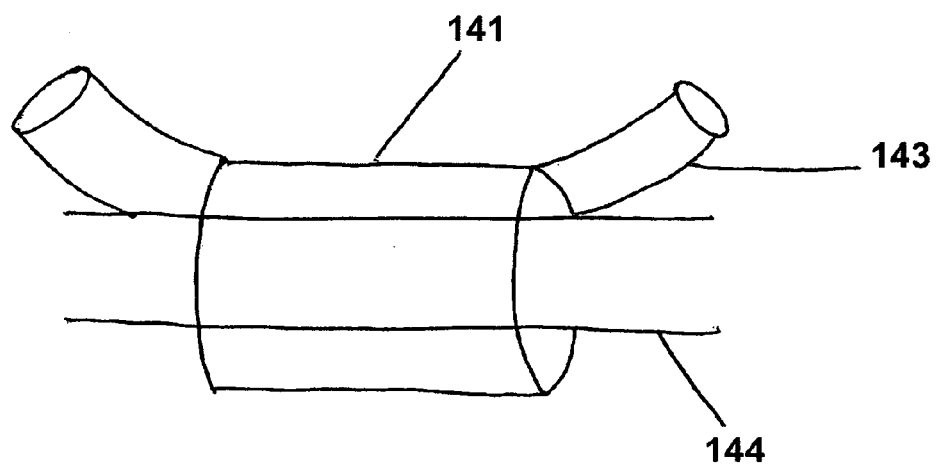
FIG. 21A is a valve assembly, according to one embodiment of the invention.
Figure 21B:
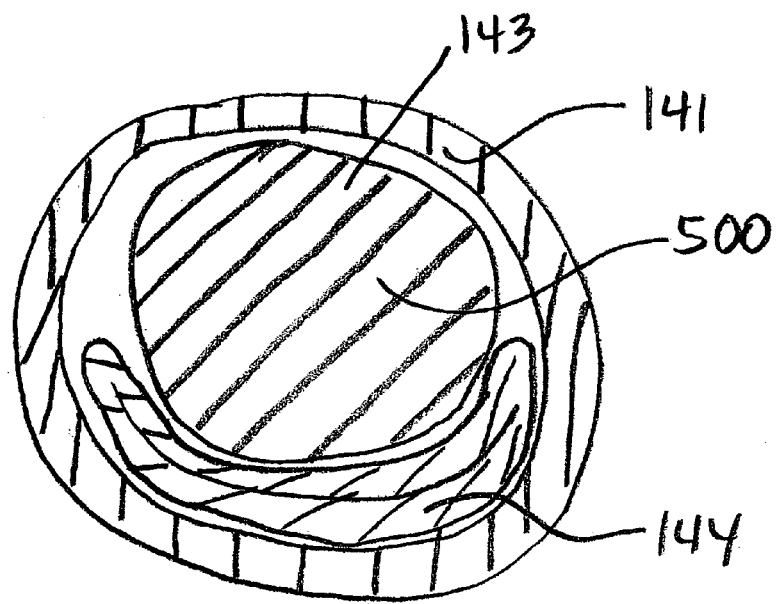
FIG. 21B is an exaggerated cross-sectional view of the valve assembly of FIG. 21A.

The most proximal portion of the valve assembly is the neck tube 144 into which the fill tube 142 is inserted. FIGS. 21A and 21B illustrate the components of the valve assembly. The valve assembly consists of a neck tube 144 surrounded by an elastomeric valve tube 141 or other spring-like material such as stainless steel, spring steel or superelastic NiTi. Positioned within the elastomeric tube 141 and adjacent the tube 144 is a valve plug 143. In FIG. 21B, an exaggerated cross-sectional view of the valve assembly (to show the functional relationship between the valve plug 143 and neck tube 144, a cylindrical valve plug 143 positioned within an outer sleeve of the valve tube 141, causes the neck tube 144 to collapse in a "crescent-moon" shape in response to the inward radial constriction of the valve tube 141. Without the valve plug 143, the neck tube 144 would constrict in sphincter-like fashion thus allowing leakage along the small folds inherent in that type of collapse. The valve plug 143 may contain or comprise filler material 500 such as compressible foam or an elastomeric rod holding the valve tube collapsed unless the filling cannula is in position therein.

Figure 21C:
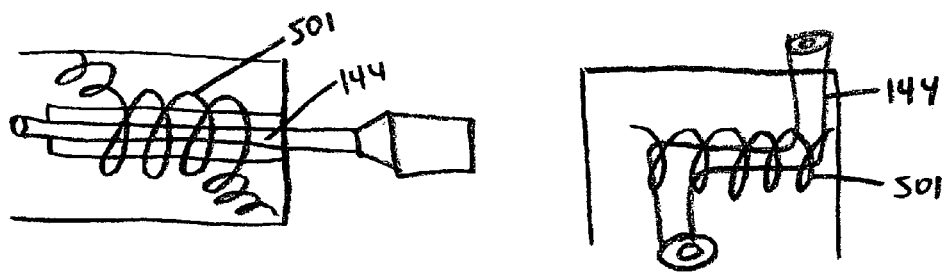
FIG. 21C is a valve with a nitinol coil plug, according to one embodiment of the invention.
Figure 21D:
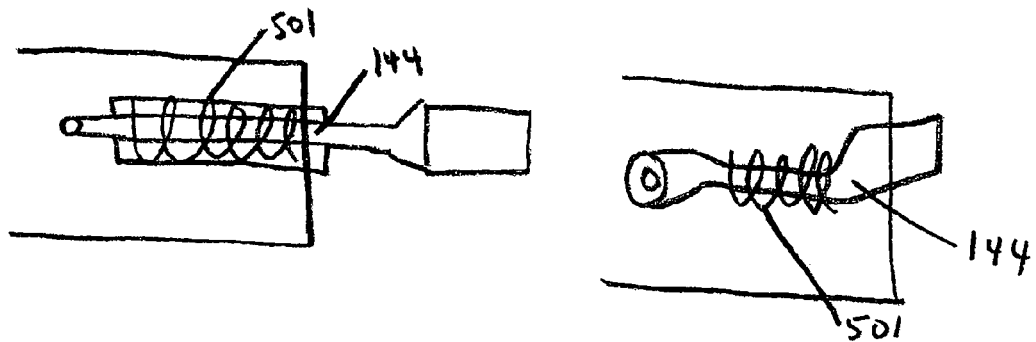
FIG. 21D is another valve with a nitinol coil plug in a different configuration, according to one embodiment of the invention.
Figure 21E:
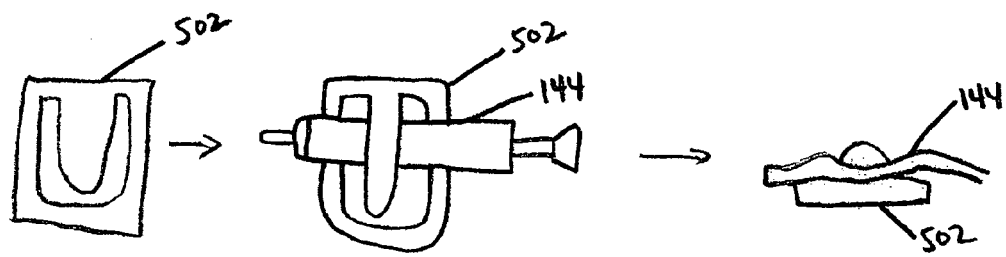
FIG. 21E is a valve with a "paper clip" configuration of the nitinol coil plug, according to one embodiment of the invention.
Figure 21F:
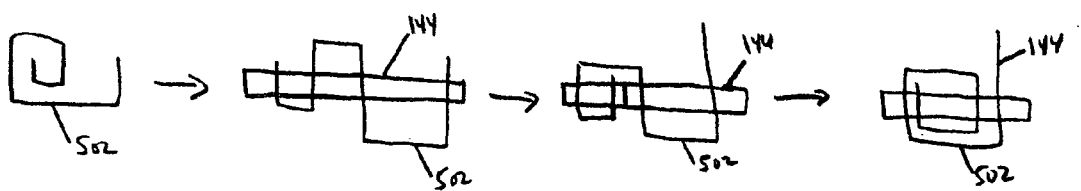
FIG. 21F is another variation of a nitinol coil plug, according to one embodiment of the invention.
Figure 21G:
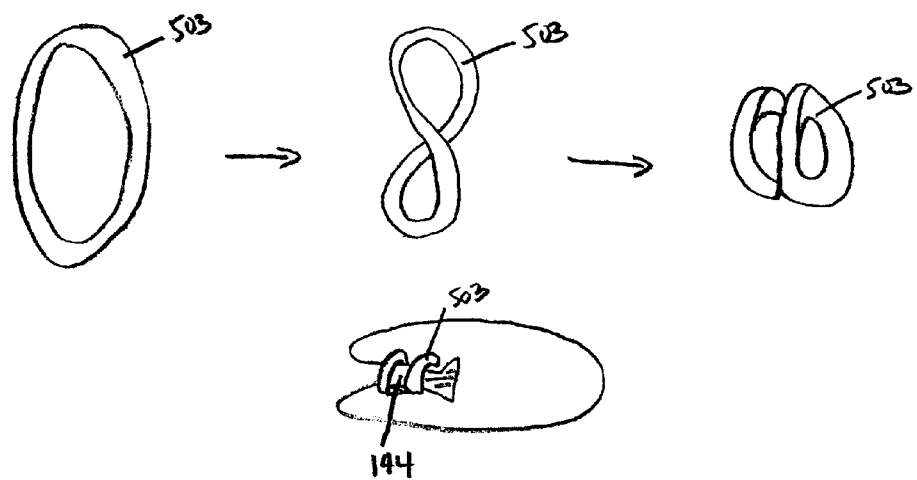
FIG. 21G is a valve with a folded O-ring configuration, according to one embodiment of the invention.

Depending on the desired long-term performance of the valve assembly, it may be desirable to add an additional sealing component, such as a nitinol or stainless steel, clip or a seal by heat sealing or application of an adhesive after filling, to maintain the competency of the valve. Some additional sealing components are depicted in FIGS. 21C-G. FIG. 21C is a valve with a nitinol coil restraint 501, while FIG. 21D is another valve 144 with a nitinol coil restraint 501 in a different configuration, according to one embodiment of the invention. FIG. 21E is a valve 144 with a "paper clip" configuration of the nitinol coil restraint 502, while FIG. 21F is another variation of a nitinol coil restraint 502, according to another embodiment of the invention. Another alternative embodiment of an additional sealing mechanism is shown in FIG. 21G, a valve 144 with a folded O-ring 503 configuration. Any other variety of additional steps such as sealing, clamping, locking, gluing, radiofrequency welding, or ultrasound may also be utilized. Furthermore, in another embodiment, a thermal source such as laser, electricity, flame, or a heating loop may be utilized to melt the valve shut, such as a flange with a wire loop attached to the fill tube and proximally connected to a power source, such as a battery.

Figure 22:
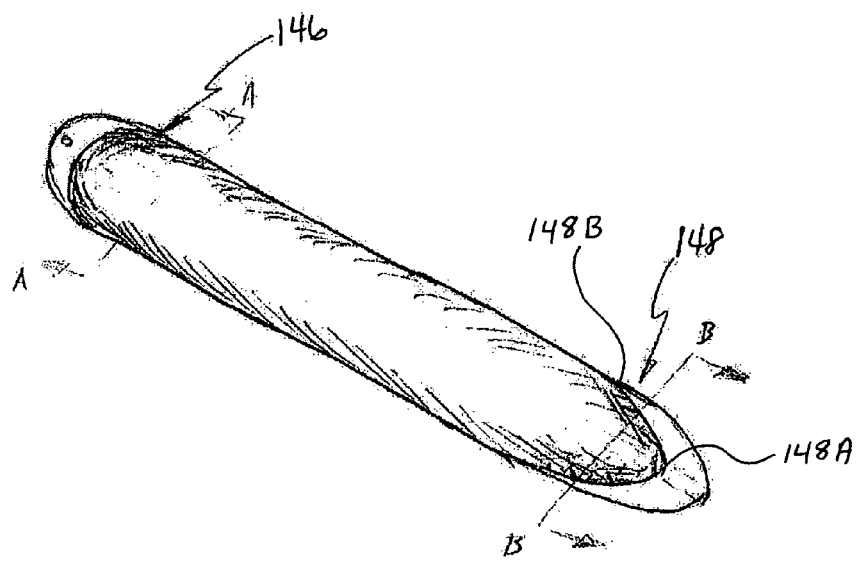
FIG. 22 is an inflatable nasolabial implant inflated to its maximally recommended fill volume, according to one embodiment of the invention.

FIG. 22 shows an embodiment of the same implant of FIG. 20 after it has been inflated and after the fill tube has been removed and the self-closing valve assembly has closed to maintain the inflation of the implant. Typically, the implant is inflated with saline, although other materials can be used as well as previously described. The distal taper 146 forms a generally hemispherical or bulb-like shape while the proximal taper 148 forms a more flattened, triangular shape. The advantage of the distal taper shape was described above. The proximal taper 148 inflates to a more flattened shape because the edge of the bond that separates the proximal taper 148 from the proximal tab of the implant follows an arcuate path or other geometry perimeter line that is elongated axially relative to the arcuate path of the edge of the distal tab. As a result, the distance, measured in an axial direction, between the proximal limit 148A and the distal limit 148B of the distal edge of the proximal bond is greater than the corresponding axial distance on the distal end of the implant. The proximal bond edge length is generally at least about 110%, often at least about 150% and can be at least about 200% of the axial length of the distal bond edge. Thus the implant can not inflate as fully in the direction perpendicular to the plane of the tab at a comparable distance from the end of the tab. This design is advantageous in that it more closely matches the required tissue augmentation of this region of the nasolabial area: the subdermal tissue plane in which the implant is optimally placed is at its most superficial in this location relative to the rest of the nasolabial region, from approximately 1 mm to 4 mm deep to the skin, and the depth and extent of the nasolabial crease (which can also be referred to as the nasolabial fold or the nasolabial sulcus) is at its minimum in this location.

The dimensions of a preferred implant are as follows. The inflated axial length may be from about 1-15 cm, preferably about 1.5-8 cm, more preferably about 2-5 cm. The diameter of an inflated implant may be from about 2-10 cm, preferably about 3-8 cm, more preferably about 4-6 cm. The maximal cross-sectional area of an inflated implant may be no more than about 80 cm$^2$, preferably no more than about 50 cm$^2$, more preferably less than about 30 cm$^2$, or even 12 cm$^2$ or less. In certain embodiments, it may be desirable to have a uniform diameter and cross-sectional area through the body of the implant. In alternative embodiments, the cross-sectional area may vary along the axial length of the implant, with at a first axial distance from an end there will be a first cross-sectional area, and at a second axial distance from the end there will be a second, different cross-sectional area. This second cross-sectional area may be at least about 110%, 120%, 130%, or more of the first cross-sectional area. These alternative embodiments thus may create an implant that has, for example, a transition such as a uniform taper, progressive curve, accelerated curve, and the like.

Figure 23A:
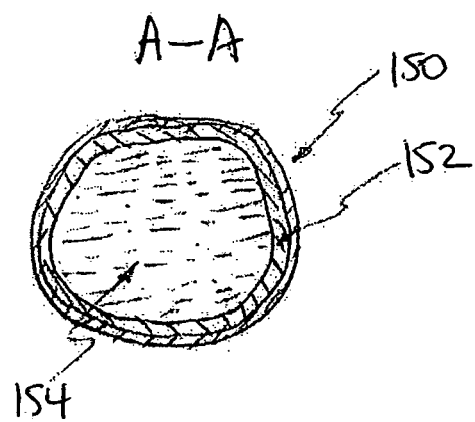
FIG. 23A illustrates a cross-sectional view of a nasolabial implant fully inflated as recommended, near its distal end, according to one embodiment of the invention.

FIG. 23A is a cross-sectional view through the implant in the region of the distal taper 146. It is shown first in an embodiment in which the physician has chosen to inflate the implant to its maximum recommended inflation volume, which creates a soft, flaccid implant but is at the highest end of the range of volumes that will create those soft, flaccid characteristics. At this fill-volume, the cross-sectional shape of the implant in the main body section as well as in the distal taper region is close to circular. For example, a preferred maximum fill volume of an implant may be in the range of from about 1-60 cc, preferably from about 5-40 cc, 10-30 cc, or more preferably about 15-25 cc. A preferred flaccid-filled implant may be filled to about, for example, no greater than about 50%, 60%, 70%, 80%, or 90% of the maximum fill volume.

Also seen in FIG. 23A is the dual-layer construction of a preferred embodiment. An outer porous or textured material layer 150, such as expanded polytetrafluoroethylene (ePTFE), porous polyethylene, textured polyurethane or textured silicone contacts the body tissues surrounding the implant. The characteristics of these materials allow for incorporation of the implant into the tissue without encapsulation. This is due to controlled and slight cellular ingrowth that occurs with the properly selected porous or textured material. One such material is ePTFE with a pore size of between 30 and 100 microns, preferably between 50 and 80 microns.

Figure 23B:
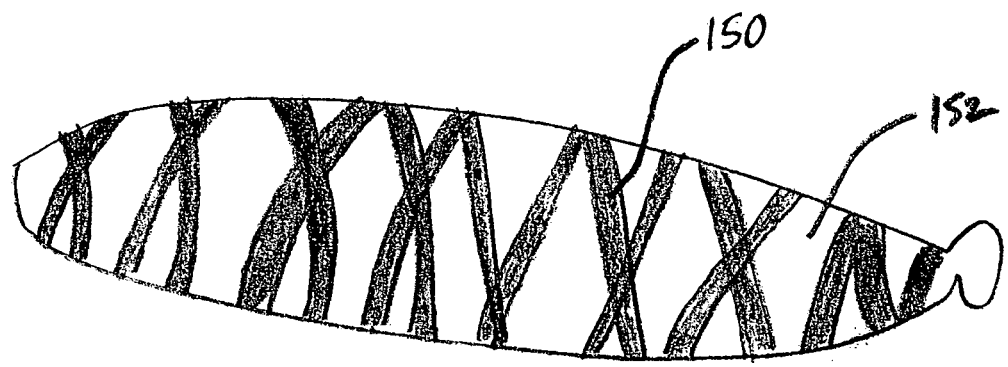

FIG. 23B illustrates an embodiment of an implant with variations in lamination, in which the porous outer material 150 is affixed to the underlying inner elastomeric material 152 in wound or interrupted configurations, for example, helical, bands, stripes, and other discontinuous patterns. These alternative embodiments are beneficial in controlling the total surface area susceptible to tissue ingrowth and reducing capsule formation, such as when it is desired that the implant be removed at a later date. The percentage of the total surface area of the implant which is provided with an outer porous layer can be varied, depending upon the desired clinical result. In general, although 100% coverage may be desired in certain circumstances, the outer porous layer may alternatively cover no more than about 90%, and in some embodiments no more than about 75%, and in further embodiments no more than about 50% of the total surface area of the implant. The configuration of the porous outer layer may also be varied, such that it may be positioned on end zones of the implant, positioned in a central zone on the implant, or distributed throughout such as by a spiral winding, spaced apart transverse rings, checker board pattern, or otherwise.

When the porous layer is provided as a spiral winding, or as a series of transverse circles surrounding the implant, the implant may more readily expand and contract in an axial direction, while maintaining a constant cross sectional profile. In general, the materials utilized for the porous layer (e.g. ePTFE) are less compliant than materials useful for the inner layer. As a consequence, elongation of the implant as a result of over inflation, or compression of one end of the implant will allow axial stretching or expansion of the implant without being constrained by the porous layer. This may among other objectives help provide a natural feel, upon manual palpation of the implant from the surface of the skin.

Within the outer layer 150 is an inner layer 152, which provides a fluid-tight seal and, along with the valve assembly, enables the implant to be inflated and to maintain its inflation. This inner layer 152 is preferably formed from an elastomer, such as dimethylsiloxane (silicone) or polyurethane, and more preferably from an elastomer with a durometer between about 40-00 and 80-A on the Shore hardness scales. This enables the implant to not only be soft and flaccid upon presentation of an initial deforming force but to also have "cushioned stop" when the deformation exceeds the amount that the flaccidity is able to absorb. This inner layer 152 of the implant can also be made of inextensible materials thus relying completely on its flaccidity in order to present mechanical softness; this is particularly suitable in implant locations that are in deeper tissue planes, such as against the periosteum or against bone. The filler 154, is within the inner layer 152.

Figure 23C:
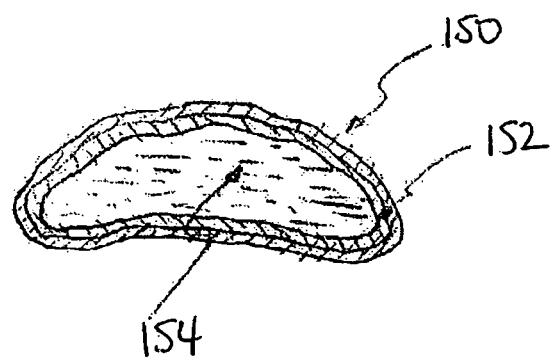
FIG. 23C illustrates a cross-sectional view of a nasolabial implant inflated to less than the maximally recommended fill volume, near its distal end, according to one embodiment of the invention.

FIG. 23C is a cross-section of the embodiment of FIG. 23A in which the physician has chosen to inflate the implant to a level below the maximum recommended inflation volume. This creates a markedly flaccid implant that even further conforms to the pocket with the tissue bed created by the physician during implantation. This conformability and flaccidity allows the implant to "blend" with the surrounding tissue in terms of its mechanical properties, and renders it very difficult to palpate. The materials of the implant are generally of an optically clear nature, particularly once in contact with body fluids, and the soft, flaccid shape does not cause it to impart a protrusion on the skin surface; thus the implant is invisible to the eye and very difficult to detect by palpation. Invisibility of detection to the eye and difficulty of palpation are desirable characteristics of implants in cosmetic and reconstructive surgery.

Figure 23D:
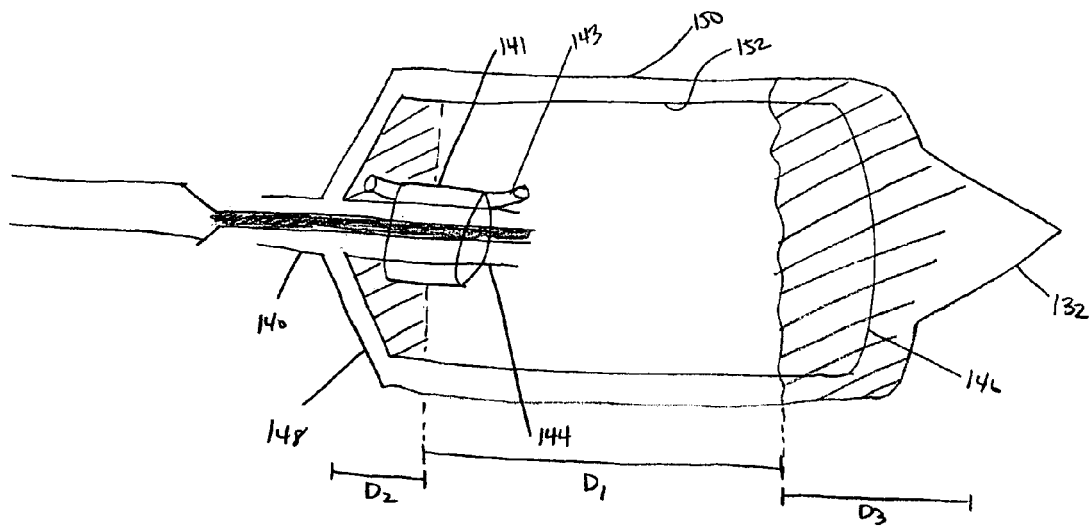
FIG. 23D is a view of a valve assembly within an embodiment of an inflated nasolabial implant, and illustrates the dual layer, bonded, and unbonded areas.

FIG. 23D shows a preferred nasolabial implant and various preferred characteristics. The implant contains both the inner layer 152 made of preferably silicone, and an outer layer 150 which may be made of, for example, ePTFE. There is a proximal bonded zone D2 and distal bonded zone D3 shown shaded, where the inner layer 152 and outer layer 150 are bonded such as by the use of a silicone adhesive. The axial lengths D2 and D3 may be identical, or may be different lengths in different embodiments. Furthermore, there may be a central zone without bonding D1 where the inner layer 152 and outer layer 150 can "slip" and allow for flotation of the inner layer 152 with respect to the outer layer 150. A desirable implant will have compliance matching with the surrounding native tissues to provide a more natural feel and appearance. This unbonded zone D1 allows for elongation of the ePTFE outer layer construct 150 as well as the inner layer 152 which will serve to increase the compliance of the implant. The axial length D1 of the unbonded zone may be anywhere between about 0.5-14 cm, preferably about 1-10 cm, 1.5-6 cm, and often between about 2-4 cm. The length D1 of the unbonded zone may be at least about 10%, 20%, 50%, 67%, 75%, or more of the overall implant length in some embodiments.

The implant is preferably impermeable or minimally permeable to vapor or liquid at physiologic temperatures. Depending on the desired long-term stability of the implant, it may be desirable to add one or more additional layers. This may be desirable, for example, to inhibit permeability at physiologic pressures and temperatures, and thus premature deflation.

Figure 24A:
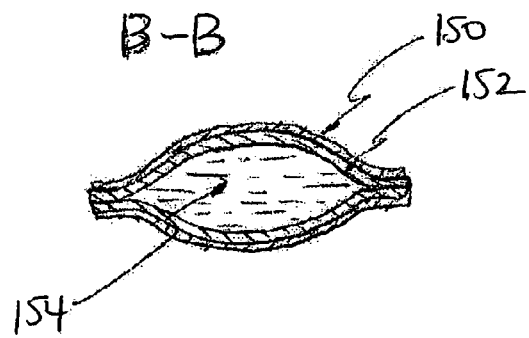
FIG. 24A is a cross-sectional view of a nasolabial implant fully inflated as recommended, near its proximal end according to one embodiment of the invention.
Figure 24B:
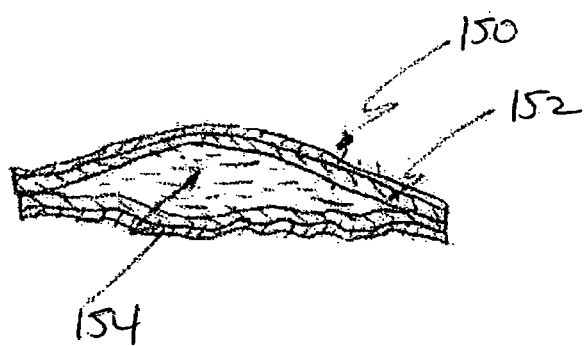
FIG. 24B is a cross-sectional view of a nasolabial implant inflated to less than the maximally recommended fill volume, near its proximal end according to one embodiment of the invention.

FIG. 24A shows a cross-section of the proximal taper 148 of the embodiment of FIG. 22. Note the flattened cross-section that enables the proximal portion to better "feather" into the zone of the nasolabial groove that is close the oral commissure. FIG. 24B shows the effect on the proximal end of inflating the implant of the embodiment of FIG. 24A to a level below the maximum recommended inflation volume, creating a markedly flaccid implant with the same aforementioned advantages.

Figure 25:
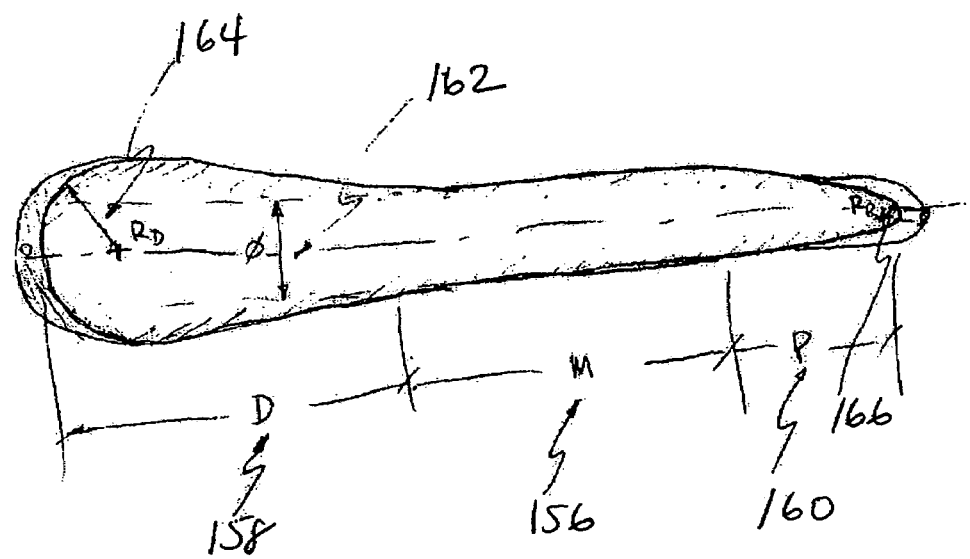
FIG. 25 shows a general shape of an advantageous nasolabial implant in which the distal end is to the left and the proximal end to the right according to one embodiment of the invention.

FIG. 25 illustrates the general shape of an advantageous nasolabial implant in which the distal zone 158 is to the left and the proximal zone 166 to the right, according to one embodiment of the invention. As previously described, it is advantageous for the distal zone 158 to be generally bulbous while the proximal zone 166 is generally a flattened triangular taper. The general size of the implant can be characterized by its diameter 162 which would be measured at the maximum recommended inflation volume when the cross-section would be generally circular and which will characterize the middle zone 156 of the implant. The distal tapered zone 158 can be characterized by its radius of curvature 164 based upon a best fit curve, which can be larger than one-half the diameter 162, thus creating a marked bulbuosity to the distal end zone 158 of the implant. This may be advantageous in patients with particularly deep nasolabial folds, especially in the perialar region. The proximal zone 160 is of a generally triangular shape within the plane of the proximal tab 140 and can be characterized by the length of the tapered zone 160 and the best fit radius of curvature of the interior edge of the seam at the proximal tip 166. The length 160 is, in a preferred embodiment, between one-tenth and six-tenths the length of the middle zone 156. The length of the distal region 158 is, in a preferred embodiment, between one-tenth and six-tenths the length of the middle zone 156.

The following is a preferred method of assembling a nasolabial implant, according to one embodiment of the invention. This method will produce a preferred 4.5 mm diameter implant with one tapered end, end lamination of silicone and ePTFE tubing, and 50% silicone tubing pre-stretch. Preferred implants constructed in this method are 2 cm, 3 cm, or 4 cm in axial length when inflated.

Figure 26A:
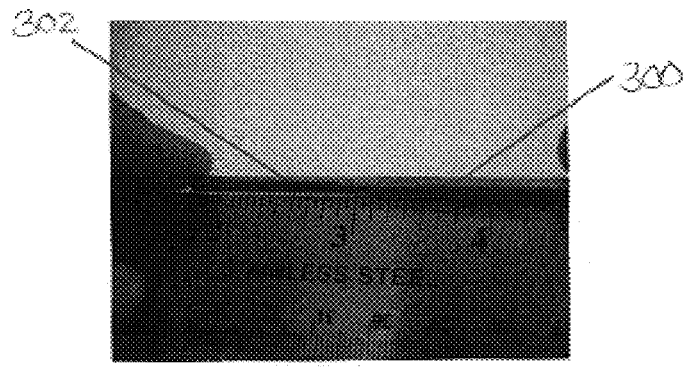
FIG. 26A illustrates a step in creating an implant lamination subassembly where silicone tubing is slipped over an ePTFE mandrel, according to one embodiment of the invention.
Figure 26B:
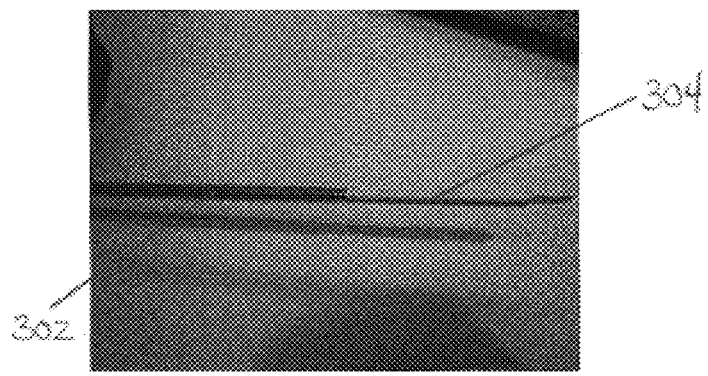
FIG. 26B illustrates a step in creating an implant lamination subassembly where ePTFE tubing is slid over the small diameter end of a mandrel until aligned with the silicone tube end, according to one embodiment of the invention.
Figure 26C:
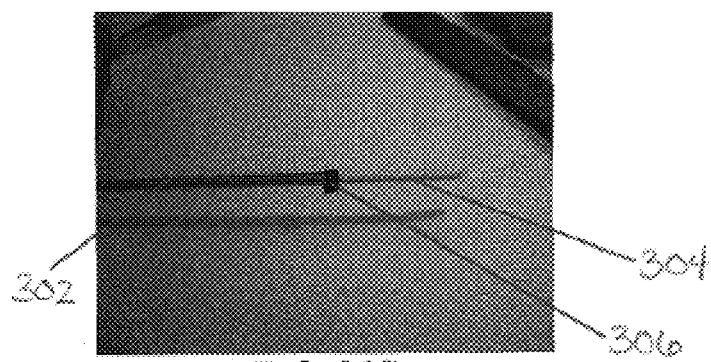
FIG. 26C illustrates a step in creating an implant lamination subassembly where a shrink tube is placed over the end of the ePTFE tubing, according to one embodiment of the invention.
Figure 26D:
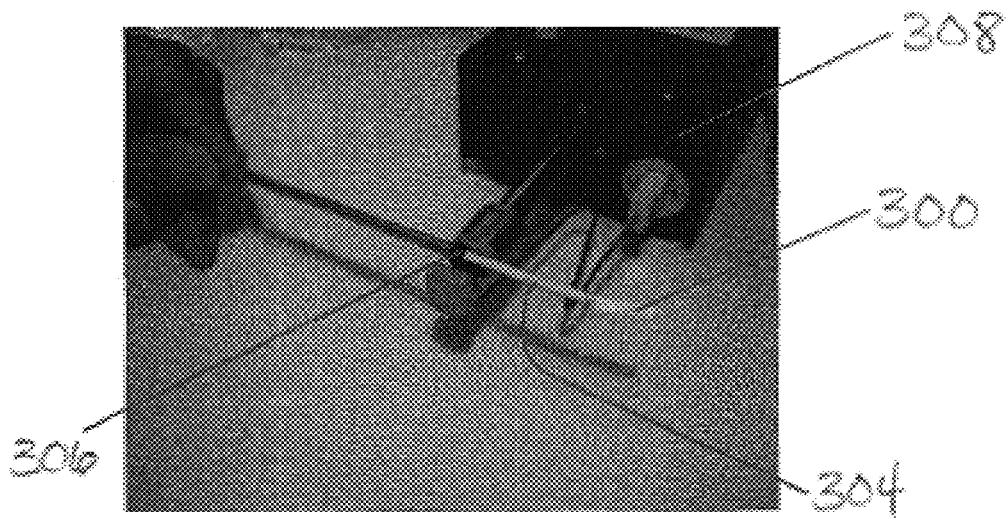
FIG. 26D illustrates a step in creating an implant lamination subassembly where heat is applied until the tube is shrunk down using an hot box, according to one embodiment of the invention.
Figure 26E:
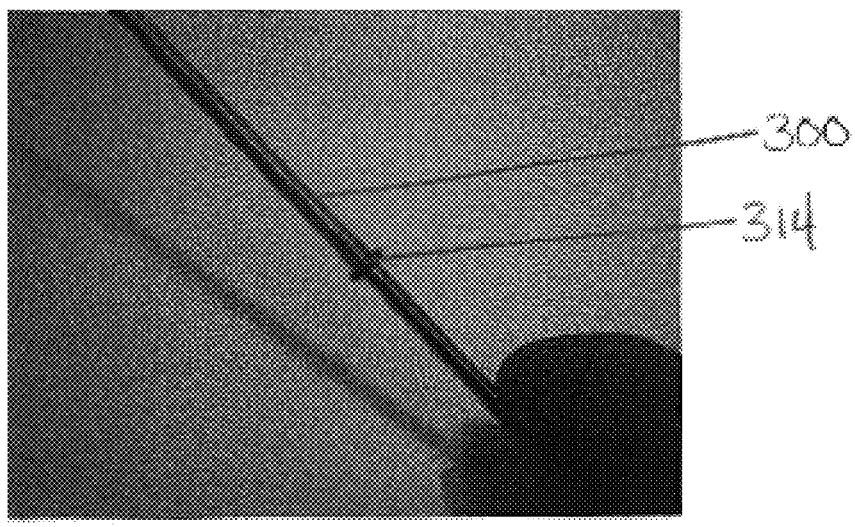
FIG. 26E illustrates a step in creating an implant lamination subassembly after application of heat to the shrink tube, and application of an O-ring.
Figure 26F:
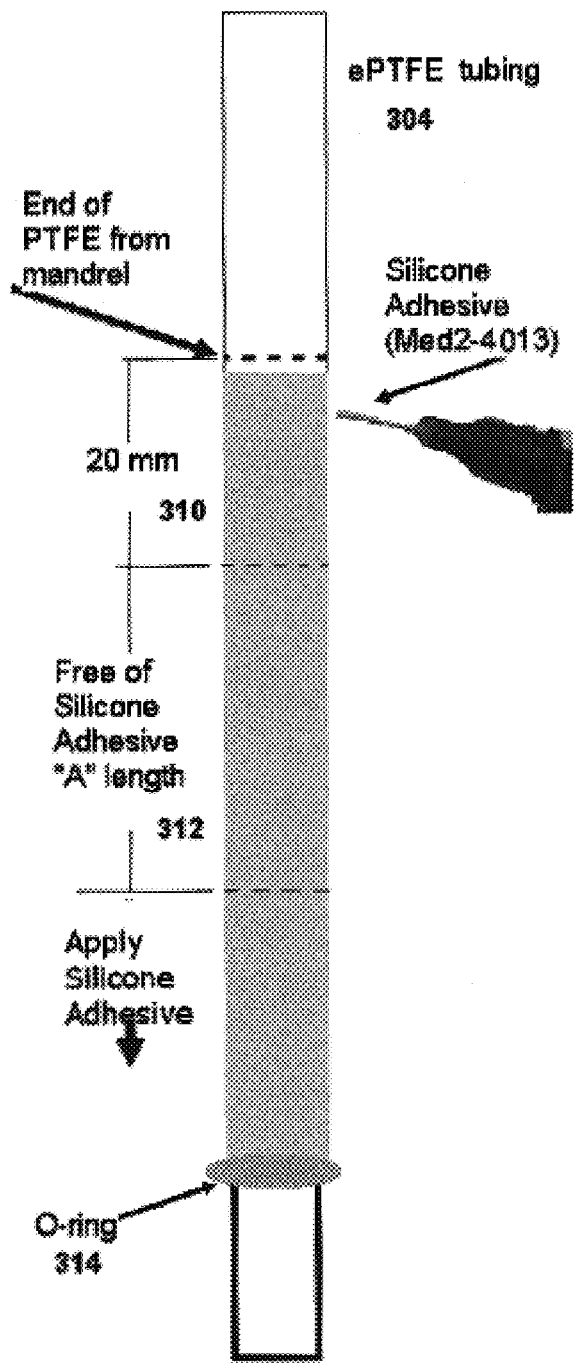
FIG. 26F is a schematic diagram showing application of silicone adhesive relative to various other components of a lamination subassembly, according to one embodiment of the invention.

The first step of assembling the nasolabial implant is to construct a lamination subassembly. A piece of 0.160" ID×0.004" wall silicone tubing 300, 50% stretch, is cut to a length of 2.90 inches. Next, the ePTFE tubing 304 is cut to a length of 4.5 inches. The silicone tubing 300 is then slipped over the PTFE mandrel 302 until the proximal end of the silicone tubing 304 is about 0.125 inches from the PTFE end, as in FIG. 26A. Next, a piece of shrink tube ⅛ inch long is cut. The ePTFE tubing 304 is then slid over the small diameter end of the mandrel 302, until it is aligned with the silicone tube end, as in FIG. 26B. FIG. 26C shows the shrink tube 306 placed over the end of the ePTFE tubing 304. Heat is then applied, as in FIG. 26D, until the tube is shrunk down using a hot box 308 set at a temperature of 335-345° F., more preferably 340° F., and 35-45 SCFH. The shrink tube 306 is checked to ensure coverage of both the ends of the silicone 300 and ePTFE 304 tubing. Next, using lubrication, preferably 99% isopropyl alcohol (IPA), the silicone tube 300 is stretched until it reaches the distal end of the ePTFE mandrel 302 and held in place using an O-ring 314 applied with an O-ring fixture, as in FIG. 26E. Then, silicone adhesive, preferably Med 2-4213, is applied to the surface of the silicone tube. Preferably, as in FIG. 26F, adhesive is applied about 20 mm from one end of the PTFE covered mandrel. Depending on the length of implant desired, an adhesive free area 312 may be left in the central portion of the tube to create the central zone without bonding D1 shown in FIG. 23D with the advantages of such a zone noted previously. A 30 mm length of adhesive free area is preferred for a 4 cm length implant and 20 mm length adhesive free area for a 3 cm implant. However, no adhesive free area is preferred for a 2 cm implant; the adhesive should be applied to the entire surface of the silicone tube 300 to achieve full lamination for that particular embodiment.

Pre-stretching the inner tubular layer compared to the outer layer allows the implant to exhibit axial elongation in use, such as under manual pressure from the surface of the skin. This is because the implant once released from the manufacturing fixtures will axially shorten, as the inner layer reverts to its resting configuration. This will cause a microscopic or small scale accordion effect on the outer ePTFE layer. The implant may thereafter be axially elongated by compressing one end, or by over inflation, without the need for a compliant material as the outer layer. Elongation of the inner layer relative to its resting state of at least about 10%, often at least about 25%, and in some embodiments between about 30% and about 70% may be used.

FIG. 26G shows adhesive being applied to the end of the silicone tube 300. Following application of the adhesive, the tube is smoothed with a clean room foam swab. The ePTFE 304 is then everted over the silicone tube using plastic tweezers 316, as in FIG. 26H and tape 318, preferably Transpore tape, or 3M Microfoam, as in FIGS. 26I-J. The silicone adhesive is then cured in a calibrated oven for at least 20 minutes at 145-155° C. using the fixture, ceramic mandrel holder, and oven as well as a timer, preferably a digital timer. Next, the adhesive is allowed to cool for approximately 5 minutes. The tied ends are then trimmed and removed from the mandrel 336. Lubrication, preferably 99% IPA, is then applied. Next, the lamination subassembly created is visually inspected. A device is rejected if there are gaps between the ePTFE and the silicone tubing inside, there are loose areas of ePTFE in the laminated region that are not attached to the silicone tubing, or excessive wrinkling and/or discoloration is observed. If the device is not rejected, the lamination may be sealed proximally.

Figure 27B:
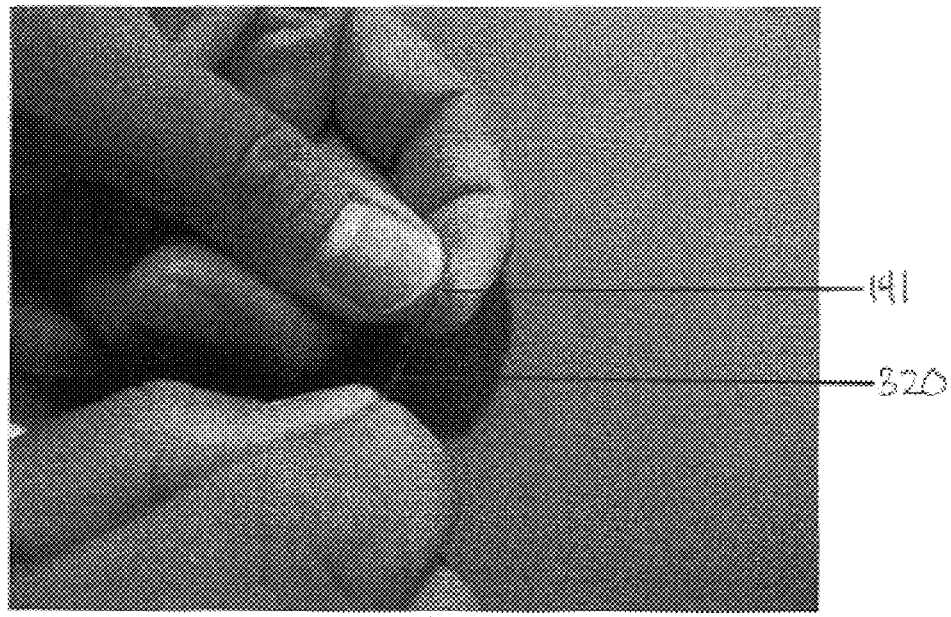
FIG. 27B shows a step in creating an implant valve subassembly, where a valve tube is slid onto a small needle, according to one embodiment of the invention.
Figure 27C:
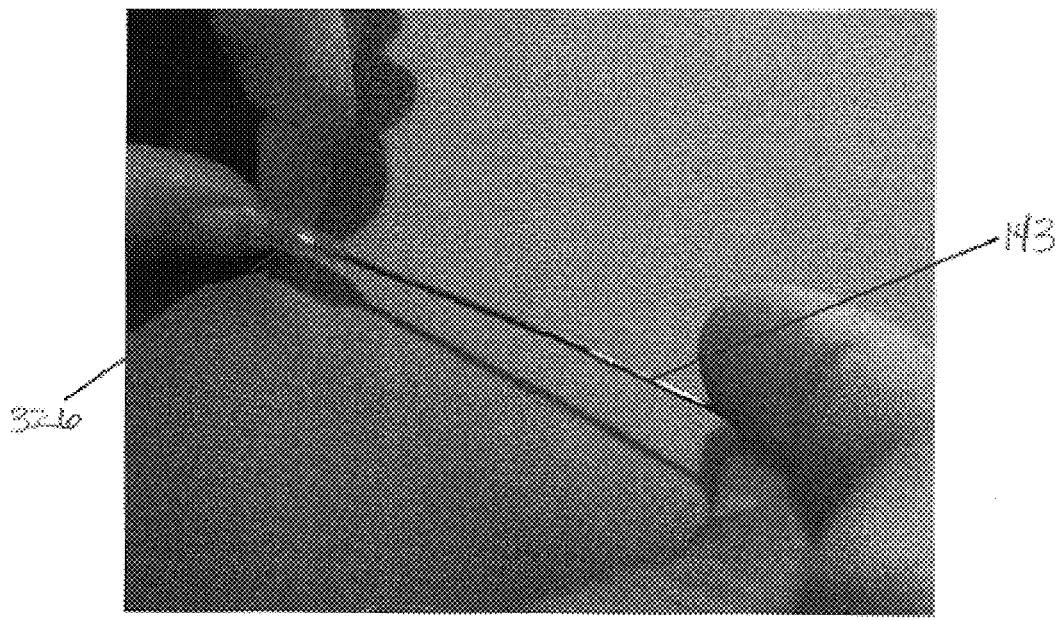
FIG. 27C shows a step in creating an implant valve subassembly, where the tip of the small needle is then inserted into the tip of a 20-gauge precision dispense tip, according to one embodiment of the invention.
Figure 27D:
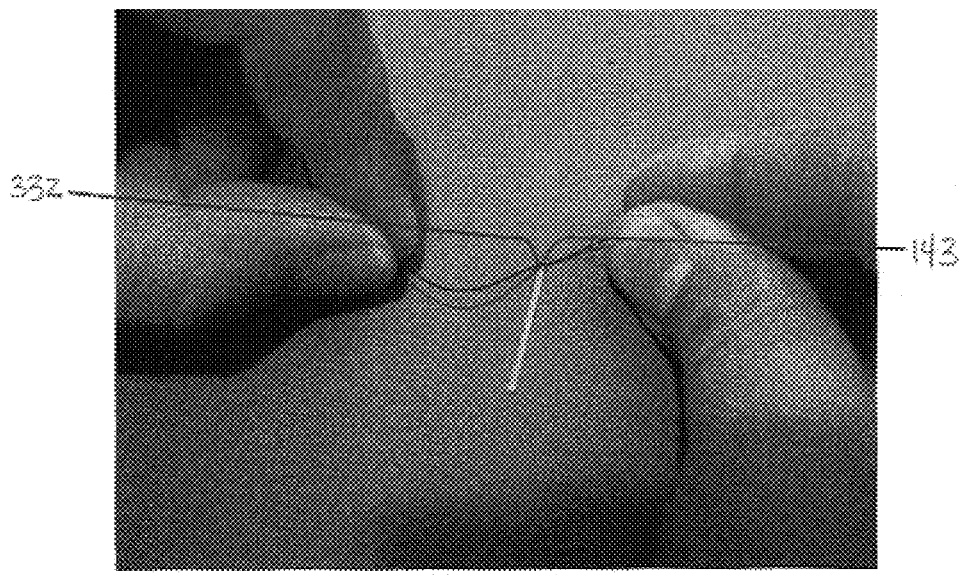
FIG. 27D shows a step in creating an implant valve subassembly, where a half-hitch knot is tied around the end of a valve plug, according to one embodiment of the invention.
Figure 27E:
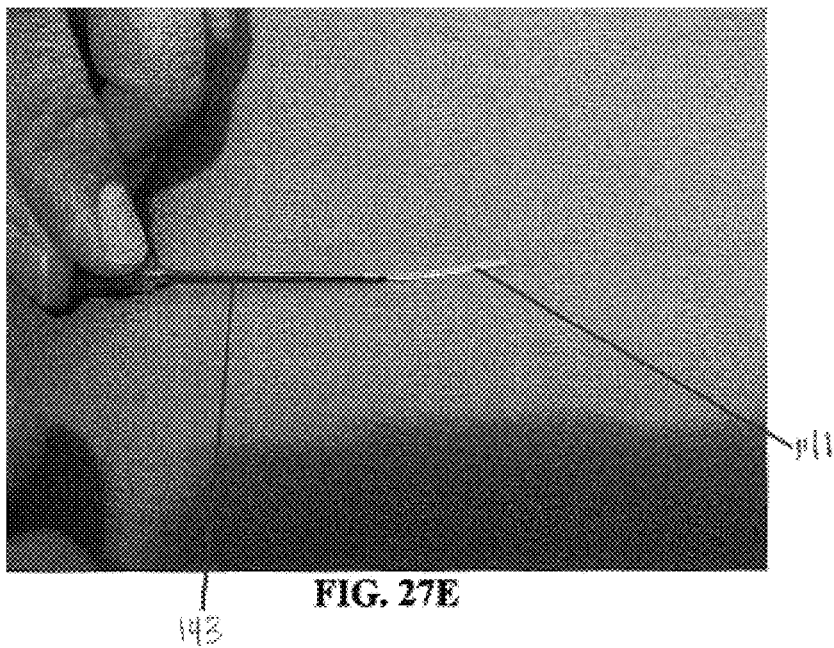
FIG. 27E shows a step in creating an implant valve subassembly, where the valve tube is slid onto the valve plug, according to one embodiment of the invention.
Figure 27F:
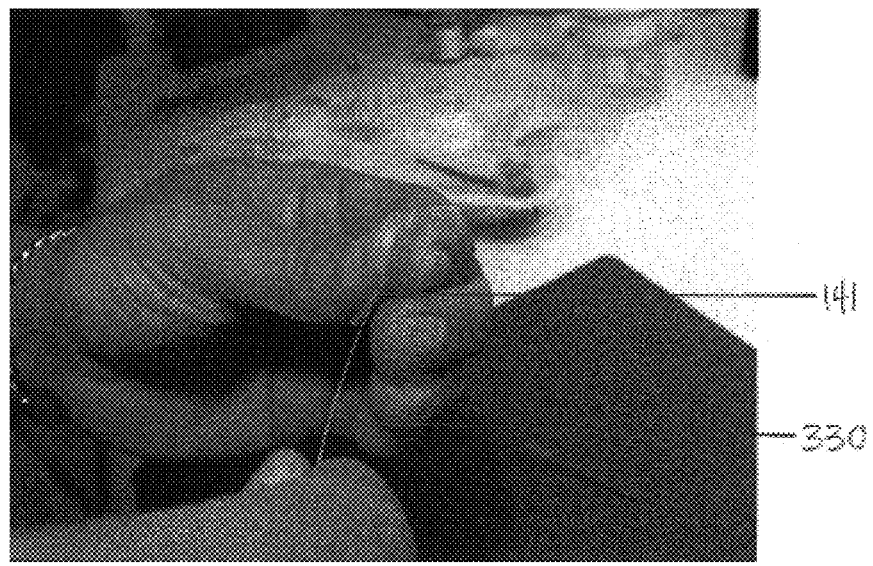
FIG. 27F shows a step in creating an implant valve subassembly, where a mandrel is inserted into the valve tube, according to one embodiment of the invention.

The next step is to create an implant valve subassembly 346. FIG. 27A illustrates various components that may be utilized in this process. First, a valve tube 141 is cut to a length of 0.30 inches. The valve tube 141 is then slid onto a 0.0345 inch diameter small needle 320, as in FIG. 27B. The tip of the small needle 320 is then inserted into the tip of a precision dispense tip, preferably a 20-gauge precision dispense tip 322, more preferably a pink EFD tip, as in FIG. 27C. The valve tube is then transferred to the 20-gauge precision dispense tip 322. Next, the tip of a 0.0415 inch diameter large needle 324 is inserted into the tip of the 20-gauge precision dispense tip 322, and the valve tube 141 is then transferred to the large needle 324. The tip of the large needle 324 is then inserted into an 18-gauge precision dispense tip 326, preferably a green EFD. Next, a valve plug 143 is cut to a length of approximately 1 inch. Using 4-0 silk suture 328, a half-hitch knot 332 is tied around the end of the valve plug 143, as in FIG. 27D. The suture 328 is then threaded through the 18-gauge precision dispense tip 326 and the valve plug 143 is carefully pulled into the shaft, as in FIG. 27E. The valve 141 tube is then slid onto the valve plug 143 by simultaneously removing the removing the valve plug 143 from the shaft and pushing the valve tube 141 off the shaft, as in FIG. 27F.

Figure 27G:
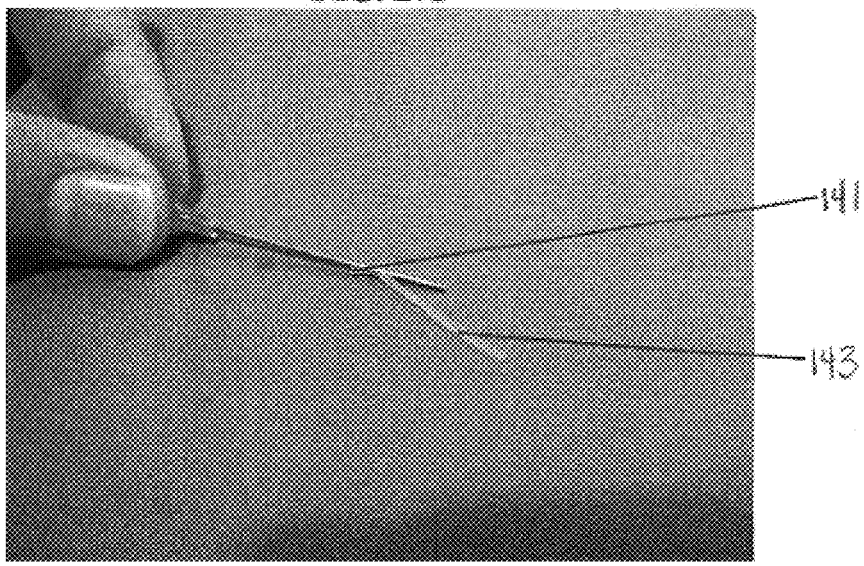
FIG. 27G shows a step in creating an implant valve subassembly, where the trimmed valve plug protruding from the valve tube, according to one embodiment of the invention.

Next, the valve tube 141/valve 143 plug subassembly is manipulated so that there is no bunching and minimal bending. A 0.016 inch mandrel 330 is then carefully inserted into the valve tube 141. Alternatively, a 0.018 inch mandrel may be utilized. The mandrel 330 is slid through, taking care not to damage the valve tube 141 or valve plug 143. With the mandrel 330 still in the valve tube 141, the mandrel 330 is inserted into the 20-gauge precision dispense tip 322. The 20-gauge precision dispense tip 322 shaft is then slid into the valve tube 141 without pushing out the valve plug 143. The mandrel 330 is then removed. FIG. 27G shows the valve plug 143 trimmed so that it protrudes approximately 1.5 mm from each end of the valve tube 141.

Figure 27H:
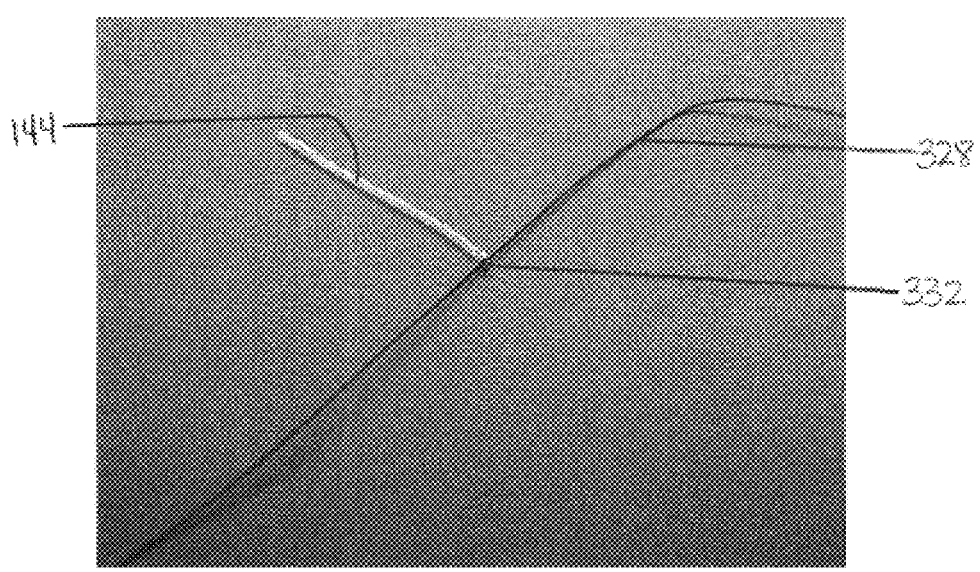
FIG. 27H shows a step in creating an implant valve subassembly, where a half-hitch knot is tied around the free end of the neck tube.
Figure 27I:
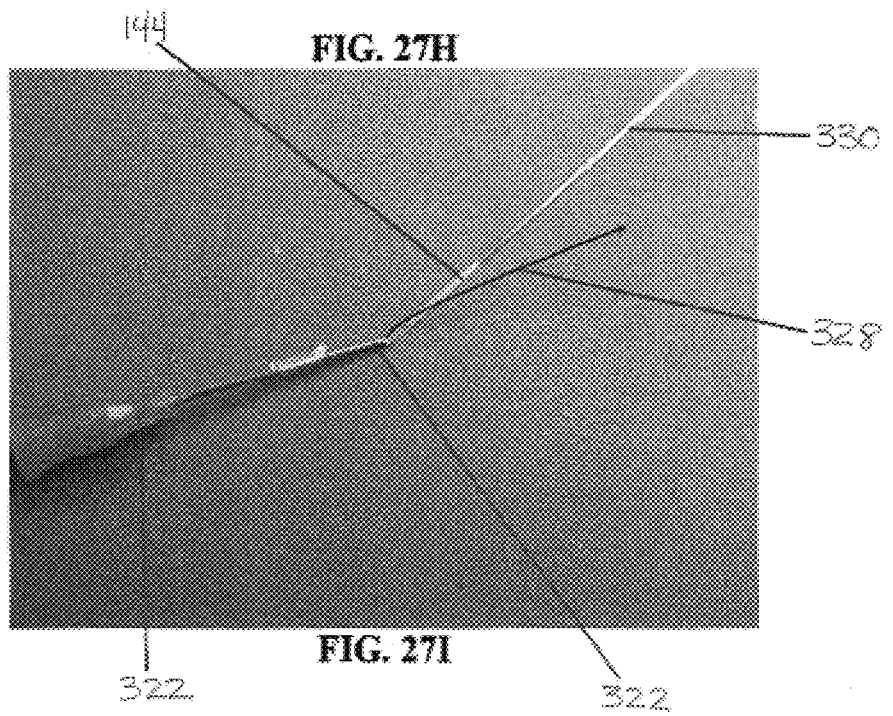
FIG. 27I shows a step in creating an implant valve subassembly, where a suture is threaded onto a precision dispense tip, and the neck tube is drawn into the shaft until the precision dispense tip and the mandrel abut each other.

A neck tube 144 is then cut to 1.5 inches in length. Using the 4-0 silk suture 328, a half-hitch knot 332 is tied around the free end of the neck tube 144, and the free end of the neck tube 144 is slid halfway onto the mandrel 330, as in FIG. 27H. Next, shown in FIG. 27I, the suture 328 is threaded onto the 20-gauge precision dispense tip 322, and the neck tube 144 is drawn into the shaft until the precision dispense tip 322 and the mandrel 330 about each other.

Figure 27J:
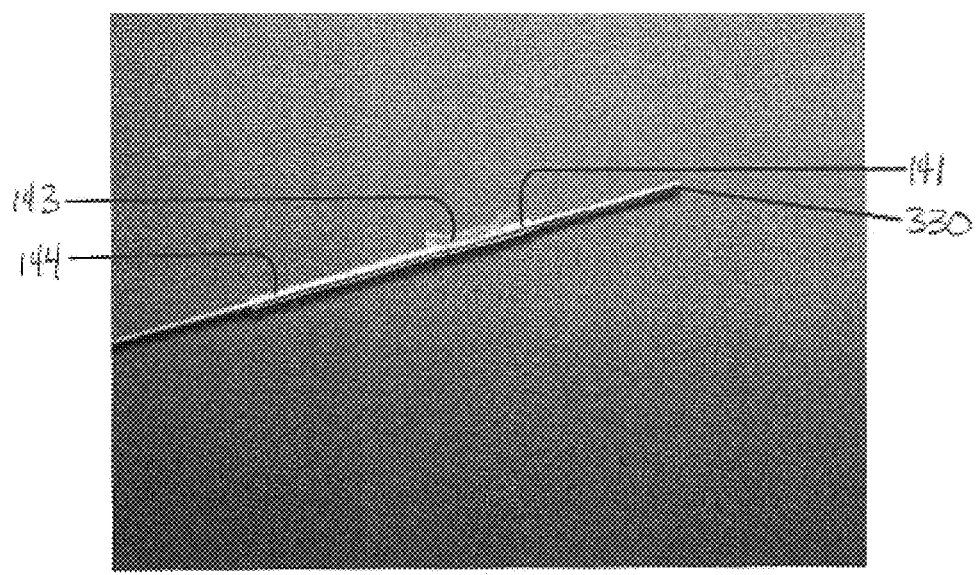
FIG. 27J illustrates a completed valve subassembly, according to one embodiment of the invention.

The valve tube 141/valve 143 plug subassembly is then transferred onto the neck tube 144 by simultaneously removing the neck tube 144 from the shaft 322 and pushing the valve tube 141/valve 145 plug subassembly off the shaft 322. Next, the tied portion of the neck tube 144 is cut off, leaving the free suture 328 inside the valve tube 141. The valve tube 141/valve 143 plug assembly is then stabilized with fingers, and the mandrel 330 is slowly slid through the subassembly taking care not to damage the valve tube 141, valve plug 143, or neck tube 144. The suture 328 is then used to straighten out the valve plug 143 and to remove any bunches in the valve tube 141. The suture 328 is then slowly removed without moving the valve plug 143. The neck tube 144 is then trimmed so that it extends past the valve tube by approximately 2 mm on one side, and 15 mm on the other side. Finally, the completed valve subassembly 346, shown in FIG. 27J, is visually inspected, and rejected if any of the following characteristics are present: holes in the valve 141 or neck tubes 144, particulate and foreign materials inside the valve tube 141, the valve plug 143 does not protrude from the valve tube 141 at both ends, or the valve tube 141 is excessively bunched up.

Figure 28A:
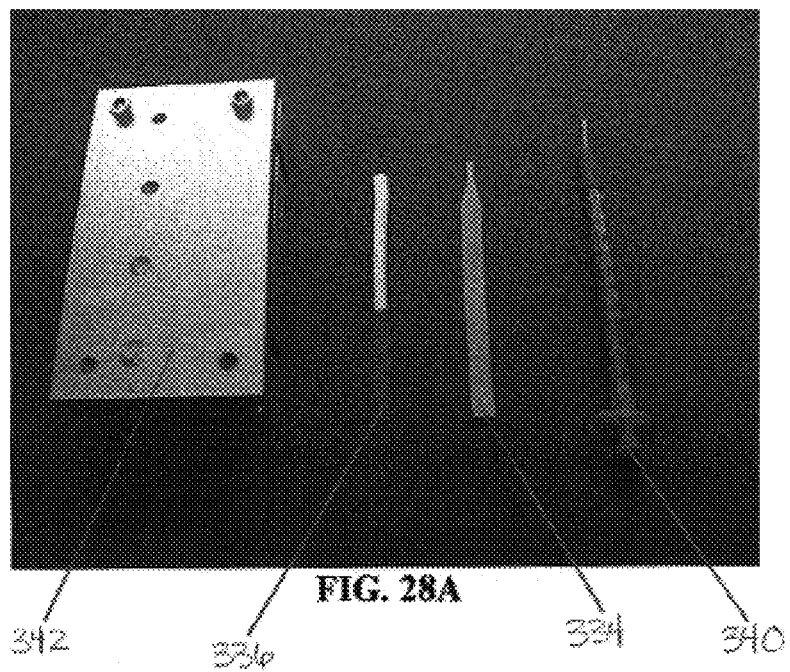
FIG. 28A illustrates various components utilized to seal the proximal end of the lamination subassembly, according to one embodiment of the invention.
Figure 28B:
FIG. 28B illustrates a step in sealing the proximal end of the lamination subassembly, where a proximal shim is inserted into the lamination subassembly.
Figure 28C:
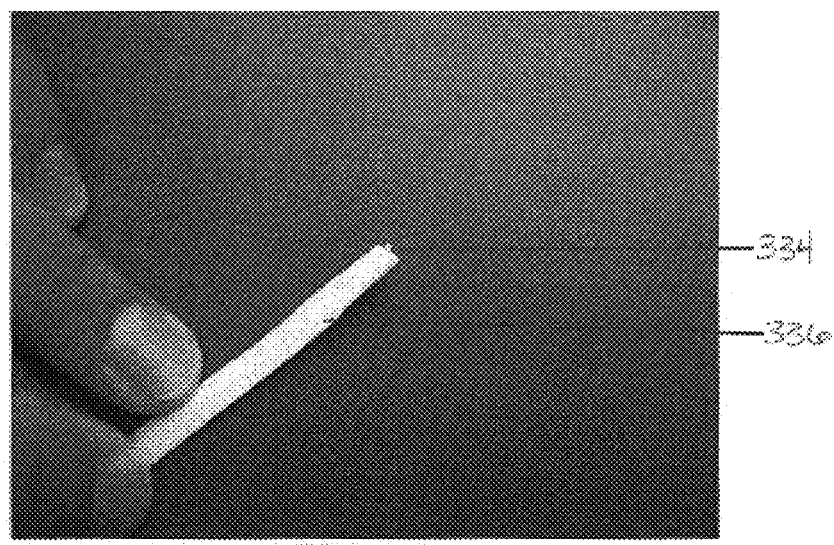
FIG. 28C illustrates a step in sealing the proximal end of the lamination subassembly, where the neck of the proximal shim is aligned to be parallel to the axis of the lamination subassembly.

The next step is to seal the proximal end 335 of the lamination subassembly 336. Various components utilized in sealing the proximal end 335 are shown in FIG. 28A. First, the subassembly 336 is inspected to ensure the absence of moisture and that the lubricant 336 has evaporated. A proximal shim 334 is then inserted into the lamination subassembly 336 by lightly bending it lengthwise, as in FIG. 28B. The proximal shim 334 is inserted until the neck protrudes out approximately 2 mm, and the lamination subassembly 336 is then smoothed out so that the proximal shim 334 fits snuggly inside. The neck of the proximal shim 334 is then aligned, as in FIG. 28C, so that it is parallel with the axis of the lamination subassembly 336, making sure the shim 334 is centered within the subassembly 336.

Figure 28D:
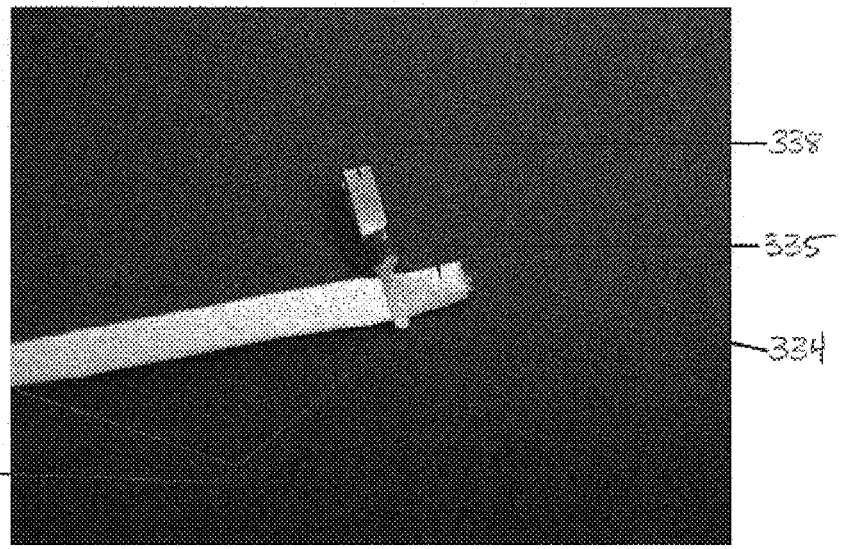
FIG. 28D illustrates a step in sealing the proximal end of the lamination subassembly where a hard jaw clamp is placed across the lamination subassembly.
Figure 28E:
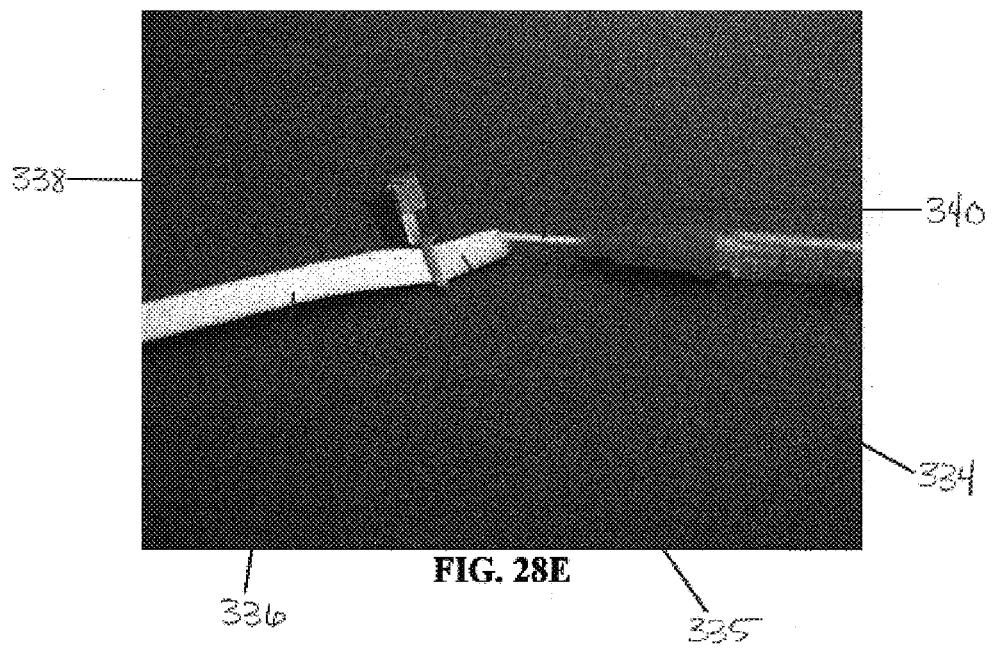
FIG. 28E illustrates a step in sealing the proximal end of the lamination subassembly where the end of the lamination subassembly is filled with adhesive.
Figure 28F:
FIG. 28F illustrates a step in sealing the proximal end of the lamination subassembly where the adhesive in the lamination subassembly is smoothed out with fingers.
Figure 28G:
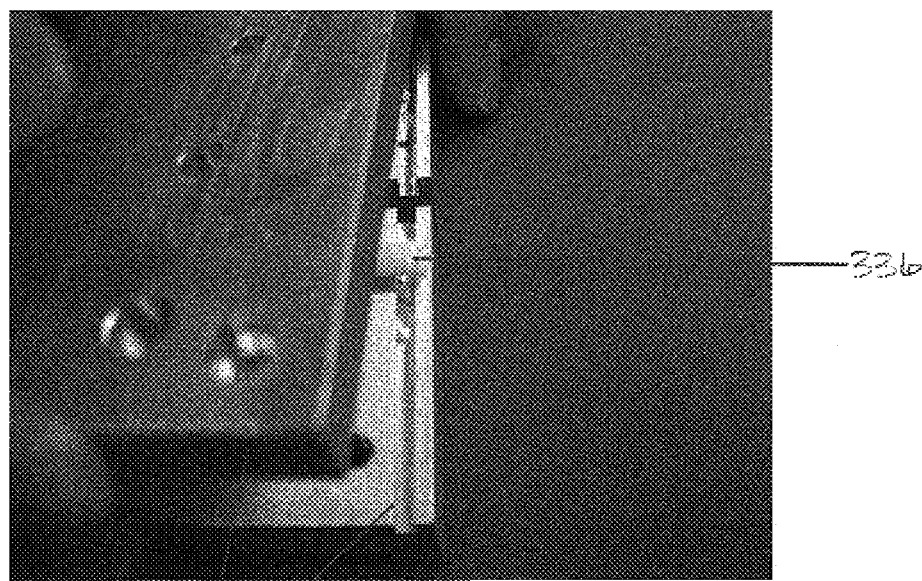
FIG. 28G illustrates a step in sealing the proximal end of the lamination subassembly where the lamination subassembly is placed on a proximal seal fixture.

Next, shown in FIG. 28D, a hard jaw clamp 338 is placed across the lamination subassembly 336 approximately 1 cm from the end. The end of the lamination subassembly 336 is then filled with adhesive 340, preferably MED2-4213 adhesive, as in FIG. 28E spreading the adhesive around the proximal shim 334. Next, as in FIG. 28F, the adhesive is lightly smoothed out with fingers over the proximal shim 344 and the excess wiped off using a lint-free wipe. The hard jaw clamp 338 is then removed and the lamination subassembly 336 is placed on a proximal seal fixture. Two or more 0.020 inch mandrels are then inserted as shims between the two pieces of the proximal seal fixture 342, shown in FIG. 28G. The top is then screwed down without distorting or creasing the device.

Figure 28H:
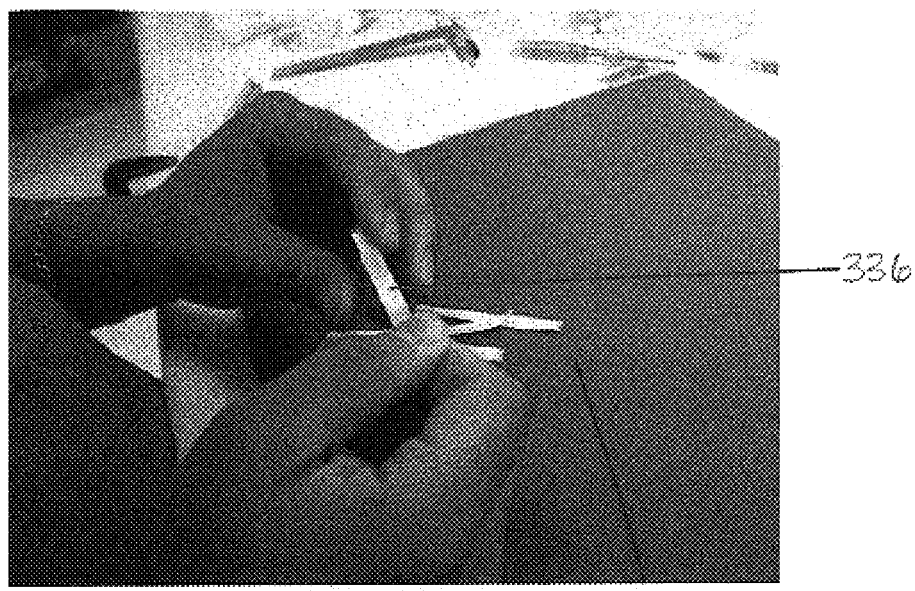
FIG. 28H illustrates a step in sealing the proximal end of the lamination subassembly where the proximal shim is removed from the lamination subassembly.

The lamination subassembly 336 is then cured in a calibrated oven for a minimum of 45 minutes at a temperature of 145-155° C. The fixture 342 is then removed from the oven and placed on the copper cooling plate. Next, as shown in FIG. 28H, the proximal seal fixture 342 is blown with a cold air vortex tube as needed and the fixture 342 is allowed to cool before removing the lamination subassembly 336. Next, the proximal shim 334 is carefully removed from the lamination subassembly 336 and a razor blade is used to trim off excess silicone adhesive from the end. Lastly, the subassembly 336 is inspected and devices that exhibit significant asymmetry in the proximal tab, noticeable adhesive failure, excess adhesive migration into the expandable membrane, or cuts or tears in the expandable membrane are rejected.

Figure 28I:
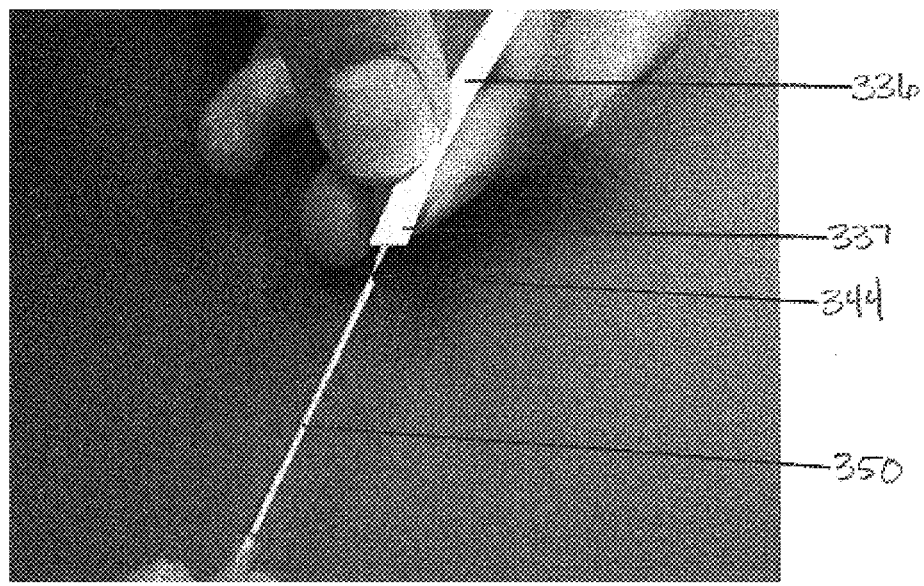
FIG. 28I illustrates a step in inserting the valve subassembly into the lamination subassembly where a hypo tube is inserted into the lamination subassembly.
Figure 28J:
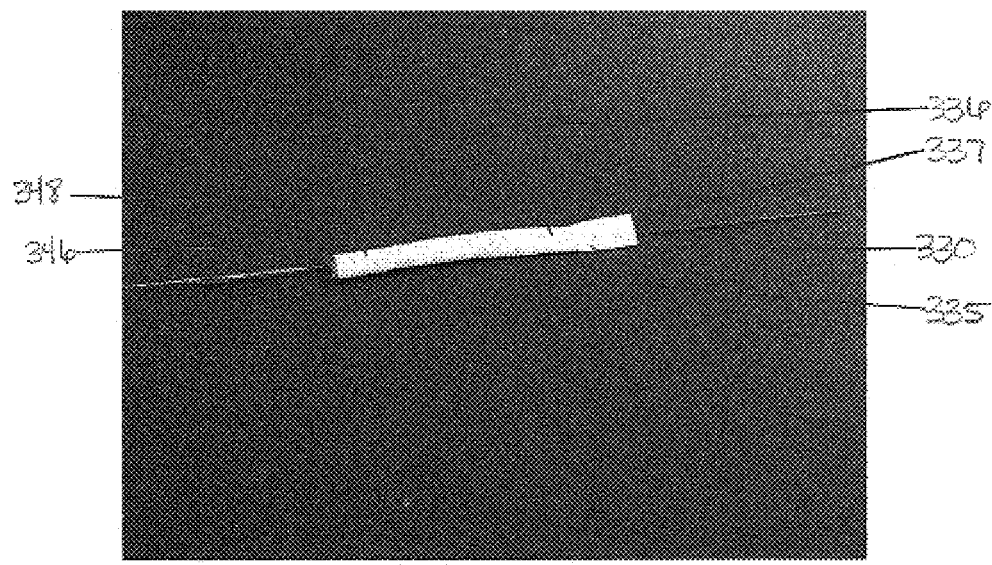
FIG. 28J illustrates a mandrel with valve subassembly in the lamination subassembly.

The next step is to insert the valve subassembly 346 into the lamination subassembly 336. A 0.030 inch mandrel 334 is first inserted into the distal end 348 of the lamination subassembly 336. Next, the 0.030 inch mandrel 334 is slowly slid into the neck of the proximal seal 337. As in FIG. 28I, a hypo tube 350 is then placed while the 0.030 inch mandrel is protruding from the end proximal 335 of the lamination subassembly 336. The hypo tube 350 is then carefully inserted into the neck of the lamination subassembly 336 until approximately 1 cm is in the device. While the hypo tube 350 is in the lamination subassembly 336, the 0.016 inch mandrel 330 (with the valve subassembly 346 on it) is slid onto the lamination subassembly 336 until the neck tube 144 is contained in the hypo tube 350, and the valve tube 141 abuts it, as in FIG. 28J. After this, the hypo tube 350 is then slowly removed from the lamination subassembly 336 while maintaining the position of the valve subassembly 346.

Figure 28K:
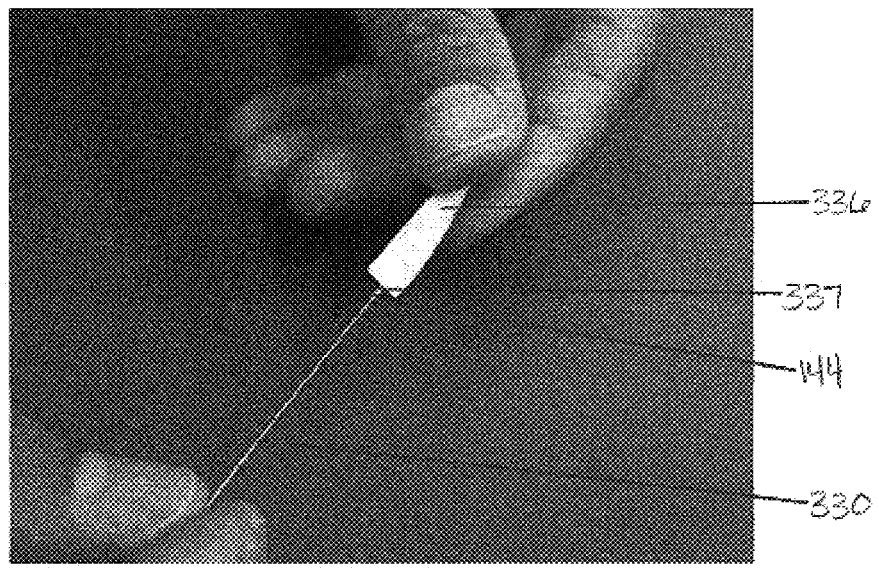
FIG. 28K illustrates the valve subassembly after withdrawal of the hypo tube, leaving the mandrel and neck tube contained in the neck of the proximal seal.
Figure 28L:
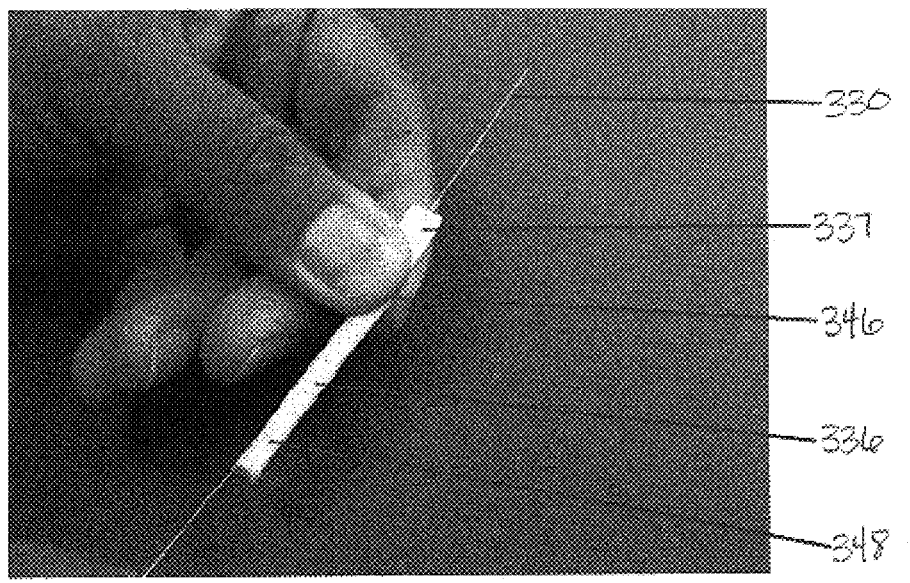
FIG. 28L illustrates a step in inserting the valve subassembly into the lamination subassembly where the mandrel is slid toward the distal end of the device without moving the neck tube or the valve subassembly.
Figure 28M:
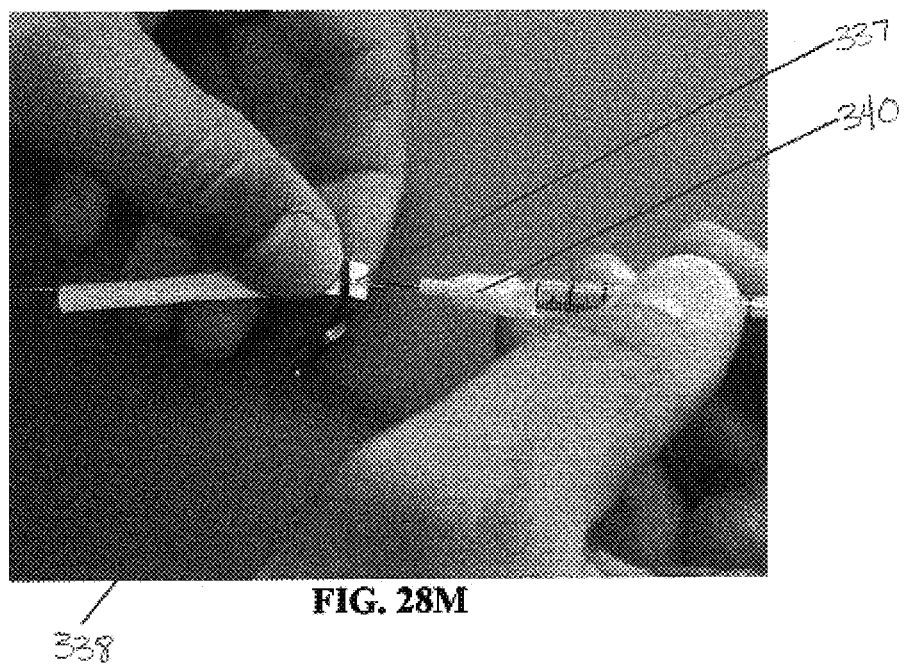
FIG. 28M illustrates a step in inserting the valve subassembly into the lamination subassembly where adhesive is placed into the proximal end of the device after placement of a hard jaw clamp.
Figure 28N:
FIG. 28N illustrates a step in inserting the valve subassembly into the lamination subassembly where a razor blade is used to trim the proximal tab along the proximal seal line.

Next, the hypo tube 350 is completely withdrawn, leaving the 0.016 inch mandrel 330 and the neck tube 144 contained in the neck of the proximal seal 337, shown in FIG. 28K. The valve subassembly 346 is then grasped through the lamination subassembly 336 and the 0.016 inch mandrel 330 is then slid through the distal 348 end of the device without moving the neck tube 144 or the valve subassembly 346, as in FIG. 28L. Then, the 0.016 inch mandrel 330 is then slid distally until it is approximately 6 mm from the proximal end 335 of the device. A hard jaw clamp 338 is then placed approximately 4 mm from the proximal end 335 of the device. Adhesive, preferably MED2-4213 adhesive 340, is then placed in between the neck tube 144 and the neck of the proximal seal 337, as in FIG. 28M. A second hard jaw clamp is then placed adjacent to the first hard jaw clamp 338, ensuring that it is approximately 2 mm from the proximal end 335 of the device. The lamination subassembly 336 is then placed in a calibrated oven and cured for a minimum of 20 minutes at between 145-155° C. Next, the ceramic oven fixture is removed and allowed to cool. The hard jaw clamps are then removed from the device. Using a razor blade 352 as in FIG. 28N, the proximal tab of the device is trimmed along the proximal seal line 337, to a width of approximately 1-1.5 mm.

Figure 28O:
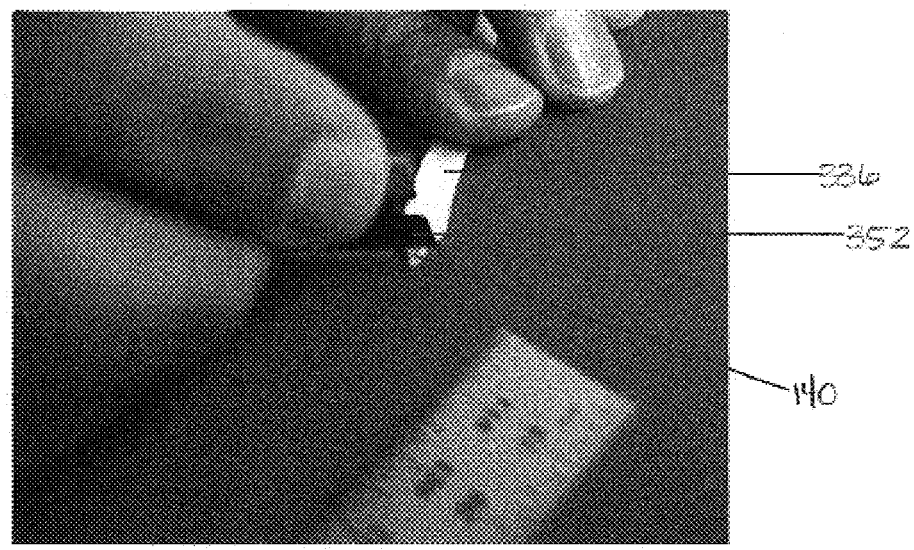
FIG. 28O illustrates a step in inserting the valve subassembly into the lamination subassembly where a portion of the proximal tab is cut off using a razor.

Next, as in FIG. 28O, approximately 1.5 mm of the length of the tip of the proximal tab 140 is cut off using a straight cut, perpendicular to the axis of the device. The 0.016 inch mandrel 330 is then carefully slid toward the proximal end 335 of the lamination subassembly 336, taking care to ensure that the valve subassembly 346 remains on the 0.016 inch mandrel 330. Lastly, the device is visually inspected for defects such as an excessively asymmetrical proximal tab, noticeable adhesive failures, loose, unbonded ePTFE on the proximal tab, excessive adhesive migration into the expandable membrane, and any cuts or tears in the expandable membrane.

Figure 29A:
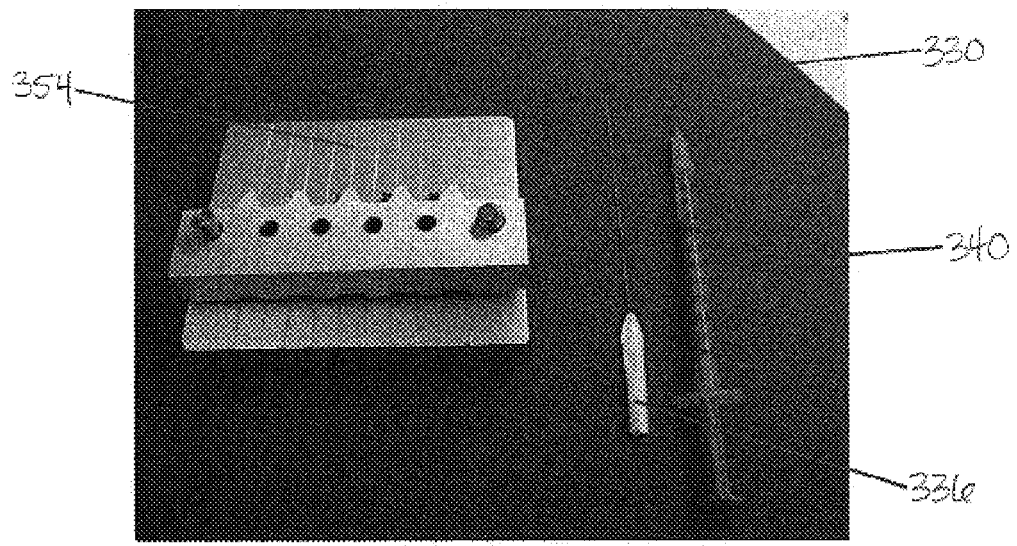
FIG. 29A illustrates various components utilizable to seal the distal end of the implant, according to one embodiment of the invention.
Figure 29B:
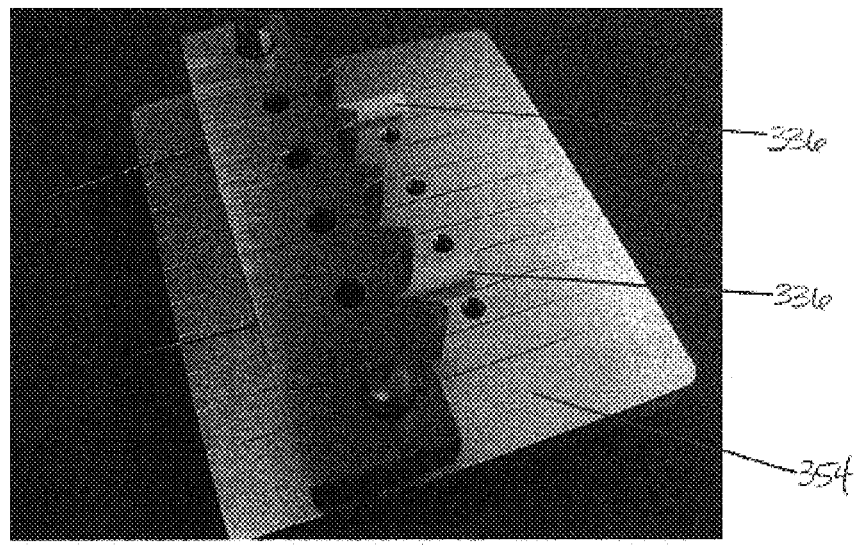
FIG. 29B illustrates the lamination subassembly being inserted into the distal seal fixture.
Figure 29C:
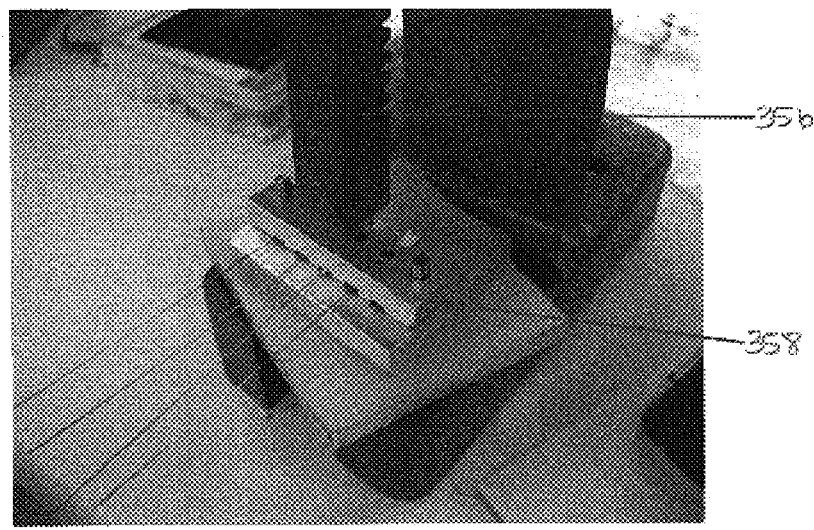
FIG. 29C illustrates the clamping plate being lowered and screwed into place, aided by an arbor press, after the lamination subassemblies are properly aligned.
Figure 29D:
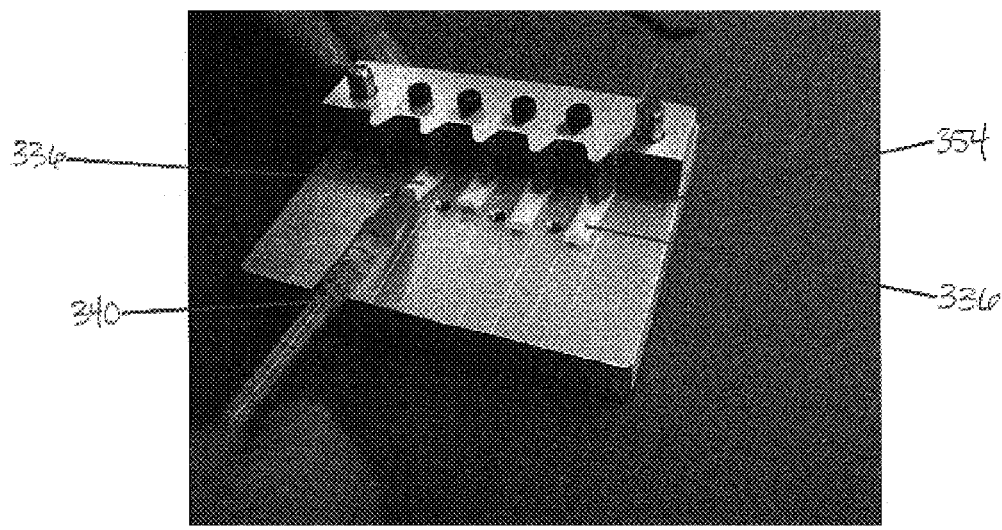
FIG. 29D illustrates the open end of a lamination subassembly being filled with adhesive.
Figure 29E:
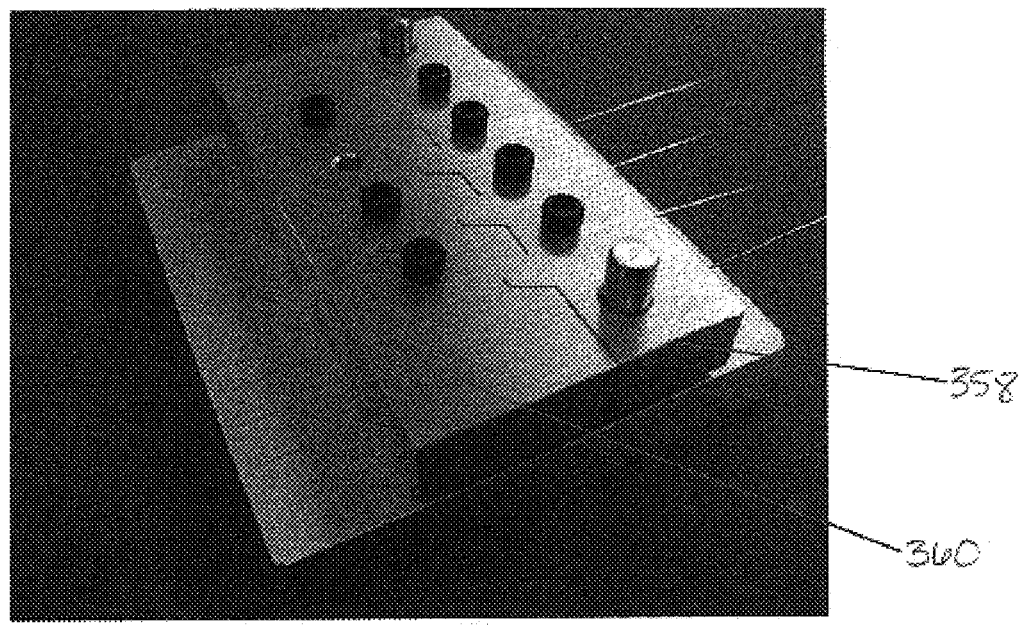
FIG. 29E illustrates a seal plate being lowered over the devices and screwed into place.
Figure 30:
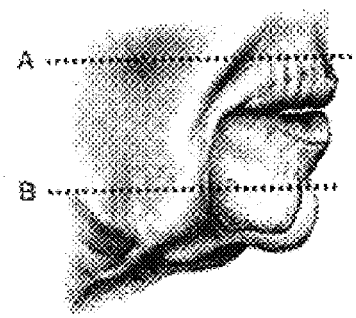
FIG. 30, line A illustrates a horizontal plane superior to the vermillion border of the lips.
Figure 31:
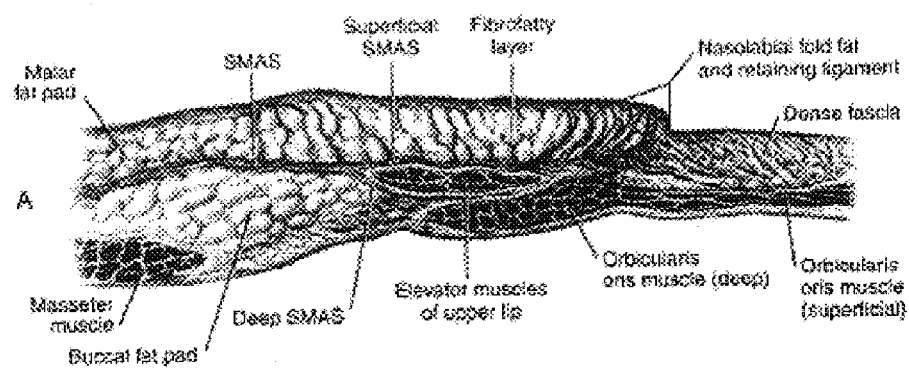
FIG. 31 is a cross-sectional view, generally through line A in FIG. 30, illustrating the anatomy of the various subdermal layers.

The next step is to seal the distal end of the implant. FIG. 29A illustrates various components utilizable in the sealing process. First, the distance from the open end of the lamination subassembly 336 is measured to preferably 2 cm, 3 cm, or 4 cm, depending on the desired inflated length of the implant. As in FIG. 29B, the lamination subassembly 336 is then inserted into the distal seal fixture 354 so that it protrudes past the clamping apex by the length of the desired inflated implant (preferably 2 cm, 3 cm, or 4 cm). Next, the lamination subassembly 336 is aligned on a base fixture within the inscribed guidelines. The distal seal fixture 354 in the preferred method supports the insertion of 5 devices, although a fixture may support any number of devices. When the lamination subassemblies are properly aligned, the clamping plate 358 is lowered and screwed into place, as in FIG. 29D. An arbor press 356 may be used to aid in lowering the plate. Next, the open end of the device 336 is filled with adhesive 340, again preferably MED2-4213. The adhesive 340 is then manually smoothed out lightly using fingers. The excess adhesive 340 is wiped off using a lint-free wipe. Then, the seal plate 360 is lowered onto the devices and screwed into place, as in FIG. 29E. The lamination subassemblies 336 are then cured in a calibrated oven for a minimum of 45 minutes at 145-155° C. The distal seal fixture 354 is then removed from the calibrated oven and placed on a copper cooling plate. Next, the distal seal fixture 354 is allowed to cool using the cold air vortex tube, as needed. Then, the clamp 358 and seal 360 plates are then unscrewed, and the lamination subassembly 336 is removed. A trim end die is then used to trim the distal tab 132. Lastly, the device is visually inspected for defects such as excessively asymmetrical tabs, noticeable adhesive failures, loose, unbonded ePTFE on the proximal tab, excessive adhesive migration into the expandable membrane, and any cuts or tears in the expandable membrane.

The next step is insertion of a fill tube. With the 0.016 inch mandrel protruding out of the neck tube on the proximal end, a 24-gauge catheter, preferably a yellow Angiocath, is slid over the mandrel and into the neck tube. A small amount of lubricant such as 99% IPA may be distributed over the proximal end of the device, to make the device more translucent and also to facilitate insertion of the catheter. Next, the catheter is then slid into the device ensuring the neck tube is not stretched out or the valve subassembly damaged. The catheter is then inserted until the valve subassembly is completely on the catheter tip and the catheter hub is within 2 mm of the proximal edge of the lamination subassembly. When the valve subassembly is entirely on the catheter tip, the 0.016 inch mandrel will loosen and then be removed. The fill tube is then visually inspected, and rejected if the catheter shaft is permanently kinked or bent, or if the fill tube is protruding past the neck tube inside the expandable membrane (99% IPA can be used to make the expandable membrane translucent).

The next step is to perform quality control testing on the fully constructed implant. Using a syringe filled with air, the implant is then filled until it is inflated, but not pressurized. A digital caliper or snap gage is then used to complete the dimension verification. An implant preferably should be within ±0.5 cm of its desired inflated length. The inflated diameter at the midpoint of the expandable membrane should be preferably 4.5±1.0 mm. The proximal tab is preferably 2.25±1.25 mm in width and 0.5±0.25 mm in thickness. The distal tab is also preferably also 2.25±1.25 mm in width and 0.5±0.25 mm in thickness. Any implants not conforming to the above dimension criteria are rejected.

Next, the implants are subjected to pressure decay testing. At the beginning of the shift, a leak tester, preferably a USON Sprint LC leak tester, is set to the following parameters: 3 psi test pressure, 5 sec fill, 5 sec stabilize, 30 sec test, auto dump, 0.050 psi reject level, 0.2 cc (0.05 cc/min) product volume. Next, the implant to be tested is connected to the leak tester with a flexible hose and a luer connection. The start button on the leak tester is then pressed to run the test. A green light on the leak tester signifies a passing test; a red light indicates failure. Implants that do not pass the pressure decay test should be discarded. Once assembled and quality control testing is complete, the implant is ready for packaging and distribution, and eventual implantation.

Following is a method of implantation of an inflatable nasolabial implant. In this embodiment, the patient's face is assessed by the physician in both a seated and supine, or reclining position. In particular, the length, depth and course of the patient's nasolabial folds are assessed by the physician. Next, a surgical pen is then used to mark directly on the patient's face the proposed implantation. Marks will typically be made indicating the point of initial entry of the implant, the point of exit of any delivery system components that make an exit through the skin and a line or lines that represent one or more of the following: the desired central axis of the implant, the desired most lateral edge of the implant, the desired most medial edge of the implant.

The physician then chooses the appropriate implant size and type, for example from among the available range of Juva Medical FulFil products, which can be made in a range of diameters (stated by the nominal "circular" diameter when filled to the maximum recommended volume) and lengths (stated as the unstressed natural length; the nasolabial implant is constructed so as to allow axial elongation once implanted in response to tissue movement) as well as different curvatures and end-tapers or contours. The physician then delivers the implant by one of several methods, which may be enabled by a delivery system.

One method of insertion is referred to as the "sew-through" method. In this method, the physician would first use the needle portion of a specialized delivery system (said needle portion being may be provided as a stand-alone needle, a needle with an attached suture or a needle element contained within a sleeve, cannula or at the distal end of shaft which contains other functional elements) to puncture through the skin at the desired entry location. The physician may choose to manually pinch the skin in this location so as to allow the needle (which is straight or relatively straight, in the latter case having a large radius of curvature so as to match the anatomical curvature found in the nasolabial fold of some patients) to pass first along a path that is somewhat normal to the skin surface (at an angle of between approximately 90 degrees and approximately 30 degrees) and then, once the needle tip has entered the subdermal tissue plane below the skin and being contained within the fibrofatty layer (adipose tissue) that lies between the dermis and the superficial musculoaponeurotic system (SMAS) that presents a higher resistance to the needle tip than does the fibrofatty layer, to then pass along a second path that remains within the fibrofatty layer tissue plane that is superficial to the SMAS and deep to the skin. Horizontal line A of FIG. 25 illustrates a horizontal plane superior to the vermillion border of the lips. FIG. 26 is a cross sectional view, generally around line A in FIG. 25, and illustrates the various described subdermal tissue layers. Line B represents a horizontal plane through the mandible.

In one embodiment, a delivery system can also be provided with a spring-coupled distal tip, or other force-based mechanism, that deflects when met with the increased resistance seen when the tip encounters the SMAS, thus steering the delivery system directly into the desired sub-dermal tissue plane.

Once the tip of the needle element is within the subdermal plane, the physician advances the needle or delivery system with needle tip extended, directing the tip toward the desired exit point. The physician may manually palpate the skin directly superficial to the path of the delivery system so as to better guide it along the desired path and to verify that it is on said path.

In another embodiment, a combined delivery system is used. One or more dissecting elements that are constituents of the delivery system are exposed after having been previously in an unexposed state. For example, the distal end of one preferred embodiment has two blade-like elements that swing outward from a recessed cavity within the shaft of the delivery system once said system is properly positioned in the subdermal plane. Activation of the first and second blade like elements from a first, percutaneously advancing configuration to a second, dissecting configuration can be accomplished by axially distally advancing or proximally retracting a tube or core positioned coaxially within an outer tubular body. Alternatively, a tissue dissection tool may be provided with a fixed forked distal end, with a left blade and a right blade having a V shaped space in-between. The opposing radially inwardly facing edges of the blades are sharpened, while the radially outwardly facing edges of the blades are blunt. The distal tips of the blade may be provided with an atraumatic end, such that tissue within the forked end of the blade is severed while surrounding tissue is preserved. As described in greater detail elsewhere in this disclosure, these blades serve to collect and then cut the connective fibrous fibers that are present in the fibrofatty layer and that are, in particular, distributed more densely in the tissue underlying the nasolabial fold (the deep attachment of said fibers being responsible for the "crease" that defines the nasolabial fold).

In an embodiment where a delivery system does not combine the dissection element or elements with the needle element, the needle element can be advanced fully until it exits at the desired exit point, at which point it is grasped either by the physicians fingers or by an instrument such as needle holder and withdrawn from the patient. Attached at the back of the needle or delivery system that contains the needle element is a suture or other tension-carrying member such as a fine stainless steel wire; said member is of sufficient length so as to have an excess of material still present at the proximal entry side of the implantation site after its distal attachment has exited from the distal exit point. For example, in the nasolabial fold, the distance between the entry and exit points will be between about 2 cm and about 7 cm, typically between about 3.5 cm and about 5.0 cm, thus the suture or suture-like member will be provided in a length of between about 5 cm and about 20 cm.

The continued presence within the tissue of the suture or suture-like element following the distal withdrawal of the needle now serves to define the location at which the implant will be placed as well as a path that may be taken by subsequent instruments or elements of the delivery system, in much the same way that a guide-wire is used to guide intravascular catheters.

For example, a dissecting element can now be advanced over the suture-like member and provide the same fiber-dissection as described above. Alternatively, a dissecting element can be inserted adjacent to the suture-like member and directed by the physician to undermine the desired tissue location and thus create a pocket or potential space for the implant to be placed. (The tissue undermining and creation of a pocket or potential space for placement of the implant was similarly accomplished in the alternative steps described above.)

Next, the placement of the implant can then be undertaken. In one embodiment, the implant is provided already attached to the suture, such as by having the suture pass through a distal tab portion, described in greater detail elsewhere in this disclosure, said suture then either creating a loop (attached at the needle) or being tied and knotted at the tab, or other attachment means.

In another embodiment, the implant is not provided already attached to the suture. The suture is provided with a second needle in this embodiment, said needle being either straight or arcuate as desired by the physician. The physician then "takes a bite" with this needle and draws the suture through a distal attachment tab on the implant and follows that with an attachment means as described above.

The physician then draws the implant into the desired location by applying tension to the suture. Said tension can be applied either by grasping the original insertion needle (now having exited distally) or the distal portion of the suture or both.

The implant can be aided in its entry into the proximal tissue entry by a funnel introducer which is constructed so as to urge the implant into a tightly rolled or folded configuration. The funnel introducer can be partially or fully pre-perforated or slit in one or more longitudinal lines or in a helical path, allowing it to be removed from around the implant or elements of the delivery system without requiring that it be retracted coaxially over said implant or elements.

In one embodiment, the implant can also be provided with a protective restraining sheath which causes it to remain in a tightly rolled or folded configuration while stored prior to use. Upon removal of said sheath, the polymeric materials of the implant will tend to remain in a rolled or folded configuration, thus reducing the frictional drag between the implant and the tissue as the implant is inserted. Since the transition at the distal end of the implant will cause the greatest such drag, the sheath may also be a partial sheath that restrains only a distal portion of the implant.

In another embodiment, the sheath may also be formed of a thin-walled, high-strength, relatively inelastic material such as polyethylene terephthalate, polyamide, polyimide, polyethylene or similar materials and may also have perforations as described above relative to the funnel introducer, and have a pull-tab or pull-line thereby allowing the implant to be inserted while the sheath (which may be full or partial) is still present. The sheath will act to reduce the diameter of the implant/sheath assembly by holding the implant in a tightly rolled or tightly folded configuration and will also act to smooth out size and shape transitions, both aspects serving to reduce the frictional drag and other difficulties encountered during implant insertion.

Alternatively, the same function just ascribed to the sheath can be provided by a binding element or elements, such as a fine filament, e.g. a small-diameter single or multi-strand fiber. Described elsewhere are specific advantageous designs and arrangements of implant binding(s) which constraining the implant in a tightly rolled or tightly folded configuration and also allow for removal of the binding(s) without undue force (which would disturb the position of the implant, said implant being in its desired position when said bindings would be removed) or the need for the implant to distort laterally to allow for unbinding.

A proximal suture or other proximal control element may also be present, for example by having a suture or suture loop attached to a proximal attachment tab of the implant.

The physician can assess implant location once it is inserted both visually and by manual palpation and, if desired, can adjust the position of the implant using the distal suture or, if present, the proximal suture, or both distal and proximal sutures.

Once the physician has positioned the implant as desired and verified that it is correctly positioned without having prolapsed on itself (this can be verified by locating the implant ends, which often can be palpated by a trained physician and comparing it to the known length of the implant, said comparison potentially being performed with a Juva-supplied length template, or by palpating to assure that there are no lumps that would be indicative of prolapse), the inflation of the implant with the desired can filler can be initiated.

The filler may be sterile normal saline or other liquid, a gas, such as air or carbon dioxide, or may be a mixture of liquid and gas. The filler may also be a viscous material such as an oil, or a cross-linked or non-cross-linked hyaluronic acid. The filler may also be a material that will polymerize and/or crosslink in situ, such as a mixture of two polyethylene glycols or of dimethyl siloxanes or other silicone elastomers.

The implant may have been prepared previously so as to remove substantially all of the air present within it prior to inflating with the filler. Such preparation can be accomplished in the typical fashion used with intravascular balloon catheters and referred to as "vacuum prep" or "aspiration prep."

The implant is then filled to a volume as desired by the physician. Typically, fill volumes will be at or below a "maximum flaccid fill level" that is provided for each implant size and type. Filling to this level or below creates a flaccidly filled implant which augments tissue volume (thus effacing the nasolabial fold or other wrinkles overlying the implant) without creating undue stresses within the tissue. Since it is flaccidly filled within a pocket or potential space created by the previous dissection step, the internal pressure within the implant is very low, typically 1 psi or less, preferably much less than 1 psi, such as 0.6 psi or less, 0.4 psi or less, or 0.3 psi or less. (The structural integrity of the implant is such that it can withstand much larger internal pressures, however, in order to provide for a safety factor and in order to withstand momentary increases in pressure that could result from contact of the patient's face with external objects. As described elsewhere, the elastomeric portion of the implant has the capacity to elongate to a great degree in response to either overfilling or increase in internal pressure, and the sealing components of the implant can likewise withstand such pressures.) As noted above, a preferred flaccid-filled implant may be filled to, for example, no greater than about 50%, 60%, 70%, 80%, or 90% of the maximum fill volume.

Next, the fill tube through which the filler was injected is then removed. The fill tube may be an elongate tube composed of one or more materials, the distal material having a higher durometer or flexural modulus than the proximal material. For example, the distal portion of the fill tube, of between about 1 cm and about 4 cm in length, can be a tube extruded from high-density polyethylene with an inside diameter of between about 0.005" and 0.020" and an outside diameter of between about 0.010" and 0.040". The distal portion of the fill tube can be heat-fused to a longer proximal portion of tube extruded from low-density polyethylene with the same range of dimensions. Having a longer proximal portion to the fill tube serves to mechanically isolate the implant from any disturbance that might occur to the proximal portion of the fill tube, such as when the physician or an assistant is handling an inflation device, such as a syringe, which is attached to the fill tube, said isolation being enabled by the flexion of the tubing. LDPE or similar materials are advantageous in that they combine relatively high flexibility with relatively high kink-resistance. Kinking of the fill tube is to be avoided as it would impinge on the lumen of the fill tube and thus make implant inflation difficult. HDPE is advantageous for the distal portion of the fill tube because it has sufficient hoop strength so as to resist compression by the valve assembly (described elsewhere) and because it has relatively low coefficients of static and dynamic friction, thus enabling the removal of the fill tube with minimum risk of disturbing the physical placement of the implant.

The attachment suture or sutures are then either removed from the implant by cutting the suture loop and withdrawing the remainder of the suture or are cut below the level of the skin by temporarily pushing the skin inward while cutting the suture, according to standard surgical technique.

In an alternative embodiment, an alternative placement approach is referred to as the "push through" method. This method may be used instead of the sew-through method or as an adjunct to it as will be described below. When used as an adjunct to the sew-through method, in addition to the traction applied by the distal suture and used to draw the implant into place during the insertion step, as described above, the physician uses a grasping instrument to grasp the distal end of the implant, for example by clamping across a distal tab of the implant, said instrument entering the tissue adjacent to the implant and through the same tissue entry point. It is advantageous that the grasping instrument is a specially designed instrument disclosed herein.

The physician then inserts the implant by pushing the grasping instrument into the tissue pocket (while continuing to grasp the implant distal tab); the physician may provide supplemental force and/or guidance by means of the distal suture. Funnel introduction, sheathing and/or binding can also be used as described above. Once positioned as desired, the physician releases the implant from the grasping instrument and withdraws the instrument. The procedure continues as described above.

The push-through method can also be used without a distal suture. In that case, the initial skin incision may be made by a needle which then is used to track on the desired path but does not exit distally, or by a scalpel blade. A pocket is then dissected, and then implanted in the manner described in the sew-through method above.

Figure 32:
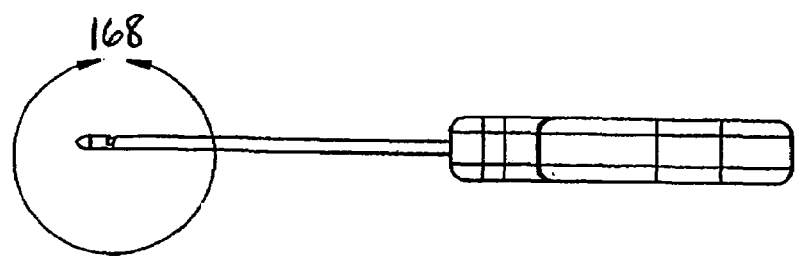
FIG. 32 is an embodiment of a specialized grasper, with the distal tip area of interest identified, according to one embodiment of the invention.
Figure 33:
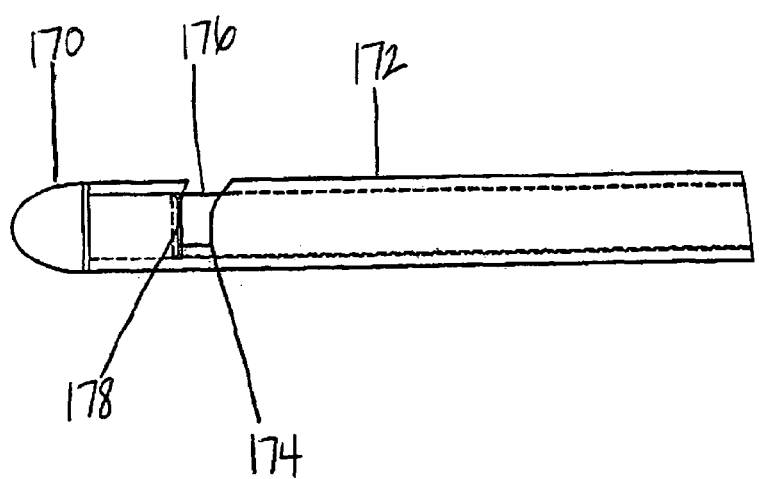
FIG. 33 is a detailed view of the tip of the specialized grasper of FIG. 27 according to one embodiment of the invention.

In another embodiment, also disclosed is a specialized grasping instrument for use in placing an inflatable soft tissue implant. Key advantages of this design over currently available instruments will be pointed out in the course of the description which follows. As seen in FIG. 33, the detail view (area circumscribed by 168 of FIG. 32), the instrument has its distal-most end a blunt tip 170 which allows the instrument to controllably pass through the tissue bed under the physician's control. The blunt, rounded tip 170 encourages the instrument to remain within the selected tissue plane, which, in the case of a nasolabial implant, is the sub-dermal plane. Existing grasping forceps may have flattened tips which, if held in improper orientation, can lead to exiting of the desired tissue plane.

The tip is attached or formed from the main tube body 172 of the instrument which contains a curved slot 174 near its distal end. The diameter of the main tube body 172 is ideally small enough to be able to pass through an initial skin incision that would be formed by a small surgical needle or the tip of an 11-blade scalpel. Preferably, the size of said needle would be 16 g (approximately 0.065" or 1.6 mm), 18 g, 20 g, or smaller, as needle sticks of the skin of that size or smaller typically do not require suture-closure. It is desirable to avoid suture-closure of the skin in an office-based or other minimally invasive cosmetic procedure as it reduces the possibility of temporary or permanent scarring and obviates a return visit for suture removal.

Currently available grasping forceps have minimum dimensions of 2 mm or more and are typically not circular in cross-section. For example, the smallest "alligator forceps" or "micro-forceps" available found in a Marina Medical catalog are 2 mm×3 mm in its cross-section. Since these forceps were not designed to be used in such a minimally invasive procedure as the implantation of the inflatable soft tissue implant, those dimensions are adequate. However, the disclosed grasper departs from typical surgical approaches by using a coaxial tube arrangement to provide a small-diameter circular cross-section. The circular cross-section is also advantageous in that it allows the user to simply rotate the product in order to move the grasping zone (which lies within the curved slot 174) away from the implant following implant release. In contrast, existing grasping forceps use a jaw-like motion (similar to an alligator's jaws) which requires a larger space within the tissue for the open position than for the closed position. The need for a larger space is a disfavored for the soft tissue implant for two reasons: the dissected pocket in which the implant is placed has been created with particular attention to its width and thickness, because a mismatch between pocket size and implant size can lead to implant migration, prolapse or other shape distortion. Moreover, the opened jaw of an ordinary grasping forceps is likely to disturb the position of the implant, which it has just released as the forceps is removed from the tissue. The ability of conventional grasping devices to rotate the currently available grasping forceps in an attempt to "clear" the implant and prevent this disturbance is thus severely limited because of the large extension of the open jaw out from the instrument's central axis.

The grasping function of the disclosed specialized grasping instrument is enabled by the slidable advancement of the plunger 176 against the fixed grasping face 178. In one method of construction, the fixed grasping face is the most proximal face of a separate tip element which include the blunt tip 170 and which is press-fit, or slip-fit and welded (such as by laser welding) in the distal end of the main tube 172, or some combination of those techniques, or of other attachment means such as adhesive or mechanical fasteners.

The opposing faces of the plunger 176 and the fixed grasping face 178 are constructed so as to be smooth, flat and parallel to each other so as to not endanger the implant by tearing or other mechanical damage. In contrast, currently available grasping forceps have ridges or teeth on the grasping surface, which may damage the implant.

The slot 174 shown is curved towards the proximal end of the instrument so that the distal portion of the implant can be grasped while the more proximal portion of the implant lies along the axis of the instrument, as it will be during the implantation procedure. A back-facing curve also reduces the frictional drag that the implant will see upon release from the instrument. This is advantageous because little or no forces are applied to the implant once it is in the desired position; disturbing it through frictional drag or by catching it with protruding portions of the delivery instrument would lead to incorrect positioning. The back-facing curve also makes the initial insertion of the distal tip of the implant (often a distal tab) into the slot 174 prior to insertion into the skin more easily.

Figure 34:
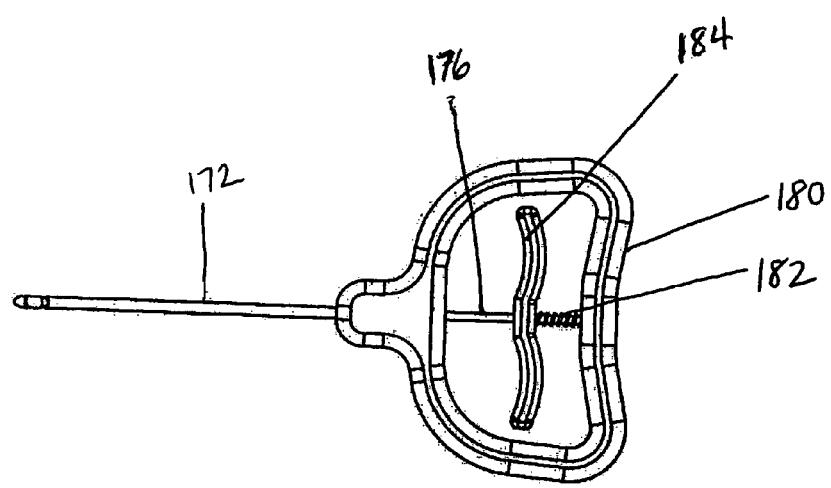
FIG. 34 is another line drawing of the specialized grasper, and illustrates the handle portion according to one embodiment of the invention.
Figure 35:
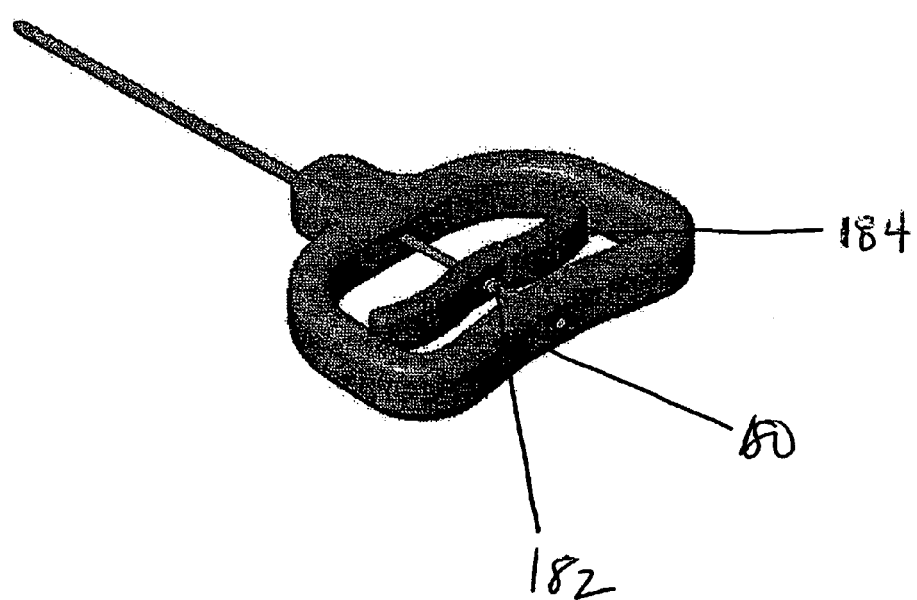
FIG. 35 is a three-dimensional view of the specialized grasper according to one embodiment of the invention.
Figure 40:
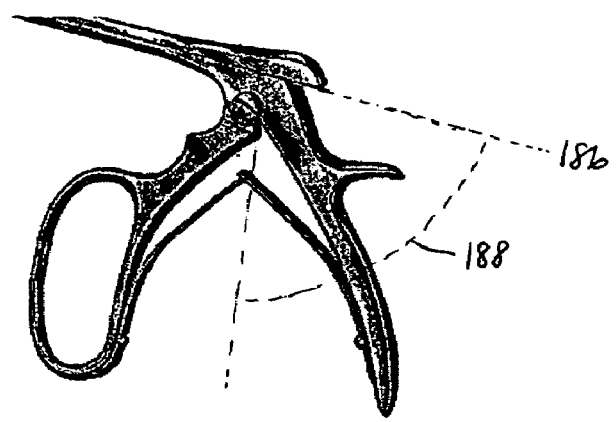
FIG. 40 is an example of an alternative embodiment for the handle of a specialized grasper, with the handle in an off-axis position.
Figure 41:
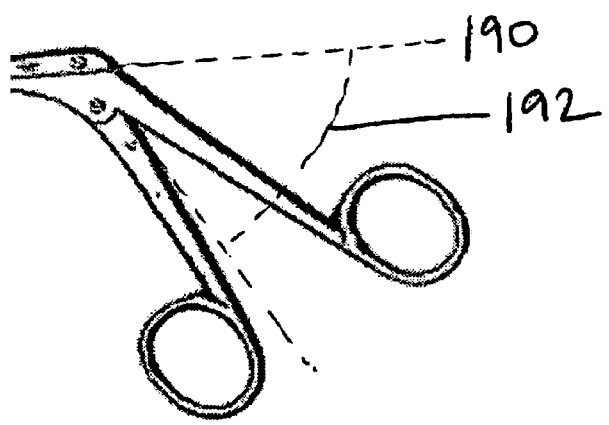
FIG. 41 is another example of an alternative embodiment for the handle of a specialized grasper, with the handle in an off-axis position.
Figure 42:
FIG. 42 is another example of an alternative embodiment for the handle of a specialized grasper.
Figure 43:
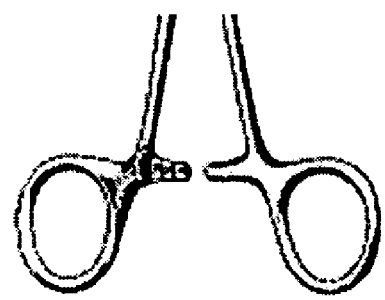
FIG. 43 is another example of an alternative embodiment for the handle of a specialized grasper, utilizing a ratcheting mechanism.

In the embodiment shown in FIG. 34, the grasping face of the plunger 176 is held against the fixed grasping face 178 by spring force. In order to open the grasping faces 176, 178 and insert the implant into the grasping slot 174, the physician uses his/her thumb against the back (proximal-most) surface of the main handle 180 while using two fingers against the front (distal-most) surface of the secondary handle 184. The main handle 180 is attached to the main tube 172 while the secondary handle 184 is attached to the plunger 176. Sliding the secondary handle 184, and thus the plunger 176, in a proximal direction causes the grasping faces 176, 178 to open and compresses the spring 182. The spring 182 is chosen so as to provide sufficient grasping force to the implant without exceeding that level of force that would cause damage to the materials of the implant. By using a spring 182 to apply the grasping force, the instrument prevents such damage. FIG. 35 is a representation of the grasper from an angular perspective, with key elements also shown in FIG. 34. Current grasping forceps do not use spring closure but rather have a ratcheting mechanism, as in FIG. 40, which allows as much force as the physician applies to be placed on the material being grasped and then locking that force in by means of the ratcheting mechanism.

Figure 36:
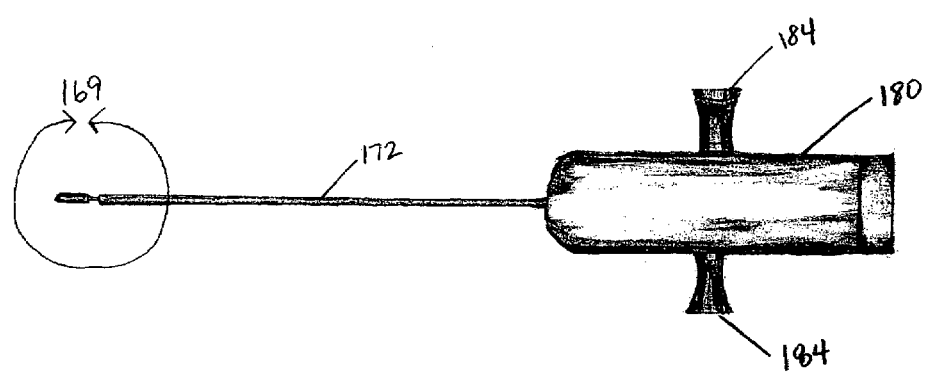
FIG. 36 is an alternative embodiment of a specialized grasper with an axially symmetric slot and alternative handle configuration.
Figure 37:
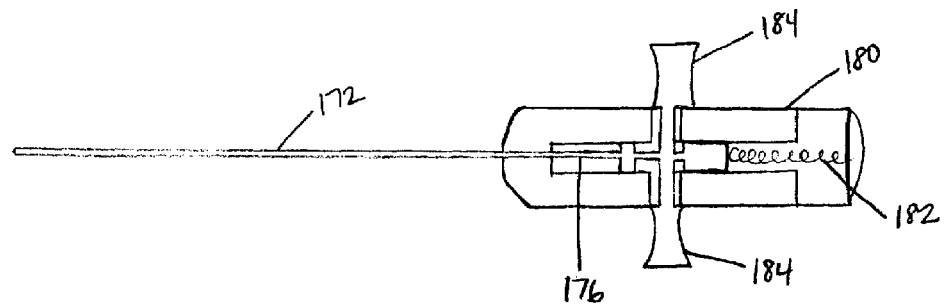
FIG. 37 is a cut-away view of the specialized grasper of FIG. 35.
Figure 38:
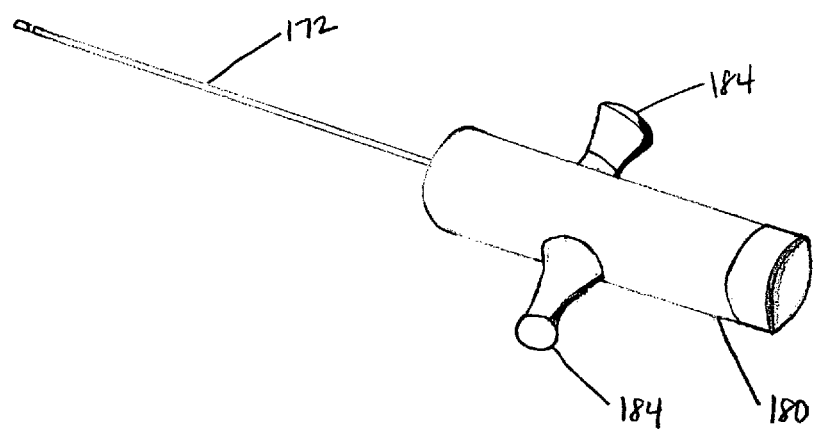
FIG. 38 is a three-dimensional view of the specialized grasper of FIG. 36 according to one embodiment of the invention.
Figure 39:
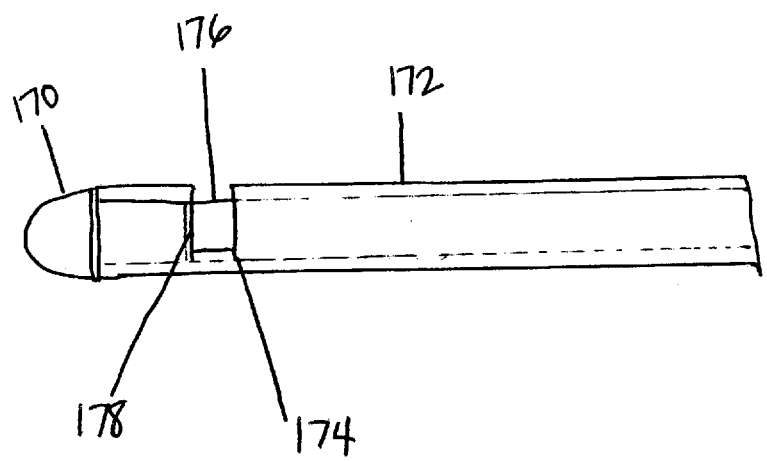
FIG. 39 is a detail view of the tip of the specialized grasper of FIG. 36 illustrating the axially symmetric slot.

In another preferred embodiment, FIGS. 36-39, the grasping slot 174 in the distal tip region 169 circled in FIG. 36 is axially symmetric, in contrast to the asymmetric curved slot shown in FIG. 33. This axially symmetric configuration of the slot is shown best in FIG. 39, illustrating the axially symmetric slot 174, plunger 176, and fixed grasping face 178. It allows an implant to be inserted in either an antegrade or retrograde fashion. In an antegrade method of implantation, the grasper is pushed through a single incision, pulling the distal tip of the implant, which drags behind the distal tip of the grasper. In a retrograde method of implantation, in addition to the initial implant puncture, a second puncture is made, the grasper alone is inserted through it, advanced until its tip emerges through the initial, typically inferior puncture, at which point the implant is grasped and then pulled into the tissue. The retrograde approach has the benefit of not requiring both implant and grasper to be present simultaneously in a skin incision. In this embodiment, an alternate grasper handle position is also disclosed as shown in FIG. 36, which may be preferred by some physicians. The secondary handles 184, extend outwardly from the main handle 180, may be grasped with two fingers on their (distal-most) surface of the secondary handle 184, with one or more other fingers used to support the main handle 180. The skilled artisan will note that the handleS 180, 184 depicted in FIG. 34 may also be adapted to have an axially symmetric grasping slot 174. FIG. 37 is a cut-away view of the grasper of FIG. 36, additionally showing a spring 182 and a plunger 176. FIG. 38 is a representation of the grasper embodiment of FIGS. 36 and 37 from an angular perspective.

While one such preferred embodiment is shown, the key advantages of the disclosed grasping instrument can be preserved in a variety of other embodiments as well, such as FIGS. 40-43. For example, the handle portion could be moved into a position 188, 192 off the axis 186, 190 so as to move the physician's hands further from the patient's face and reduce the possibility of the patient's facial features obstructing the motion of the instrument. For example, handles of the type pictured in FIG. 40 or FIG. 41 could be used. In addition, the spring-closure could be replaced by a free-sliding mechanism that is manually locked by a thumb-screw or similar locking mechanism, such as once the physician judged that appropriate grasping force had been applied. Alternatively, the ratcheting mechanisms could be used, such as FIG. 43 or particularly if the implant materials were of sufficient strength so as to withstand the forces applied across the smooth grasping faces.

Also, although a coaxial tube design has been described here, the same advantageous circular-cross section can be obtained using two sliding members that lie next to each other and are linked through a T-slot, as is commonly done in surgical instruments.

Another useful embodiment, particularly for delivery of inflatable implants in the sub-orbital region such as tear-trough implants, is a curved version of the grasper. A gentle curve is desirable, such as one that is a circular arc with a radius of curvature of between 2 and 6 inches, preferably about 4 inches. For many facial applications in particular those in the periorbital region, the instrument should not be excessively long, such as having an arc length of between 2 and 6 inches, preferably about 3 inches. In curved embodiments, the plunger element will be constructed of a tight-mesh wound or braided cable so as to be able to curve and still carry column loading with only negligible axial compression. In the T-slot (upper and lower slidable members) embodiments, the two members can be formed from circular arcs as well and maintain the slidable motion of the straight embodiments.

Although the present invention has been described in connection with certain specific embodiments, various additional embodiments and alterations to the described embodiments are contemplated within the scope of the invention. Accordingly, the scope of the invention is not intended to be limited by the foregoing, and is intended to extend to the full extent of the attached claims.

What is claimed is:

1. An implantable tissue augmentation device, comprising:
   an elongate, flexible tubular body, having a proximal end, a distal end and a cavity;

a valved opening on the proximal end;
a closed distal end;
a first, inner layer for retaining inflation media within the implant, and a second, outer microporous layer for enabling tissue ingrowth; and
at least one grasping means to allow positioning of the device at a desired site, wherein the grasping means comprises at least one tab.

2. The tissue augmentation device of claim 1, wherein the at least one tab comprises an aperture for connection to a suture.

3. The tissue augmentation device of claim 1, wherein the outer layer comprises ePTFE and the inner layer comprises at least one of silicone, polyurethane, or a thermoplastic elastomer.

4. The tissue augmentation device of claim 1, wherein the inflation media comprises one or more fluids.

5. The tissue augmentation device of claim 4, wherein said one or more fluids comprises saline.

6. The tissue augmentation device of claim 1, including a filler comprising a material that can be manually shaped to a desired configuration before the filler transforms to retain a molded configuration.

7. The tissue augmentation device of claim 1, wherein the tissue augmentation device permits passage of a fill tube, but at least substantially reseals following removal of the fill tube.

8. The tissue augmentation device of claim 1, wherein the tissue augmentation device comprises a plurality of internal baffles which divide an interior cavity of the device into a plurality of compartments.

9. The tissue augmentation device of claim 1, wherein said device comprises at least two compartments that are adapted to be filled separately in order to vary the contour of the filled region.

10. The tissue augmentation device of claim 1, wherein introduction of the inflation media transforms the device from a first configuration to a second configuration, wherein the second configuration has a diameter at an axial midpoint of about 1 mm to about 10 mm.

11. The tissue augmentation device of claim 10, wherein an inflatable portion of the device has a length within the range of from about 1 cm to about 6 cm.

12. The tissue augmentation device of claim 10, wherein said device has a diameter within the range of from about 1 mm to about 8 mm.

13. The tissue augmentation device of claim 1, wherein said device has a wall thickness within the range of from about 0.003 inches to about 0.020 inches.

14. The tissue augmentation device of claim 10, wherein the first configuration of said device has a diameter of less than about 1.6 mm.

15. The tissue augmentation device of claim 1, further comprising one suture.

16. An augmentation system comprising the tissue augmentation device of claim 1, and a dissection tool to separate tissue beneath a treatment site and create an implantation space.

17. A tissue augmentation system comprising the tissue augmentation device of claim 1, and a fill tube for introducing the inflation media.

18. A kit including a plurality tissue augmentation devices of claim 1, wherein said plurality of tissue augmentation devices is provided in a plurality of sizes to permit the user to select a desired size.

19. The kit of claim 18, wherein at least one of the tissue augmentation devices has a fully inflated diameter of: 1-10 mm.

20. An implantable tissue augmentation device for treating facial wrinkles, comprising:
an elongate, flexible tubular body, having a proximal end, a distal end and a cavity, wherein the tubular body has a first cross-section and a second cross-section; the first cross-section having a cross-sectional area that is at least 110% of the second cross-section;
a valved opening on the proximal end;
a closed distal end;
a first configuration and a second configuration, wherein said tissue augmentation device is transformable from the first configuration to the second configuration by introduction of a filler into the cavity via the valved opening; and
an inner layer and an outer layer, wherein the outer layer comprises a porous material to encourage fibrous ingrowth and wherein the inner layer comprises an elastomeric material that adds flexibility to the body and is for contact with the filler material, wherein the inner and outer layers are bonded together.

21. The tissue augmentation device of claim 20, wherein the tubular body comprises a tapered portion between the first and second cross-section.

22. The tissue augmentation device of claim 20, wherein the tubular body comprises an accelerated curve shape between the first and second cross-section.

23. The tissue augmentation device of claim 20, wherein the tubular body comprises a progressive curve shape between the first and second cross-section.

24. The tissue augmentation device of claim 20, wherein the valved opening further comprises a tube surrounded by an elastomeric material.

25. The tissue augmentation device of claim 24, further comprising a valve plug.

26. The tissue augmentation device of claim 20, where the valved opening further comprises an additional sealing element.

27. The tissue augmentation device of claim 20, further comprising an unbonded zone between the inner and outer layers.

28. The tissue augmentation device of claim 27, where the length of the unbonded zone is at least 10% of the length of the device.

29. The tissue augmentation device of claim 20, wherein the outer layer and inner layers are configured to have substantial compliance matching with native surrounding tissues.

30. The tissue augmentation device of claim 20, further comprising a distal tab.

31. The tissue augmentation device of claim 30, said distal tab provided with a through passage.

32. The tissue augmentation device of claim 30, said distal tab measuring about 2.25±1.25 mm in width and 0.5±0.25 mm in thickness.

33. The tissue augmentation device of claim 20, further comprising a proximal tab.

34. The tissue augmentation device of claim 33, the proximal tab providing a fixation zone for the valved opening.

35. The tissue augmentation device of claim 33, said proximal tab measuring about 2.25±1.25 mm in width and 0.5±0.25 mm in thickness.

36. The tissue augmentation device of claim 20, said device having an axial length of 1-10 cm.

37. The tissue augmentation device of claim 20, said device having an axial length of 2-4 cm.

38. The tissue augmentation device of claim 20 said device having a maximum fill volume of 10-25 cc.

39. An implantable tissue augmentation device, comprising:
- an elongate, flexible tubular body, having a proximal end, a distal end and a cavity;
- a valved opening on the proximal end;
- a closed distal end;
- a first, inner layer for retaining inflation media within the implant, and a second, outer microporous layer for enabling tissue ingrowth; and
- a filler comprising a material that can be manually shaped to a desired configuration before the filler transforms to retain a molded configuration.

40. The tissue augmentation device of claim 39, wherein the device comprises at least one grasping means to allow positioning of the device at a desired site.

41. The tissue augmentation device of claim 40, wherein the grasping means comprises at least one tab.

42. The tissue augmentation device of claim 41, wherein the at least one tab comprises an aperture for connection to a suture.

43. The tissue augmentation device of claim 39, wherein the outer layer comprises ePTFE and the inner layer comprises at least one of silicone, polyurethane, or a thermoplastic elastomer.

44. The tissue augmentation device of claim 39, wherein the inflation media comprises one or more fluids.

45. The tissue augmentation device of claim 44, wherein said one or more fluids comprises saline.

46. The tissue augmentation device of claim 39, wherein the tissue augmentation device permits passage of a fill tube, but at least substantially reseals following removal of the fill tube.

47. The tissue augmentation device of claim 39, wherein the tissue augmentation device comprises a plurality of internal baffles which divide an interior cavity of the device into a plurality of compartments.

48. The tissue augmentation device of claim 39, wherein said device comprises at least two compartments that are adapted to be filled separately in order to vary the contour of the filled region.

49. The tissue augmentation device of claim 39, wherein introduction of the inflation media transforms the device from a first configuration to a second configuration, wherein the second configuration has a diameter at an axial midpoint of about 1 mm to about 10 mm.

50. The tissue augmentation device of claim 49, wherein an inflatable portion of the device has a length within the range of from about 1 cm to about 6 cm.

51. The tissue augmentation device of claim 49, wherein said device has a diameter within the range of from about 1 mm to about 8 mm.

52. The tissue augmentation device of claim 39, wherein said device has a wall thickness within the range of from about 0.003 inches to about 0.020 inches.

53. The tissue augmentation device of claim 49, wherein the first configuration of said device has a diameter of less than about 1.6 mm.

54. The tissue augmentation device of claim 39, further comprising one suture.

55. An augmentation system comprising the tissue augmentation device of claim 39, and a dissection tool to separate tissue beneath a treatment site and create an implantation space.

56. A tissue augmentation system comprising the tissue augmentation device of claim 39, and a fill tube for introducing the inflation media.

57. A kit including a plurality tissue augmentation devices of claim 39, wherein said plurality of tissue augmentation devices is provided in a plurality of sizes to permit the user to select a desired size.

58. The kit of claim 57, wherein at least one of the tissue augmentation devices has a fully inflated diameter of 1-10 mm.

59. An implantable tissue augmentation device for treating facial wrinkles, comprising:
- an elongate, flexible tubular body, having a proximal end, a distal end and a cavity;
- a valved opening on the proximal end comprising a tube surrounded by an elastomeric material;
- a valve plug;
- a closed distal end;
- a first configuration and a second configuration, wherein said tissue augmentation device is transformable from the first configuration to the second configuration by introduction of a filler into the cavity via the valved opening; and
- an inner layer and an outer layer, wherein the outer layer comprises a porous material to encourage fibrous ingrowth and wherein the inner layer comprises an elastomeric material that adds flexibility to the body and is for contact with the filler material, wherein the inner and outer layers are bonded together.

60. The tissue augmentation device of claim 59, wherein the tubular body has a first cross-section and a second cross-section; the first cross-section having a cross-sectional area that is at least 110% of the second cross-section.

61. The tissue augmentation device of claim 59, wherein the tubular body comprises a tapered portion between the first and second cross-section.

62. The tissue augmentation device of claim 59, wherein the tubular body comprises an accelerated curve shape between the first and second cross-section.

63. The tissue augmentation device of claim 59, wherein the tubular body comprises a progressive curve shape between the first and second cross-section.

64. The tissue augmentation device of claim 59, where the valved opening further comprises an additional sealing element.

65. The tissue augmentation device of claim 59, further comprising an unbonded zone between the inner and outer layers.

66. The tissue augmentation device of claim 65, where the length of the unbonded zone is at least 10% of the length of the device.

67. The tissue augmentation device of claim 59, wherein the outer layer and inner layers are configured to have substantial compliance matching with native surrounding tissues.

68. The tissue augmentation device of claim 59, further comprising a distal tab.

69. The tissue augmentation device of claim 68, said distal tab provided with a through passage.

70. The tissue augmentation device of claim 68, said distal tab measuring about 2.25±1.25 mm in width and 0.5±0.25 mm in thickness.

71. The tissue augmentation device of claim 59, further comprising a proximal tab.

72. The tissue augmentation device of claim 71, the proximal tab providing a fixation zone for the valved opening.

73. The tissue augmentation device of claim 71, said proximal tab measuring about 2.25±1.25 mm in width and 0.5±0.25 mm in thickness.

74. The tissue augmentation device of claim 59, said device having an axial length of 1-10 cm.

75. The tissue augmentation device of claim 59, said device having an axial length of 2-4 cm.

76. The tissue augmentation device of claim 59 said device having a maximum fill volume of 10-25 cc.

77. An implantable tissue augmentation device for treating facial wrinkles, comprising:
an elongate, flexible tubular body, having a proximal end, a distal end and a cavity;
a valved opening on the proximal end;
a closed distal end;
a first configuration and a second configuration, wherein said tissue augmentation device is transformable from the first configuration to the second configuration by introduction of a filler into the cavity via the valved opening;
an inner layer and an outer layer, wherein the outer layer comprises a porous material to encourage fibrous ingrowth and wherein the inner layer comprises an elastomeric material that adds flexibility to the body and is for contact with the filler material, wherein the inner and outer layers are bonded together; and
an unbonded zone between the inner and outer layers.

78. The tissue augmentation device of claim 77, wherein the tubular body has a first cross-section and a second cross-section; the first cross-section having a cross-sectional area that is at least 110% of the second cross-section.

79. The tissue augmentation device of claim 77, wherein the tubular body comprises a tapered portion between the first and second cross-section.

80. The tissue augmentation device of claim 77, wherein the tubular body comprises an accelerated curve shape between the first and second cross-section.

81. The tissue augmentation device of claim 77, wherein the tubular body comprises a progressive curve shape between the first and second cross-section.

82. The tissue augmentation device of claim 77, wherein the valved opening further comprises a tube surrounded by an elastomeric material.

83. The tissue augmentation device of claim 82, further comprising a valve plug.

84. The tissue augmentation device of claim 77, where the valved opening further comprises an additional sealing element.

85. The tissue augmentation device of claim 77, where the length of the unbonded zone is at least 10% of the length of the device.

86. The tissue augmentation device of claim 77, wherein the outer layer and inner layers are configured to have substantial compliance matching with native surrounding tissues.

87. The tissue augmentation device of claim 77, further comprising a distal tab.

88. The tissue augmentation device of claim 87, said distal tab provided with a through passage.

89. The tissue augmentation device of claim 87, said distal tab measuring about 2.25±1.25 mm in width and 0.5±0.25 mm in thickness.

90. The tissue augmentation device of claim 77, further comprising a proximal tab.

91. The tissue augmentation device of claim 90, the proximal tab providing a fixation zone for the valved opening.

92. The tissue augmentation device of claim 90, said proximal tab measuring about 2.25±1.25 mm in width and 0.5±0.25 mm in thickness.

93. The tissue augmentation device of claim 77, said device having an axial length of 1-10 cm.

94. The tissue augmentation device of claim 77, said device having an axial length of 2-4 cm.

95. The tissue augmentation device of claim 77 said device having a maximum fill volume of 10-25 cc.

96. An implantable tissue augmentation device for treating facial wrinkles, comprising:
an elongate, flexible tubular body, having a proximal end, a distal end and a cavity;
a valved opening on the proximal end;
a closed distal end;
a distal tab;
a first configuration and a second configuration, wherein said tissue augmentation device is transformable from the first configuration to the second configuration by introduction of a filler into the cavity via the valved opening; and
an inner layer and an outer layer, wherein the outer layer comprises a porous material to encourage fibrous ingrowth and wherein the inner layer comprises an elastomeric material that adds flexibility to the body and is for contact with the filler material, wherein the inner and outer layers are bonded together.

97. The tissue augmentation device of claim 96, wherein the tubular body has a first cross-section and a second cross-section; the first cross-section having a cross-sectional area that is at least 110% of the second cross-section.

98. The tissue augmentation device of claim 96, wherein the tubular body comprises a tapered portion between the first and second cross-section.

99. The tissue augmentation device of claim 96, wherein the tubular body comprises an accelerated curve shape between the first and second cross-section.

100. The tissue augmentation device of claim 96, wherein the tubular body comprises a progressive curve shape between the first and second cross-section.

101. The tissue augmentation device of claim 96, wherein the valved opening further comprises a tube surrounded by an elastomeric material.

102. The tissue augmentation device of claim 101, further comprising a valve plug.

103. The tissue augmentation device of claim 96, where the valved opening further comprises an additional sealing element.

104. The tissue augmentation device of claim 96, further comprising an unbonded zone between the inner and outer layers.

105. The tissue augmentation device of claim 104, where the length of the unbonded zone is at least 10% of the length of the device.

106. The tissue augmentation device of claim 96, wherein the outer layer and inner layers are configured to have substantial compliance matching with native surrounding tissues.

107. The tissue augmentation device of claim 96, said distal tab provided with a through passage.

108. The tissue augmentation device of claim 96, said distal tab measuring about 2.25±1.25 mm in width and 0.5±0.25 mm in thickness.

109. The tissue augmentation device of claim 96, further comprising a proximal tab.

110. The tissue augmentation device of claim 109, the proximal tab providing a fixation zone for the valved opening.

111. The tissue augmentation device of claim 109, said proximal tab measuring about 2.25±1.25 mm in width and 0.5±0.25 mm in thickness.

112. The tissue augmentation device of claim 96, said device having an axial length of 1-10 cm.

113. The tissue augmentation device of claim 96, said device having an axial length of 2-4 cm.

114. The tissue augmentation device of claim 96 said device having a maximum fill volume of 10-25 cc.

115. An implantable tissue augmentation device for treating facial wrinkles, comprising:
- an elongate, flexible tubular body, having a proximal end, a distal end and a cavity;
- a valved opening on the proximal end;
- a closed distal end;
- a proximal tab;
- a first configuration and a second configuration, wherein said tissue augmentation device is transformable from the first configuration to the second configuration by introduction of a filler into the cavity via the valved opening; and
- an inner layer and an outer layer, wherein the outer layer comprises a porous material to encourage fibrous ingrowth and wherein the inner layer comprises an elastomeric material that adds flexibility to the body and is for contact with the filler material, wherein the inner and outer layers are bonded together.

116. The tissue augmentation device of claim 115, wherein the tubular body has a first cross-section and a second cross-section; the first cross-section having a cross-sectional area that is at least 110% of the second cross-section.

117. The tissue augmentation device of claim 115, wherein the tubular body comprises a tapered portion between the first and second cross-section.

118. The tissue augmentation device of claim 115, wherein the tubular body comprises an accelerated curve shape between the first and second cross-section.

119. The tissue augmentation device of claim 115, wherein the tubular body comprises a progressive curve shape between the first and second cross-section.

120. The tissue augmentation device of claim 115, wherein the valved opening further comprises a tube surrounded by an elastomeric material.

121. The tissue augmentation device of claim 120, further comprising a valve plug.

122. The tissue augmentation device of claim 115, where the valved opening further comprises an additional sealing element.

123. The tissue augmentation device of claim 115, further comprising an unbonded zone between the inner and outer layers.

124. The tissue augmentation device of claim 123, where the length of the unbonded zone is at least 10% of the length of the device.

125. The tissue augmentation device of claim 115, wherein the outer layer and inner layers are configured to have substantial compliance matching with native surrounding tissues.

126. The tissue augmentation device of claim 115, further comprising a distal tab.

127. The tissue augmentation device of claim 126, said distal tab provided with a through passage.

128. The tissue augmentation device of claim 126, said distal tab measuring about 2.25±1.25 mm in width and 0.5±0.25 mm in thickness.

129. The tissue augmentation device of claim 115, the proximal tab providing a fixation zone for the valved opening.

130. The tissue augmentation device of claim 115, said proximal tab measuring about 2.25±1.25 mm in width and 0.5±0.25 mm in thickness.

131. The tissue augmentation device of claim 115, said device having an axial length of 1-10 cm.

132. The tissue augmentation device of claim 115, said device having an axial length of 2-4 cm.

133. The tissue augmentation device of claim 115 said device having a maximum fill volume of 10-25 cc.

* * * * *

UNITED STATES PATENT AND TRADEMARK OFFICE
CERTIFICATE OF CORRECTION

PATENT NO. : 7,641,688 B2  Page 1 of 1
APPLICATION NO. : 11/316215
DATED : January 5, 2010
INVENTOR(S) : Michael Lesh It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 956 days.

Signed and Sealed this

Twenty-first Day of December, 2010

David J. Kappos
*Director of the United States Patent and Trademark Office*